(12) United States Patent
Kraynov et al.

(10) Patent No.: US 8,329,869 B2
(45) Date of Patent: Dec. 11, 2012

(54) MODIFIED INTERFERON BETA POLYPEPTIDES AND THEIR USES

(75) Inventors: Vadim Kraynov, San Diego, CA (US); Nick Knudsen, San Diego, CA (US); Anna-Maria A. Hays Putnam, San Diego, CA (US); Denise Krawitz, San Diego, CA (US); Jason Pinkstaff, Encinitas, CA (US); Heather Myler, Port Monmouth, NJ (US)

(73) Assignee: Ambrx, Inc., La Jolla, CA (US)

( * ) Notice: Subject to any disclaimer, the term of this patent is extended or adjusted under 35 U.S.C. 154(b) by 0 days.

(21) Appl. No.: 13/344,891

(22) Filed: Jan. 6, 2012

(65) Prior Publication Data

US 2012/0197006 A1    Aug. 2, 2012

Related U.S. Application Data

(62) Division of application No. 12/112,890, filed on Apr. 30, 2008, now Pat. No. 8,114,630.

(60) Provisional application No. 60/927,528, filed on May 2, 2007.

(51) Int. Cl.
*C07K 14/52* (2006.01)
*C07K 14/00* (2006.01)

(52) U.S. Cl. ......... 530/351; 530/350; 530/402; 435/440

(58) Field of Classification Search ...................... None
See application file for complete search history.

(56) References Cited

U.S. PATENT DOCUMENTS

| | | | | |
|---|---|---|---|---|
| 7,270,809 | B2 * | 9/2007 | Cox, III | 424/85.7 |
| 7,314,613 | B2 * | 1/2008 | Patten et al. | 424/85.7 |
| 8,093,356 | B2 * | 1/2012 | Hays et al. | 530/351 |
| 8,114,630 | B2 * | 2/2012 | Kraynov et al. | 435/69.1 |
| 8,232,371 | B2 * | 7/2012 | Cho et al. | 530/351 |
| 2003/0082575 | A1 * | 5/2003 | Schultz et al. | 435/6 |
| 2004/0115774 | A1 * | 6/2004 | Kochendoerfer et al. | 435/69.5 |

* cited by examiner

*Primary Examiner* — Christine J Saoud
*Assistant Examiner* — Jegatheesan Seharaseyon
(74) *Attorney, Agent, or Firm* — John W. Wallen, III; Kristin S. Eaton

(57) ABSTRACT

Modified interferon beta polypeptides and uses thereof are provided.

6 Claims, 32 Drawing Sheets

Figure 6
A
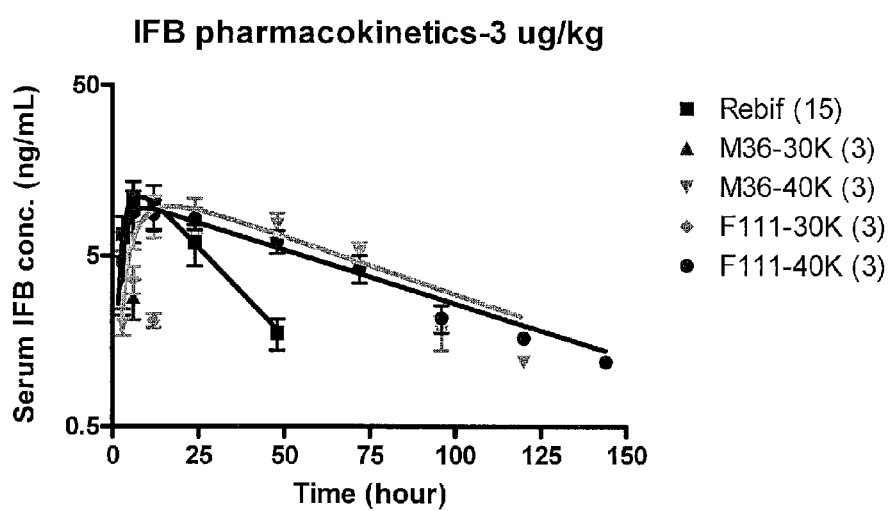
B
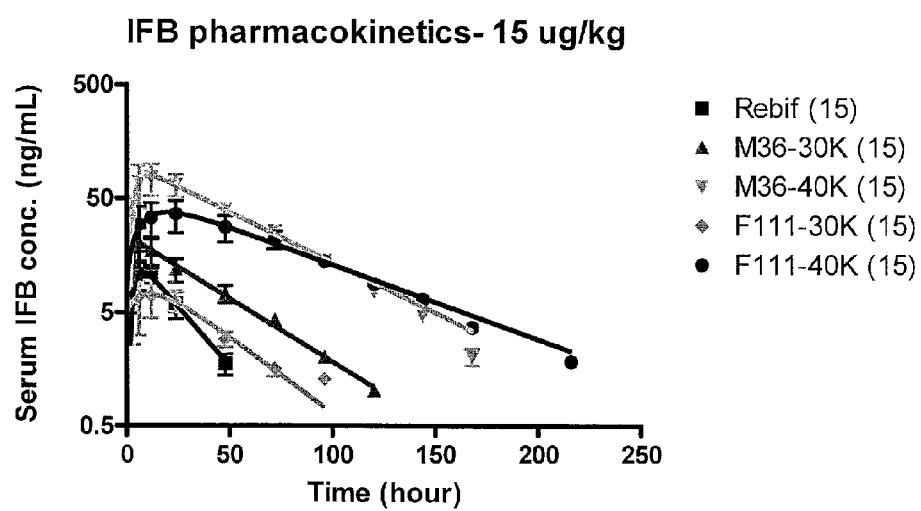

Figure 7
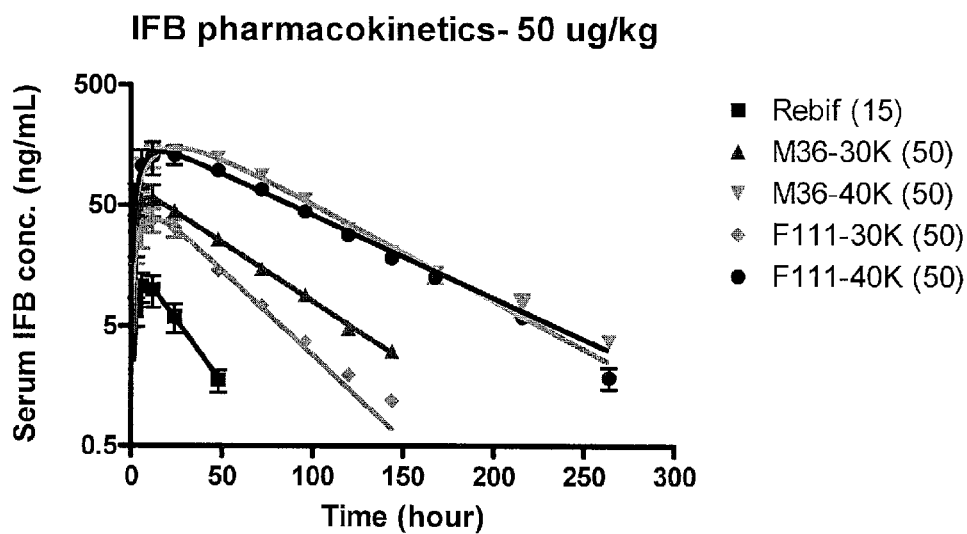
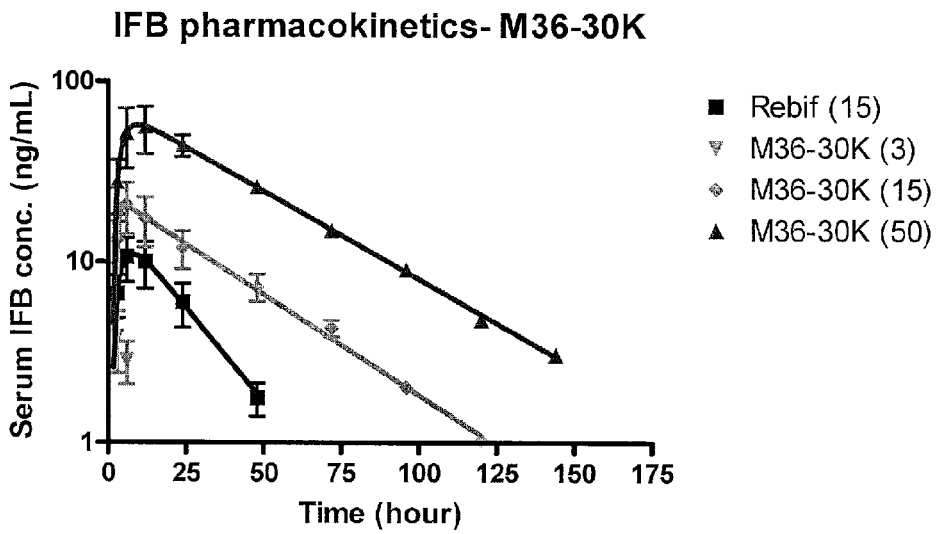

Figure 8
A
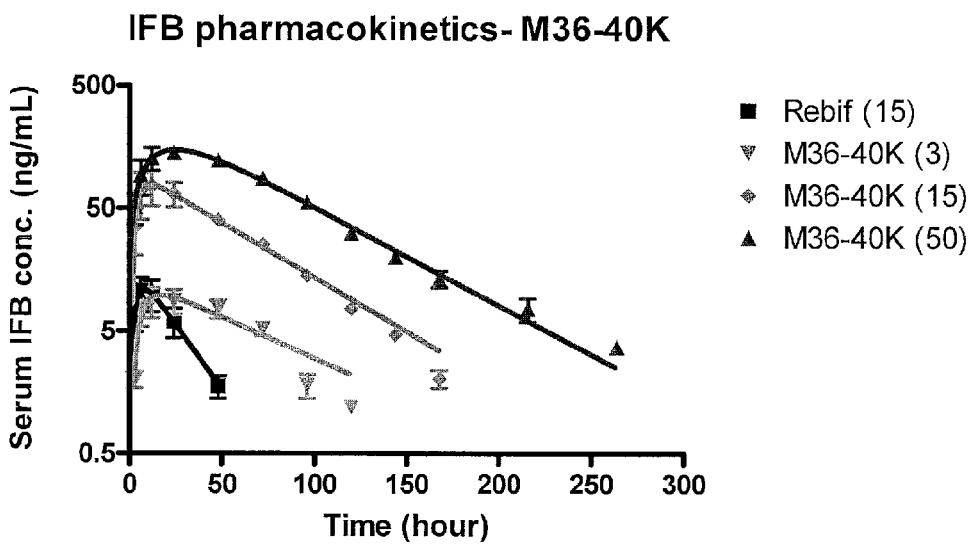
B
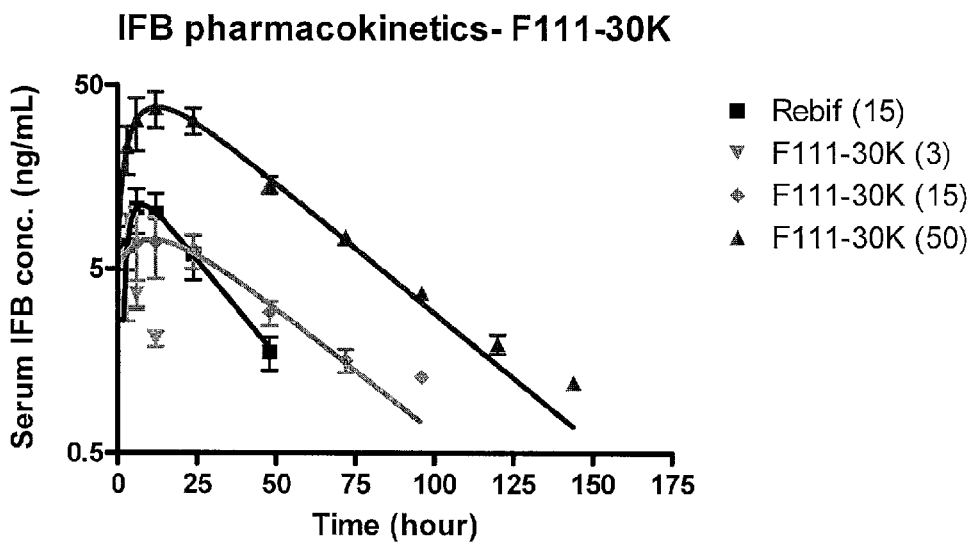

Figure 9
A
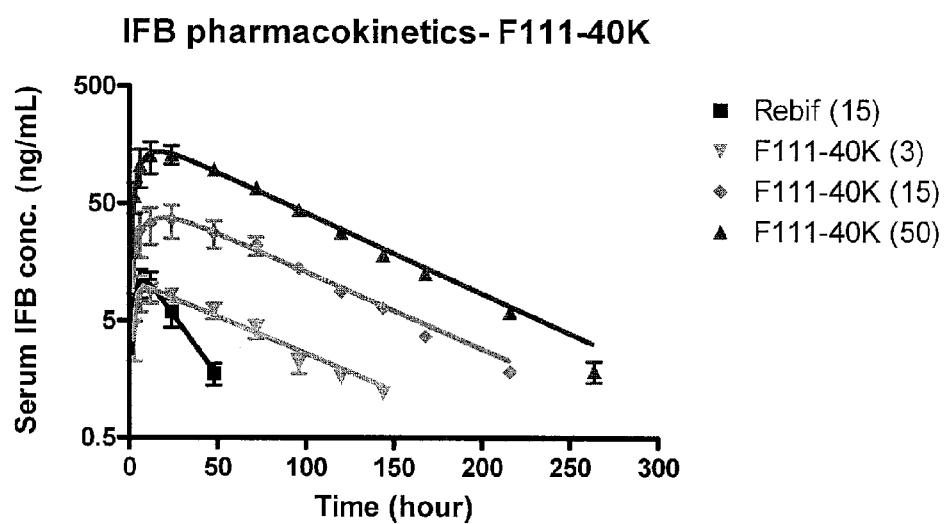
B
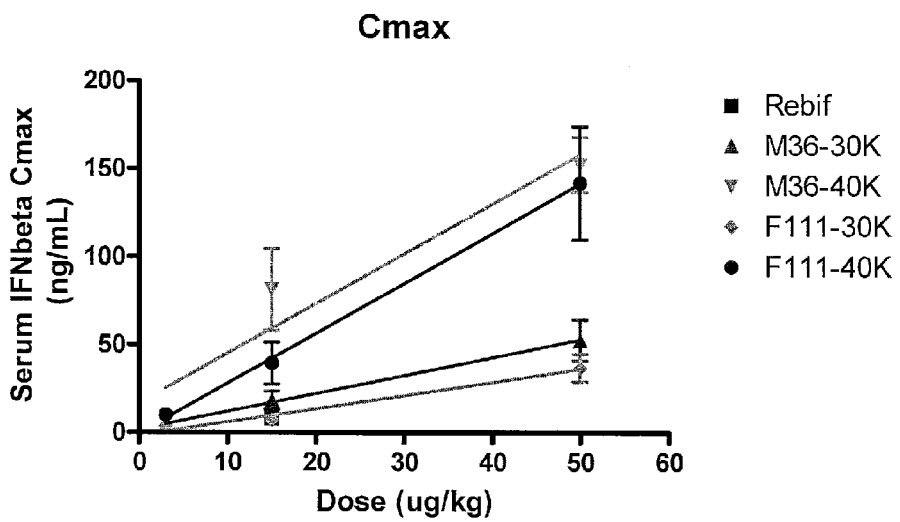

Figure 11
A
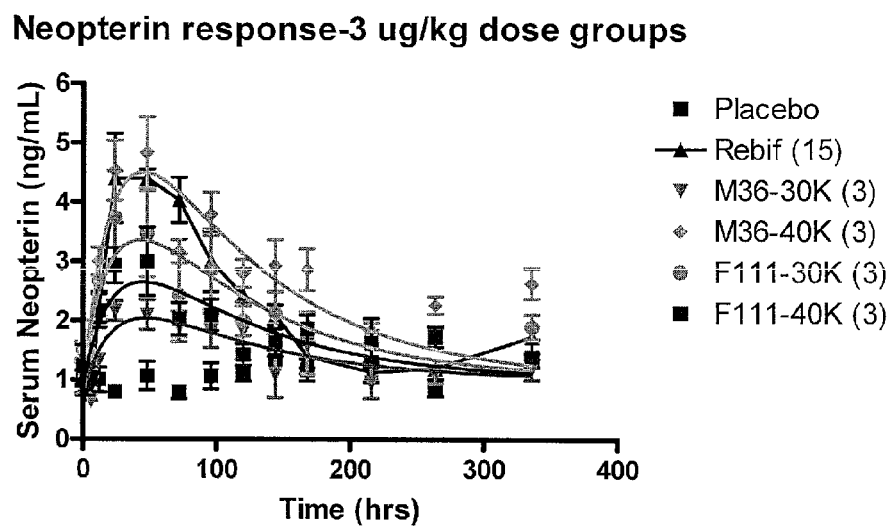
B
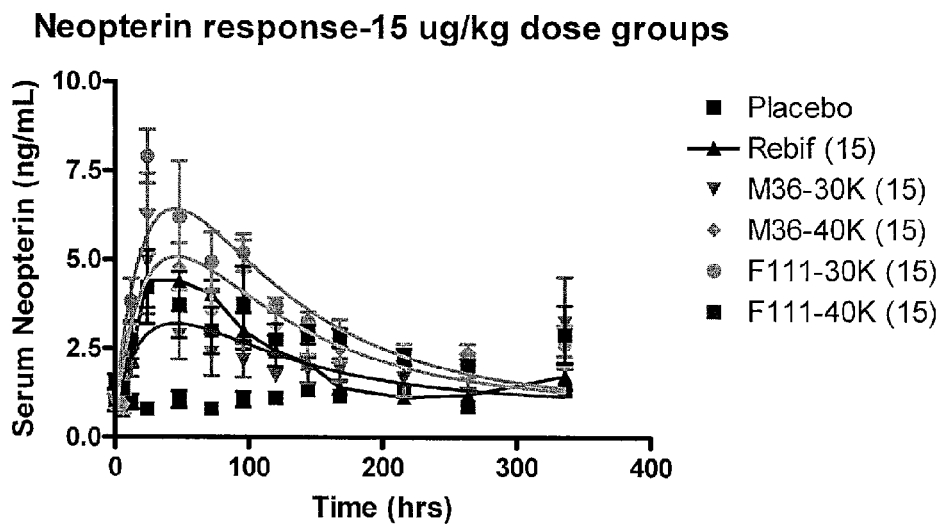

Figure 12
A
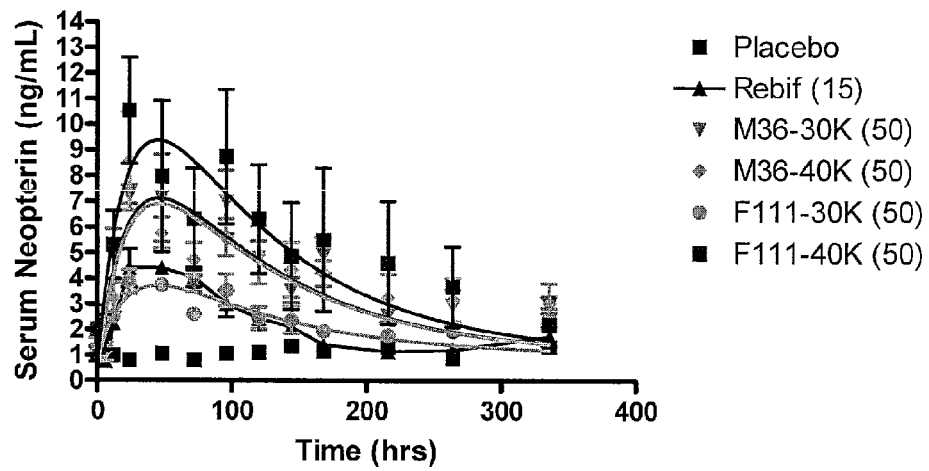
B
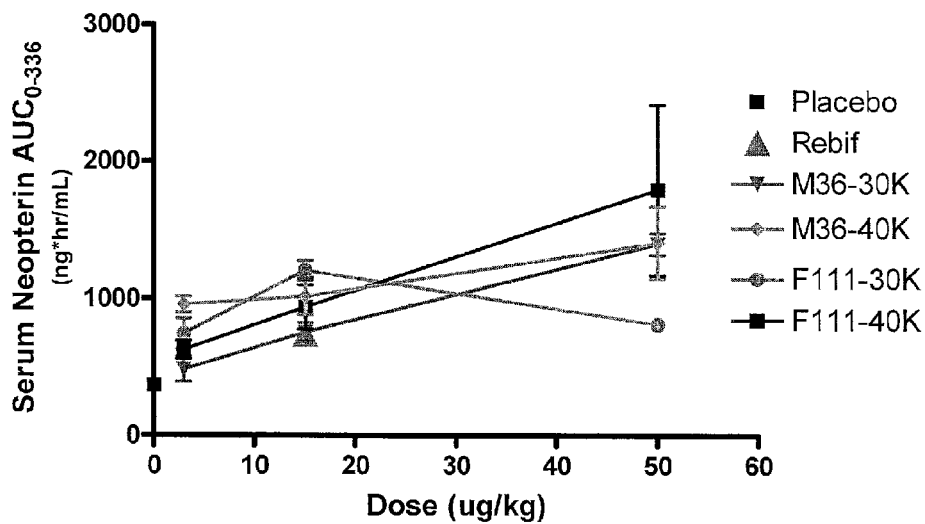

Figure 13
A
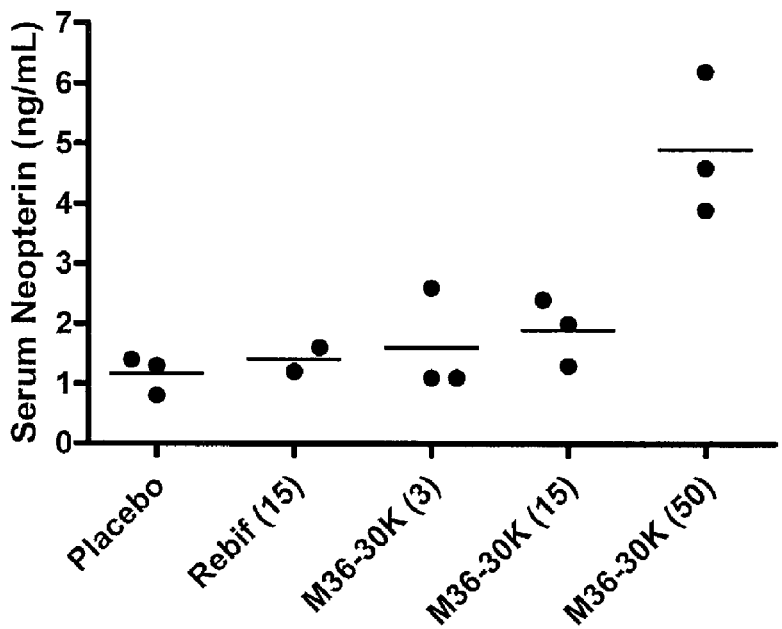
B
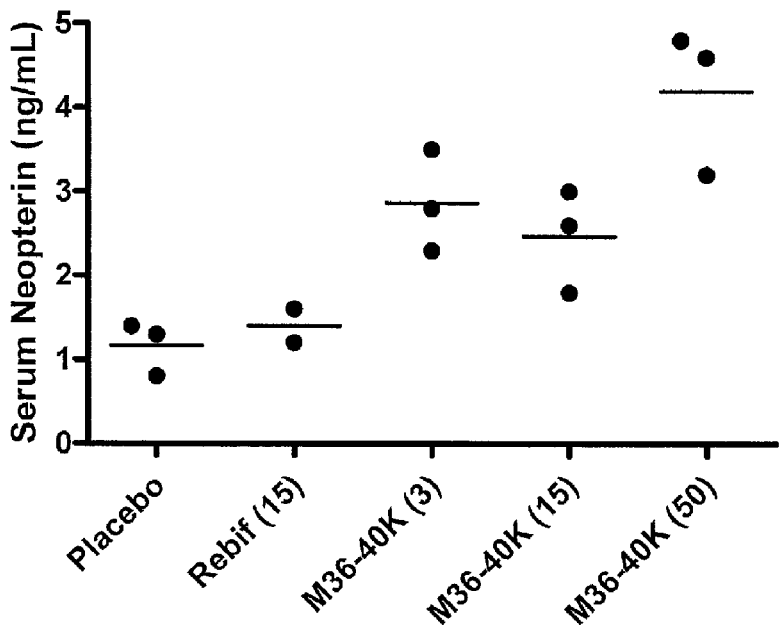

Figure 16
A
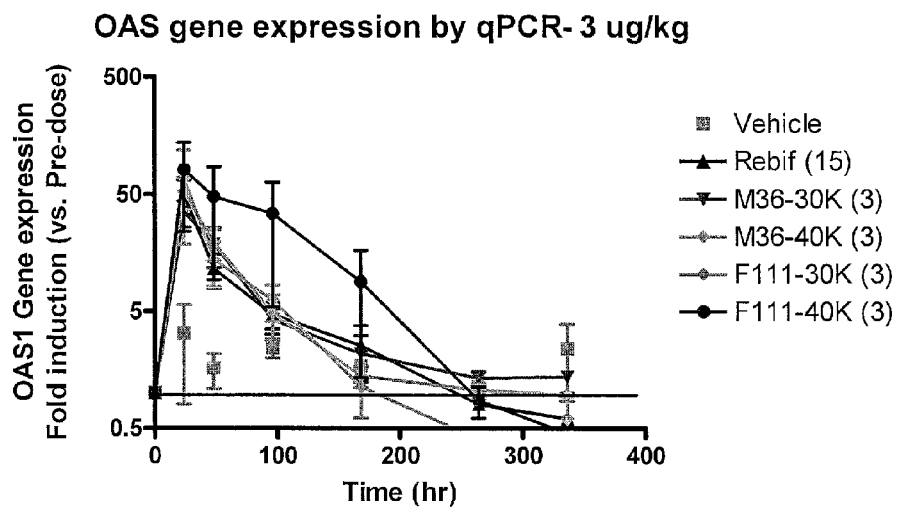
*1 point excluded from 1 vehicle animal
B
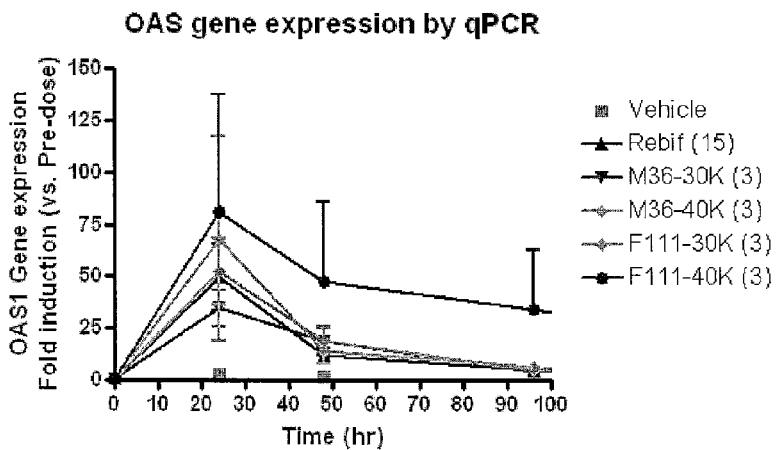

Figure 17
A
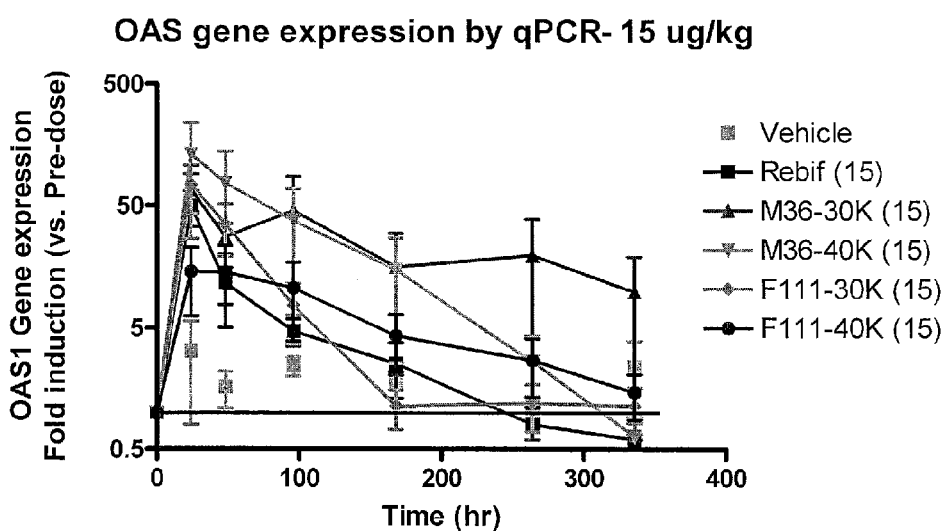
*1 point excluded from 1 vehicle animal
B
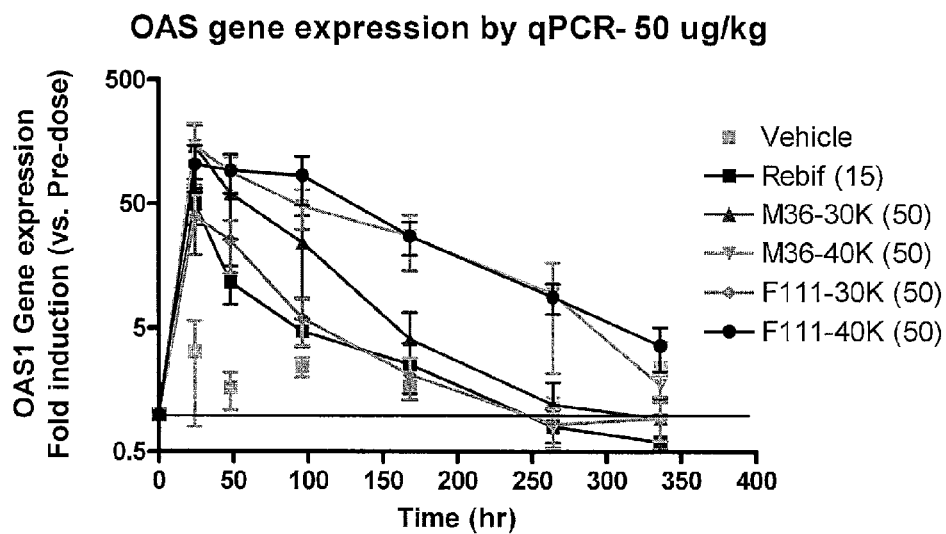
*1 point excluded from 1 vehicle animal

Figure 20

| | Albumin | Alkaline Phosphatase (ALP) | Alanine Aminotransferase (ALT) | Aspartate Transaminase (AST) | Total Bilirubin | Calcium | Total Cholesterol | Creatine Kinase (CK) | Creatine | Gamma Glutamyl Transaminase (GGT) |
|---|---|---|---|---|---|---|---|---|---|---|
| Treatment Group | | | | | | | | | | |
| Rebif | N.S. | N.S. | N.S. | N.S. | N.S. | N.S. | N.S. | N.S. | N.S. | N.S. |
| M36-30K (3ug) | N.S. | N.S. | N.S. | N.S. | N.S. | N.S. | N.S. | N.S. | N.S. | N.S. |
| M36-30K (15ug) | N.S. | N.S. | N.S. | N.S. | N.S. | N.S. | N.S. | N.S. | N.S. | N.S. |
| M36-30K (50ug) | N.S. | N.S. | N.S. | N.S. | N.S. | N.S. | N.S. | N.S. | N.S. | N.S. |
| M36-40K (3ug) | N.S. | N.S. | N.S. | N.S. | N.S. | N.S. | N.S. | N.S. | N.S. | N.S. |
| M36-40K (15ug) | N.S. | N.S. | N.S. | N.S. | N.S. | N.S. | N.S. | N.S. | N.S. | N.S. |
| M36-40K (50ug) | N.S. | N.S. | N.S. | N.S. | N.S. | N.S. | N.S. | N.S. | N.S. | N.S. |
| F111-30K (3ug) | N.S. | N.S. | N.S. | N.S. | N.S. | N.S. | N.S. | N.S. | N.S. | N.S. |
| F111-30K (15ug) | N.S. | N.S. | N.S. | N.S. | N.S. | N.S. | N.S. | N.S. | N.S. | N.S. |
| F111-30K (50ug) | N.S. | N.S. | N.S. | N.S. | N.S. | N.S. | N.S. | N.S. | N.S. | N.S. |
| F111-40K (3ug) | N.S. | N.S. | N.S. | N.S. | N.S. | N.S. | N.S. | N.S. | N.S. | N.S. |
| F111-40K (15ug) | N.S. | N.S. | N.S. | N.S. | N.S. | N.S. | N.S. | N.S. | N.S. | N.S. |
| F111-40K (50ug) | N.S. | N.S. | N.S. | N.S. | N.S. | N.S. | N.S. | N.S. | N.S. | N.S. |

Figure 21

| Treatment Group | Inorganic Phosphorus | Total Protein (TP) | Triglyceride | Blood Urea Nitrogen (BUN) | Sodium | Potassium | Chloride | Globulin | Albumin:Globulin Ratio |
|---|---|---|---|---|---|---|---|---|---|
| Rebif | N.S. | N.S. | N.S. | N.S. | N.S. | N.S. | N.S. | N.S. | N.S. |
| M36-30K (3ug) | N.S. | N.S. | N.S. | N.S. | N.S. | N.S. | N.S. | N.S. | N.S. |
| M36-30K (15ug) | N.S. | N.S. | N.S. | N.S. | N.S. | N.S. | N.S. | N.S. | N.S. |
| M36-30K (50ug) | N.S. | N.S. | N.S. | N.S. | N.S. | N.S. | N.S. | N.S. | N.S. |
| M36-40K (3ug) | N.S. | N.S. | N.S. | N.S. | N.S. | N.S. | N.S. | N.S. | N.S. |
| M36-40K (15ug) | N.S. | N.S. | N.S. | N.S. | N.S. | N.S. | N.S. | N.S. | N.S. |
| M36-40K (50ug) | N.S. | N.S. | N.S. | N.S. | N.S. | N.S. | N.S. | N.S. | N.S. |
| F111-30K (3ug) | N.S. | N.S. | N.S. | N.S. | N.S. | N.S. | N.S. | N.S. | N.S. |
| F111-30K (15ug) | N.S. | N.S. | N.S. | N.S. | N.S. | N.S. | N.S. | N.S. | N.S. |
| F111-30K (50ug) | N.S. | N.S. | N.S. | N.S. | N.S. | N.S. | N.S. | N.S. | N.S. |
| F111-40K (3ug) | N.S. | N.S. | N.S. | N.S. | N.S. | N.S. | N.S. | N.S. | N.S. |
| F111-40K (15ug) | N.S. | N.S. | N.S. | N.S. | N.S. | N.S. | N.S. | N.S. | N.S. |
| F111-40K (50ug) | N.S. | N.S. | N.S. | N.S. | N.S. | N.S. | N.S. | N.S. | N.S. |

Panel A

Panel B

Panel A

Panel B

```
                        SEQUENCE LISTING

<160> NUMBER OF SEQ ID NOS: 24

<210> SEQ ID NO 1
<211> LENGTH: 166
<212> TYPE: PRT
<213> ORGANISM: Artificial
<220> FEATURE:
<223> OTHER INFORMATION: Amino acid sequence of IFN beta with C17S
      substitution

<400> SEQUENCE: 1

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45
```

Gln Phe Gln Lys Glu Asp Ala Ala Leu Thr Ile Tyr Glu Met Leu Gln
            50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 498
<212> TYPE: DNA
<213> ORGANISM: Artificial
<220> FEATURE:
<223> OTHER INFORMATION: Nucleotide sequence of IFN beta with C17S
      substitution (optimized 5' end)

<400> SEQUENCE: 2
atgagctaca acttgcttgg attcctgcag cgttcttcta actttcagag ccagaaactg      60
ctgtggcagc ttaacggtcg tctggagtac tgccttaaag accgtatgaa cttcgacatc     120
ccggaagaaa tcaaacagct ccagcagttc aaaaagaag acgcggccct gaccatctac      180
gaaatgctgc agaacatctt cgcgatcttt cgtcaggata gctctagcac cggttggaat     240
gaaaccatcg ttgaaaacct gcttgctaac gttaccacc agattaacca ccttaaaacc      300
gttcttgaag aaaaactgga aaagaagac ttcacccgtg gtaaactgat gtctagcctg      360
cacctgaagc gttactacgg tcgtatcctg cactaccta aagccaaaga atattctcac      420
tgcgcgtgga ccatcgttcg tgttgaaatc ctgcgtaact tctacttcat caaccgtctg     480
accggctacc tgcgcaac                                                   498

<210> SEQ ID NO 3
<211> LENGTH: 166
<212> TYPE: PRT
<213> ORGANISM: Homo sapiens

<400> SEQUENCE: 3

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
             35                  40                  45

Gln Phe Gln Lys Glu Asp Ala Ala Leu Thr Ile Tyr Glu Met Leu Gln
            50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr

```
                  100                 105                 110
Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 4
<211> LENGTH: 187
<212> TYPE: PRT
<213> ORGANISM: Homo sapiens

<400> SEQUENCE: 4

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 5
<211> LENGTH: 77
<212> TYPE: DNA
<213> ORGANISM: Artificial
<220> FEATURE:
<223> OTHER INFORMATION: Mutant tRNA derived from Methanococcus
      jannaschii tRNA

<400> SEQUENCE: 5
ccggcggtag ttcagcaggg cagaacggcg gactctaaat ccgcatggcg ctggttcaaa    60
tccagcccgc cggacca                                                    77

<210> SEQ ID NO 6
<211> LENGTH: 306
<212> TYPE: PRT
<213> ORGANISM: Artificial
<220> FEATURE:
<223> OTHER INFORMATION: Mutant synthetase derived from Methanococcus
``` jannaschii synthetase

<400> SEQUENCE: 6

```
Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Val
            20                  25                  30
Ile Gly Phe Glu Pro Ser Gly Lys Ile His Leu Gly His Tyr Leu Gln
        35                  40                  45
Ile Lys Lys Met Ile Asp Leu Gln Asn Ala Gly Phe Asp Ile Ile Ile
    50                  55                  60
Tyr Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu His Gly Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Gly Ile His
145                 150                 155                 160
Tyr Glu Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Glu Ile Arg Ala
    210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
        275                 280                 285
Asn Ala Val Ala Glu Glu Leu Ile Lys Ile Leu Glu Pro Ile Arg Lys
    290                 295                 300
Arg Leu
305
```

<210> SEQ ID NO 7
<211> LENGTH: 77
<212> TYPE: DNA
<213> ORGANISM: Methanococcus jannaschii

<400> SEQUENCE: 7

```
ccggcggtag ttcagcaggg cagaacggcg gactctaaat ccgcatggcg ctggttcaaa    60
tccggcccgc cggacca                                                   77
```

<210> SEQ ID NO 8
<211> LENGTH: 88
<212> TYPE: DNA

-continued

<213> ORGANISM: Artificial
<220> FEATURE:
<223> OTHER INFORMATION: Optimized amber supressor tRNA

<400> SEQUENCE: 8
cccagggtag ccaagctcgg ccaacggcga cggactctaa atccgttctc gtaggagttc    60
gagggttcga atcccttccc tgggacca                                       88

<210> SEQ ID NO 9
<211> LENGTH: 89
<212> TYPE: DNA
<213> ORGANISM: Artificial
<220> FEATURE:
<223> OTHER INFORMATION: Optimized AGGA frameshift supressor tRNA

<400> SEQUENCE: 9
gcgagggtag ccaagctcgg ccaacggcga cggacttcct aatccgttct cgtaggagtt    60
cgagggttcg aatccctccc ctcgcacca                                      89

<210> SEQ ID NO 10
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-L-phenylalanine

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
    275                 280                 285

Asn Ala Val Ala Glu Glu Leu Ile Lys Ile Leu Glu Pro Ile Arg Lys
290                 295                 300

Arg Leu
305

<210> SEQ ID NO 11
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-benzoyl-L-phenylalanine

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 12
<211> LENGTH: 305
<212> TYPE: PRT
<213> ORGANISM: Artificial
<220> FEATURE:
<223> OTHER INFORMATION: Aminoacyl tRNA synthetase for the
      incorporation of propargyl-phenylalanine

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
290                 295                 300

Leu
305

<210> SEQ ID NO 13
<211> LENGTH: 305

<212> TYPE: PRT
<213> ORGANISM: Artificial
<220> FEATURE:
<223> OTHER INFORMATION: Aminoacyl tRNA synthetase for the
      incorporation of propargyl-phenylalanine

<400> SEQUENCE: 13

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 14
<211> LENGTH: 305
<212> TYPE: PRT
<213> ORGANISM: Artificial
<220> FEATURE:
<223> OTHER INFORMATION: Aminoacyl tRNA synthetase for the
      incorporation of propargyl-phenylalanine

<400> SEQUENCE: 14

Met Asp Glu Phe Glu Met Ile Lys Arg Asn Thr Ser Glu Ile Ile Ser

```
                1               5                  10                 15
    Glu Glu Glu Leu Arg Glu Val Leu Lys Lys Asp Glu Lys Ser Ala Ala
                    20                  25                 30

Ile Gly Phe Glu Pro Ser Gly Lys Ile His Leu Gly His Tyr Leu Gln
                    35                  40                 45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
    65                  70                  75                 80

Glu Ile Arg Lys Ile Gly Asp Tyr Asn Lys Lys Val Phe Glu Ala Met
                    85                  90                 95

Gly Leu Lys Ala Lys Tyr Val Tyr Gly Ser Lys Phe Gln Leu Asp Lys
                    100                 105                110

Asp Tyr Thr Leu Asn Val Tyr Arg Leu Ala Leu Lys Thr Thr Leu Lys
                    115                 120                125

Arg Ala Arg Arg Ser Met Glu Leu Ile Ala Arg Glu Asp Glu Asn Pro
                    130                 135                140

Lys Val Ala Glu Val Ile Tyr Pro Ile Met Gln Val Asn Ala Ile Tyr
    145                 150                 155                160

Leu Ala Val Asp Val Ala Val Gly Gly Met Glu Gln Arg Lys Ile His
                    165                 170                175

Met Leu Ala Arg Glu Leu Leu Pro Lys Lys Val Val Cys Ile His Asn
                    180                 185                190

Pro Val Leu Thr Gly Leu Asp Gly Gly Lys Met Ser Ser Ser Lys
                    195                 200                205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
    225                 230                 235                240

Met Glu Ile Ala Lys Tyr Phe Leu Glu Tyr Pro Leu Thr Ile Lys Arg
                    245                 250                255

Pro Glu Lys Phe Gly Gly Asp Leu Thr Val Asn Ser Tyr Glu Glu Leu
                    260                 265                270

Glu Ser Leu Phe Lys Asn Lys Glu Leu His Pro Met Asp Leu Lys Asn
                    275                 280                285

Ala Val Ala Glu Glu Leu Ile Lys Ile Leu Glu Pro Ile Arg Lys Arg
                    290                 295                300

Leu
    305

<210> SEQ ID NO 15
    <211> LENGTH: 306
    <212> TYPE: PRT
    <213> ORGANISM: Artificial
    <220> FEATURE:
    <223> OTHER INFORMATION: Aminoacyl tRNA synthetase  for the
          incorporation of p-azido-phenylalanine

<400> SEQUENCE: 15

Met Asp Glu Phe Glu Met Ile Lys Arg Asn Thr Ser Glu Ile Ile Ser
    1               5                   10                 15

Glu Glu Glu Leu Arg Glu Val Leu Lys Lys Asp Glu Lys Ser Ala Thr
                    20                  25                 30

Ile Gly Phe Glu Pro Ser Gly Lys Ile His Leu Gly His Tyr Leu Gln
                    35                  40                 45

Ile Lys Lys Met Ile Asp Leu Gln Asn Ala Gly Phe Asp Ile Ile Ile
```

```
              50                  55                  60
Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Asn Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 16
<211> LENGTH: 306
<212> TYPE: PRT
<213> ORGANISM: Artificial
<220> FEATURE:
<223> OTHER INFORMATION: Aminoacyl tRNA synthetase  for the
      incorporation of p-azido-phenylalanine

<400> SEQUENCE: 16

Met Asp Glu Phe Glu Met Ile Lys Arg Asn Thr Ser Glu Ile Ile Ser
  1                   5                  10                  15

Glu Glu Glu Leu Arg Glu Val Leu Lys Lys Asp Glu Lys Ser Ala Thr
                 20                  25                  30

Ile Gly Phe Glu Pro Ser Gly Lys Ile His Leu Gly His Tyr Leu Gln
             35                  40                  45

Ile Lys Lys Met Ile Asp Leu Gln Asn Ala Gly Phe Asp Ile Ile Ile
         50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Ser Phe Gln Leu Asp Lys
```

```
                    100                 105                 110
Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
        290                 295                 300

Arg Leu
305

<210> SEQ ID NO 17
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 17

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65              70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Pro Val His
```

```
                145                 150                 155                 160
Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 18
<211> LENGTH: 306
<212> TYPE: PRT
<213> ORGANISM: Artificial
<220> FEATURE:
<223> OTHER INFORMATION: Aminoacyl tRNA synthetase  for the
      incorporation of p-azido-phenylalanine

<400> SEQUENCE: 18

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
```

```
                195                 200                 205
Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
    290                 295                 300

Arg Leu
305

<210> SEQ ID NO 19
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-acetyl-phenylalanine

<400> SEQUENCE: 19

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
```

```
                    245                 250                 255
Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 20
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-acetyl-phenylalanine

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
```

```
                     290                 295                 300

Arg Leu
305

<210> SEQ ID NO 21
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-acetyl-phenylalanine

<400> SEQUENCE: 21

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 22
<211> LENGTH: 306
<212> TYPE: PRT
```

<213> ORGANISM: Artificial
<220> FEATURE:
<223> OTHER INFORMATION: Aminoacyl tRNA synthetase for the
      incorporation of p-azido-phenylalanine

<400> SEQUENCE: 22

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 23
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 23

Met Asp Glu Phe Glu Met Ile Lys Arg Asn Thr Ser Glu Ile Ile Ser
1               5                   10                  15

```
Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
290                 295                 300

Arg Leu
305

<210> SEQ ID NO 24
<211> LENGTH: 306
<212> TYPE: PRT
<213> ORGANISM: Artificial
<220> FEATURE:
<223> OTHER INFORMATION: Mutant synthetase derived from Methanococcus
      jannaschii synthetase

<400> SEQUENCE: 24

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Val
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60
```

-continued

```
Tyr Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu His Gly Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

MODIFIED INTERFERON BETA POLYPEPTIDES AND THEIR USES

CROSS REFERENCE TO RELATED APPLICATIONS

This application is a divisional of U.S. application Ser. No. 12/112,890 filed on Apr. 30, 2008 now U.S. Pat. No. 8,114,630, which is incorporated by reference herein in its entirety and claims the benefit of priority to U.S. Provisional Patent Application 60/927,528 filed May 2, 2007, the specification and disclosure of which is incorporated herein in its entirety for all purposes.

FIELD OF THE INVENTION

This invention relates to interferon beta polypeptides optionally modified with at least one non-naturally-encoded amino acid.

BACKGROUND OF THE INVENTION

Interferons (IFNs) are a well-known family of cytokines secreted by a large variety of eukaryotic cells. Interferons have a variety of biological activities, including anti-viral, immunomodulatory, immunoregulatory, neoplastic, and anti-proliferative properties, and have been utilized as therapeutic agents for treatment of diseases such as cancer, and various viral diseases. Interferons have demonstrated utility in the treatment of a variety of diseases, and are in widespread use for the treatment of multiple sclerosis and viral hepatitis; the most common therapeutic applications are currently treatment of hepatitis C and multiple sclerosis. Interferons are members of the growth hormone (GH) supergene family (Bazan, F. *Immunology Today* 11: 350-354 (1990); Mott, H. R. and Campbell, I. D. *Current Opinion in Structural Biology* 5: 114-121 (1995); Silvennoinen, O. and Ihle, J. N. (1996) SIGNALING BY THE HEMATOPOIETIC CYTOKINE RECEPTORS) which represents a set of proteins with similar structural characteristics. Each member of this family of proteins comprises a four helical bundle. While there are still more members of the family yet to be identified, some members of the family include the following: growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, epsilon interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). Members of the GH supergene family have similar secondary and tertiary structures, despite the fact that they generally have limited amino acid or DNA sequence identity. The shared structural features allow new members of the gene family to be readily identified. Four helical bundle and interferon polypeptides are described in WO 2005/074650 entitled "Modified Human Four Helical Bundle Polypeptides and Their Uses," WO 2005/074524 entitled "Modified Human Interferon Polypeptides and Their Uses," WO 2006/133089 and WO 2006/133088 entitled "Improved Human Interferon Polypeptides and Their Uses," which are all incorporated by reference herein in their entirety.

Interferons include a number of related proteins, such as interferon-alpha (IFN-α), interferon-beta (IFN-β), interferon-gamma IFN-γ) interferon-kappa (IFN-κ, also known as interferon-epsilon or IFN-ε), interferon-tau (IFN-τ), and interferon-omega (IFN-ω). These interferon proteins are produced in a variety of cell types: IFN-α (leukocytes), IFN-β (fibroblasts), IFN-γ (lymphocytes), IFN-ε or κ (keratinocytes), IFN-ω (leukocytes) and IFN-τ (trophoblasts). IFN-α, IFN-β, IFN-ε or κ, IFN-ω, and IFN-τ are classified as type I interferons, while IFN-γ is classified as a type II interferon. Interferon alpha is encoded by a multi-gene family, while the other interferons appear to each be coded by a single gene in the human genome. Furthermore, there is some allelic variation in interferon sequences among different members of the human population.

Interferons are relatively small, single-chain glycoproteins released by cells invaded by viruses or exposed to certain other substances. Interferons are presently grouped into three major classes, designated: 1) leukocyte interferon (interferon-alpha, α-interferon, IFN-α), 2) fibroblast interferon (interferon-beta, β-interferon, IFN-β), and 3) immune interferon (interferon-gamma, γ-interferon, IFN-γ). In response to viral infection, lymphocytes synthesize primarily α-interferon (with omega interferon, IFN-ω), while infection of fibroblasts usually induces production of β-interferon. IFNα and IFNβ share about 20-30 percent amino acid sequence homology. The gene for human IFN-β lacks introns, and encodes a protein possessing 29% amino acid sequence identity with human IFN-α, suggesting that IFN-α and IFN-β genes have evolved from a common ancestor (Taniguchi et al., Nature 285 547-549 (1980)). By contrast, IFN-γ is synthesized by lymphocytes in response to mitogens. Pestka et al. in Annu. Rev. Immunol. (2004) 22:929-79, which is incorporated by reference herein in its entirety, describes class 2 α-helical cytokines including interferons (IFN-α, -β, -ε, -κ, -ω, -δ, -τ, and -γ) as well as interferon-like molecules such as limitin, IL-28A, IL-28B, and IL-29 as well as the ligands, receptors, and signal transduction pathways employed by these molecules. The interferons have different species and many allelic variants. In additional, interferons with novel activities and mutant sequences have been isolated from cells from patients with various diseases.

Interferons were originally derived from naturally occurring sources, such as buffy coat leukocytes and fibroblast cells, optionally using inducing agents to increase interferon production. Interferons have also been produced by recombinant DNA technology. The cloning and expression of mature IFNβ is described by Goeddel et al., *Nucleic Acids Res.* 8, 4057 (1980).

Type-I interferons all appear to bind a common receptor, type I IFN-R, composed of IFNAR1 and IFNAR2 subunits. The exact binding mode and downstream signal transduction cascades differ somewhat among the type I interferons. However, in general, the JAK/STAT signal transduction pathway is activated following binding of interferon to the interferon receptor. STAT transcription factors then translocate to the nucleus, leading to the expression of a number of proteins with antiviral, antineoplastic, and immunomodulatory activities.

The properties of naturally occurring type I interferon proteins are not optimal for therapeutic use. Type I interferons induce injection site reactions and a number of other side effects. They are highly immunogenic, eliciting neutralizing and non-neutralizing antibodies in a significant fraction of patients. Interferons are poorly absorbed from the subcutaneous injection site and have short serum half-lives. Finally, type I interferons do not express solubly in prokaryotic hosts, thus necessitating more costly and difficult refolding or mammalian expression protocols.

Specific examples of commercially available IFN products include IFNγ-1b (ACTIMMUNE®), IFNβ-1a (AVONEX®, and REBIF®), IFNβ-1b (BETASERON®), IFN alfacon-1 (INFERGEN®), IFNα-2 (INTRONA®), IFNα-2a (ROFERON-A®), Peginterferon alfa-2a (PEGASYS®), and Peginterferon alfa-2b (PEG-INTRON®). Some of the problems associated with the production of PEGylated versions of IFN proteins are described in Wang et al. (2002) Adv. Drug Deliv. Rev. 54:547-570; and Pedder, S. C. Semin Liver Dis. 2003; 23 Suppl 1:19-22. Wang et al. characterized positional isomers of PEG-INTRON®, and Pedder et al. compared PEGASYS® with PEG-INTRON® describing the lability of the PEGylation chemistries used and effects upon formulation. PEGASYS® is comprised of nine identifiable isoforms, which specific isoforms differing in anti-viral activity (Foser et al., Pharmacogenomics J 2003; 3:312). Despite the number of IFN products currently available on the market, there is still an unmet need for interferon therapeutics. The present invention is directed to identification of interferon proteins with improved properties. A number of groups have generated modified interferons with improved properties; the references below are all expressly incorporated by reference in their entirety.

Cysteine-depleted variants have been generated to minimize formation of unwanted inter- or intra-molecular disulfide bonds (U.S. Pat. Nos. 4,518,584; 4,588,585; and 4,959,314, which are incorporated by reference in their entirety). Methionine-depleted variants have been generated to minimize susceptibility to oxidation (EPO 260350, which is incorporated by reference herein).

Interferons with modified activity have been generated (U.S. Pat. Nos. 6,514,729; 4,738,844; 4,738,845; 4,753,795; 4,766,106; WO 00/78266, which are incorporated by reference herein). U.S. Pat. Nos. 5,545,723 and 6,127,332, which are incorporated by reference herein, disclose substitution mutants of interferon beta at position 101. Chimeric interferons comprising sequences from one or more interferons have been made (Chang et. al. Nature Biotech. 17: 793-797 (1999), U.S. Pat. Nos. 4,758,428; 4,885,166; 5,382,657; 5,738,846, which are incorporated by reference). Substitution mutations to interferon beta at positions 49 and 51 have also been described (U.S. Pat. No. 6,531,122, which is incorporated by reference). Expression and generation of IFN beta variants and conjugates have been disclosed in U.S. Pat. Nos. 7,144,574 and 6,531,111, which are incorporated by reference herein in their entirety. Modifications discussed included glycosylation sites that were introduced into IFN beta or removed from the polypeptide, substitutions near glycosylation sites, conjugation to lysine or cysteine residues, and introduction or removal of amino acids.

Interferon beta variants with enhanced stability have been discussed, in which the hydrophobic core was optimized using rational design methods (WO 00/68387, which is incorporated by reference). Alternate formulations that promote interferon stability or solubility have also been disclosed (U.S. Pat. Nos. 4,675,483; 5,730,969; 5,766,582; WO 02/38170, which are incorporated by reference).

Interferon beta muteins with enhanced solubility have been discussed, in which several leucine and phenylalanine residues are replaced with serine, threonine, or tyrosine residues (WO 98/48018, which is incorporated by reference). Other modifications to improve solubility are discussed in US 2005/0054053 which is incorporated by reference herein in its entirety.

Interferon alpha and interferon beta variants with reduced immunogenicity have been discussed (See WO 02/085941 and WO 02/074783, which are incorporated by reference).

Immunogenicity is a major limitation of current interferon (including but not limited to, interferon beta) therapeutics. Although immune responses are typically most severe for non-human proteins, even therapeutics based on human proteins, such as interferon beta, are often observed to be immunogenic. Immunogenicity is a complex series of responses to a substance that is perceived as foreign and may include production of neutralizing and non-neutralizing antibodies, formation of immune complexes, complement activation, mast cell activation, inflammation, and anaphylaxis. A number of patients develop neutralizing antibodies to IFN beta (Int. Arch. Allergy Immunol. 118:368 371, 1999). It has been shown that development of IFN beta-neutralizing antibodies decreases the biological response to IFN beta, and causes a trend towards decreased treatment effect (Neurol. 50:1266 1272, 1998). Neutralizing antibodies will likely also impede the therapeutic utility of IFN beta in connection with treatment of other diseases (Immunol. Immuther. 39:263 268, 1994).

Several factors can contribute to protein immunogenicity, including but not limited to the protein sequence, the route and frequency of administration, and the patient population. Aggregation has been linked to the immunogenicity of a related protein therapeutic, interferon alpha [Braun et. al. Pharm. Res. 1997 14: 1472-1478]. Another study suggests that the presence of DR15 MHC alleles increases susceptibility to neutralizing antibody formation; interestingly, the same alleles also confer susceptibility to multiple sclerosis [Stickler et. al. Genes Immun. 2004 5: 1-7].

As aggregation may contribute to the immunogenicity of interferons (particularly interferon beta), variants engineered for improved solubility may also possess reduced immunogenicity. Cysteine-depleted variants have been generated to minimize formation of unwanted inter- or intra-molecular disulfide bonds (U.S. Pat. Nos. 4,518,584; 4,588,585; 4,959,314, which are incorporated by reference); such variants show a reduced propensity for aggregation. Interferon beta variants with enhanced stability have been made, in which the hydrophobic core was optimized using rational design methods (WO 00/68387, which is incorporated by reference); in some cases solubility may be enhanced by improvements in stability. Alternate formulations that promote interferon stability and solubility have also been disclosed (U.S. Pat. Nos. 4,675,483; 5,730,969; 5,766,582; WO 02/38170, which are incorporated by reference). Interferon beta muteins with enhanced solubility have been discussed, in which several leucine and phenylalanine residues are replaced with serine, threonine, or tyrosine residues (WO 98/48018, which is incorporated by reference).

Interferons have been modified by the addition of polyethylene glycol ("PEG") (see U.S. Pat. Nos. 4,917,888; 5,382,657; and 6,962,978; WO 99/55377; WO 02/09766; WO 00/23114, all of which are incorporated by reference in their entirety). PEG addition can improve serum half-life and solubility. In some cases, PEGylation has been observed to reduce the fraction of patients who raise neutralizing antibodies by sterically blocking access to antibody agretopes (see for example, Hershfield et. al. PNAS 1991 88:7185-7189 (1991); Bailon. et al. Bioconjug. Chem. 12: 195-202 (2001); He et al. Life Sci. 65: 355-368 (1999)).

Interferon beta variants have also been generated that are predicted to bind class II MHC alleles with decreased affinity relative to the wild type protein; in both examples primarily alanine mutations were used to confer decreased binding [WO 02/074783, which is incorporated by reference; Stickler supra]. Immunoreactivity of antibodies against synthetic peptides corresponding to portions of IFN beta have been discussed in Redlich et al. Proc. Natl. Acad. Sci. (1991) 88:4040-4044.

Several methods have been developed to modulate the immunogenicity of proteins; a preferred approach is to disrupt T-cell activation by removing MHC-binding agretopes. This approach is more tractable than evading T-cell receptor or antibody binding, as the diversity of MHC molecules comprises only ~$10^3$ alleles, while the antibody repertoire is estimated to be approximately $10^8$ and the T-cell receptor repertoire is larger still. By identifying and removing or modifying class II MHC-binding peptides within a protein sequence, the molecular basis of immunogenicity can be evaded. The elimination of such agretopes for the purpose of generating less immunogenic proteins has been disclosed previously; see for example WO 98/52976 and WO 02/079232, which are incorporated by reference.

While a large number of mutations in MHC-binding agretopes may be identified that are predicted to confer reduced immunogenicity, most of these amino acid substitutions will be energetically unfavorable. As a result, the vast majority of the reduced immunogenicity sequences identified using the methods described above will be incompatible with the structure and/or function of the protein. In order for MHC agretope removal to be a viable approach for reducing immunogenicity, it is crucial that simultaneous efforts are made to maintain a protein's structure, stability, and biological activity.

Immunogenicity may limit the efficacy and safety of interferon therapeutics in multiple ways. Therapeutic efficacy may be reduced directly by the formation of neutralizing antibodies. Efficacy may also be reduced indirectly, as binding to either neutralizing or non-neutralizing antibodies may alter serum half-life. Unwanted immune responses may take the form of injection site reactions, including but not limited to delayed-type hypersensitivity reactions. It is also possible that anti-interferon beta neutralizing antibodies may cross-react with endogenous interferon beta and block its function.

There remains a need for novel interferon proteins having reduced immunogenicity. Variants of interferon with reduced immunogenicity could find use in the treatment of a number of interferon responsive conditions. U.S. Patent Publication No. 2005/0054053, which is incorporated by reference herein, describes variant IFN beta proteins with modulated immunogenicity as compared with wild-type IFN beta.

As a result, there exists a need for the development and discovery of interferon proteins with improved properties, including but not limited to increased efficacy, decreased side effects, decreased immunogenicity, increased solubility, and enhanced soluble prokaryotic expression. There is a need for interferon polypeptides that require less frequent injection and/or result in decreased risk of developing neutralizing antibodies. Improved interferon therapeutics could may be useful for the treatment of a variety of diseases and conditions, including autoimmune diseases, viral infections, and, inflammatory diseases, cell proliferation diseases, bacterial infections, enhancing fertility, and cancer, among others and transplant rejection. In addition, interferons may be used to promote the establishment of pregnancy in certain mammals.

The use of human interferon beta, one member of the interferon family, is best established in the treatment of multiple sclerosis. Two forms of recombinant interferon beta, have recently been licensed in Europe and the U.S. for treatment of this disease. One form is interferon-beta-1a (trademarked and sold as AVONEX®, mfg. Biogen, Inc., Cambridge, Mass.; or as REBIF®, mfg. Merck Serono) and hereinafter, "interferon-beta-1a" or "IFN-beta-1a" or "IFN-β-1a" or "interferon-β-1a", or in various hyphenated and unhyphenated forms, used interchangeably. A currently marketed formulation of AVONEX® has 30 ug/dose (200 MIU/mg) and provides CHO-derived (Chinese Hamster Ovary) IFN-beta 1a given intramuscularly four times per week. A currently marketed formulation of REBIF® has 44 μg/dose (270 MIU/mg) given subcutanelous TIW and also provides CHO-derived IFN beta 1a. The other form is interferon-beta-1b (trademarked and sold as BETASERON® Berlex, Richmond, Calif.), hereinafter, "interferon-beta-1b". A currently marketed formulation of BETASERON® has 250 μg/dose (32 MIU/mg) and provides *E. Coli*-derived IFN-beta 1b given subcutaneously every other day or three times daily. Interferon beta-1a is produced in mammalian cells using the natural human gene sequence and is glycosylated, whereas interferon beta-1b is produced in *E. coli* bacteria using a modified human gene sequence that contains a genetically engineered cysteine-to-serine substitution at amino acid position 17 (C17S) and is non-glycosylated. Common side effects include, but are not limited to, fever, headaches, fatigue, anxiety, depression, liver disorders, and injection site reactions. Yong et al. Neurology (1998) 51:682-689 discuss the use of interferon beta in the treatment of multiple sclerosis and indicate the accumulation rate of disability from MS is reduced.

The crystal structure of glycosylated human interferon beta has been described by Karpusas et al. in Proc Natl. Acad Sci 1997 94:11813-11818. This protein is glycosylated at a single site (Asn80). The protein has a tendency to aggregate when produced in *E. coli* (Mitsui et al. Pharmacol Ther 1993 58:93-132). Karpusas et al. describe the production of human interferon beta in Chinese hamster ovary cells (CHO) and purification of the secreted protein using blue Sepharose and SP-Sepharose (ion exchange).

Alpha and beta interferons have been used in the treatment of the acute viral disease herpes zoster (T. C. Merigan et al, N. Engl. J. Med. 298, 981-987 (1978); E. Heidemann et al., Onkologie 7, 210-212 (1984)), chronic viral infections, e.g. hepatitis C and hepatitis B infections (R. L. Knobler et al., Neurology 34(10): 1273-9 (1984); M. A. Faerkkilae et al., Act. Neurol. Sci. 69, 184-185 (1985)).

Human IFNβ is a regulatory polypeptide with a molecular weight of about 22 kDa consisting of 166 amino acid residues. It can be produced by most cells in the body, in particular fibroblasts, in response to viral infection or exposure to other agents. It binds to a multimeric cell surface receptor, and productive receptor binding results in a cascade of intracellular events leading to the expression of IFNβ inducible genes which in turn produces effects which can be classified as anti-viral, anti-proliferative and immunomodulatory.

The amino acid sequence of human IFNβ is known (Taniguchi, Gene 10:11-15, 1980, and in EP 83069, EP 41313 and U.S. Pat. No. 4,686,191 which are incorporated by reference herein). Human and murine IFNβ crystal structures have been described in Proc. Natl. Acad. Sci. USA 94:11813-11818, 1997; J. Mol. Biol. 253:187-207, 1995; U.S. Pat. No. 5,602,232; 5,460,956; 5,441,734; 4,672,108; which are incorporated by reference herein and discussed in Cell Mol. Life. Sci. 54:1203-1206, 1998. Variants of IFMβ have been reported (WO 95/25170, WO 98/48018, U.S. Pat. No. 6,572,853, U.S. Pat. No. 5,545,723, U.S. Pat. No. 4,914,033, EP 260350, U.S. Pat. No. 4,588,585, U.S. Pat. No. 4,769,233, Stewart et al, DNA Vol. 6 no. 2 1987 pp. 119-128, Runkel et al, 1998, J. Biol. Chem. 273, No. 14, pp. 8003-8008, which are incorporated by reference herein). U.S. Pat. No. 4,966,843, U.S. Pat. No. 5,376,567, U.S. Pat. No. 5,795,779, U.S. Pat. No. 7,144,574, which are incorporated by reference herein, describe the expression of IFNβ in CHO cells. IFNβ molecules with a particular glycosylation pattern and methods for their preparation have been reported (EP 287075 and EP 529300).

The structure and function of IFNβ1a and β1b have been compared in Pharmaceut. Res. 15:641-649, 1998. The progression of multiple sclerosis has been shown to be delayed with IFN beta. Multiple sclerosis is a relapsing then progressive inflammatory degenerative disease of the central nervous system. Other effects that IFNβ may have include, but are not limited to, inhibitory effects on the proliferation of leukocytes and antigen presentation, modulation of the profile of cytokine production towards an anti-inflammatory phenotype, and reduction of T-cell migration by inhibiting the activity of T-cell matrix metalloproteases to account for the mechanism of IFNβ in MS (Neurol. 51:682-689, 1998).

IFN beta may be used in the treatment of a number of diseases including, but not limited to, osteosarcoma, basal cell carcinoma, cervical dysplasia, glioma, acute myeloid leukemia, multiple myeloma, Hodgkin's disease, breast carcinoma, melanoma, and viral infections, including but not limited to, papilloma virus, viral hepatitis, herpes genitalis, herpes zoster, herpetic keratitis, herpes simplex, viral encephalitis, cytomegalovirus pneumonia, and rhinovirus. Side effects of current IFNβ therapeutics include injection site reactions, fever, chills, myalgias, arthralgias, and other flu-like symptoms (Clin. Therapeutics, 19:883-893, 1997).

An improved IFNβ-like molecule is needed, considering the multitude of side effects with current IFNβ products, their association with frequent injection, the risk of developing neutralizing antibodies impeding the desired therapeutic effect of IFNβ, and the potential for obtaining more optimal therapeutic IFNβ levels with concomitant enhanced therapeutic effect.

The relative in vitro potencies of interferon-beta-1a and interferon beta 1b in functional assays have been compared, and it was shown that the specific activity of interferon-beta-1a is approximately 10-fold greater than the specific activity of interferon-beta-1b (Runkel et al., 1998, Pharm. Res. 15: 641-649). From studies designed to identify the structural basis for these activity differences, glycosylation was identified as the only one of the known structural differences between the products that affected the specific activity. The effect of the carbohydrate was largely manifested through its stabilizing role on structure. The stabilizing effect of the carbohydrate was evident in thermal denaturation experiments and SEC analysis. Lack of glycosylation was also correlated with an increase in aggregation and an increased sensitivity to thermal denaturation. Enzymatic removal of the carbohydrate from interferon-beta-1a with PNGase F caused extensive precipitation of the deglycosylated product.

Interferon-beta molecules of the invention may retain all or most of their biological activities and the following properties may result: altered pharmacokinetics and pharmacodynamics leading to increased half-life and alterations in tissue distribution (e.g., ability to stay in the vasculature for longer periods of time), increased stability in solution, reduced immunogenicity, protection from proteolytic digestion and subsequent abolition of activity. Such molecules would be a substantial advance in the pharmaceutical and medical arts and would make a significant contribution to the management of various diseases in which interferon has some utility, such as multiple sclerosis, fibrosis, and other inflammatory or autoimmune diseases, cancers, hepatitis and other viral diseases. In particular, the ability to remain for longer periods of time in the vasculature allows the interferon beta to be used to inhibit angiogenesis and potentially to cross the blood-brain barrier. Conjugates formed between interferon beta comprising a non-naturally encoded amino acid and another molecule, including but not limited to a polymer, could result in modulated thermal stability of the conjugate. Such modulated thermal stability may be an advantage when formulating interferon-beta in powder form for use in subsequent administration via inhalation.

Covalent attachment of the hydrophilic polymer poly(ethylene glycol), abbreviated PEG, is a method of increasing water solubility, bio availability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where bio compatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.,* 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as $—(NH—CHR—CO)_n—$, where the subscript "n" can equal hundreds or thousands. The fragment represented by R can contain reactive sites for protein biological activity and for attachment of PEG derivatives.

For example, in the case of the amino acid lysine, there exists an $—NH_2$ moiety in the epsilon position as well as in the alpha position. The epsilon $—NH_2$ is free for reaction under conditions of basic pH. Much of the art in the field of protein derivatization with PEG has been directed to developing PEG derivatives for attachment to the epsilon $—NH_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon —$NH_2$ can also react with —N(H)—. Similarly, the side chain of the amino acid cysteine bears a free sulfhydryl group, represented structurally as —SH. In some instances, the PEG derivatives directed at the epsilon —$NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the —$NH_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-genetically encoded amino acids to proteins in vivo. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A.* 99:11020-11024; and, Chin, J. W., et al., (2002) *J. Am. Chem. Soc.* 124:9026-9027), keto amino acids, heavy atom containing amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *Chem Bio Chem* 3(11):1135-1137; J. W. Chin, et al., (2002), *PNAS United States of America* 99:11020-11024; and, L. Wang, & P. G. Schultz, (2002), *Chem. Comm.*, 1:1-11. All references are incorporated by reference in their entirety. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tornoe, et al., (2002) *J. Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of IFN beta polypeptides, and also addresses the production of a IFN beta polypeptide with improved biological or pharmacological properties, such as enhanced antiviral activity and/or improved therapeutic half-life.

SUMMARY OF THE INVENTION

This invention provides IFN beta polypeptides comprising one or more non-naturally encoded amino acids.

In some embodiments, the IFN beta polypeptide comprises one or more post-translational modifications. In some embodiments, the IFN beta polypeptide is linked to a linker, polymer, or biologically active molecule. In some embodiments, the IFN beta polypeptide is linked to a bifunctional polymer, bifunctional linker, or at least one additional IFN beta polypeptide. In some embodiments, the IFN beta polypeptide comprises one or more post-translational modifications to the C17S mutant form of IFN beta.

In some embodiments, the non-naturally encoded amino acid is linked to a water soluble polymer. In some embodiments, the water soluble polymer comprises a poly(ethylene glycol) moiety. In some embodiments, the non-naturally encoded amino acid is linked to the water soluble polymer with a linker or is bonded to the water soluble polymer. In some embodiments, the poly(ethylene glycol) molecule is a bifunctional polymer. In some embodiments, the bifunctional polymer is linked to a second polypeptide. In some embodiments, the second polypeptide is a IFN beta polypeptide. The present invention also includes each of the above embodiments in addition to the C17S mutation in IFN beta.

In some embodiments, the IFN beta polypeptide comprises at least two amino acids linked to a water soluble polymer comprising a poly(ethylene glycol) moiety. In some embodiments, at least one amino acid is a non-naturally encoded amino acid. In some embodiments, the IFN beta polypeptide comprising at least two amino acids linked to a water soluble polymer comprising a poly(ethylene glycol) moiety includes the C17S mutation, in other embodiments any mutation at position 17 is included in addition to one or more non-naturally encoded amino acids in an IFN beta polypeptide.

In some embodiments, one or more non-naturally encoded amino acids are incorporated in one or more of the following positions in IFN beta: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4). In some embodiments one of these incorporations occurs at position 17.

In some embodiments, one or more non-naturally encoded amino acids are incorporated at any position in one or more of the following regions corresponding to secondary structures in interferon beta as follows: Helix A (2-22); Helix B (51-71); Helix C (80-107); Helix D (118-136); Helix E (139-162); AB loop: AB1 (23-35); AB2 (36-40); AB3 (41-50) from SEQ ID NO: 1 or the corresponding amino acids of SEQ ID NOs: 3, 4. In other embodiments, the non-naturally encoded amino acid is substituted at a position selected from the group consisting of residues 25-35, 80-100, and 121-135 of interferon beta (SEQ ID NO: 1 or the corresponding amino acids from SEQ ID NO: 3, 4). In other embodiments, the non-naturally encoded amino acid is substituted at a position selected from the group consisting of residues 41-49 from interferon beta from SEQ ID NO: 1 or the corresponding amino acids from SEQ ID NO: 3, 4. In some embodiments, one or more non-naturally encoded amino acids are incorporated at one or more of the following positions of IFN beta: 28, 36, 76, 80, 107, 108, 111, 8, 15, 19, 36, 42, 46, 48, 49, 80, 108, 111, 113, 155, and any combination thereof (SEQ ID NO: 1 or the corresponding amino acids in SEQ ID NOs: 3, 4). In some embodiments, one or more non-naturally encoded amino acids are incorporated at one or more of the following positions of IFN beta: 28, 36, 76, 80, 107, 108, 111, and any combination thereof of SEQ ID NO: 1 or the corresponding amino acids in SEQ ID NOs: 3, 4. In some embodiments, one or more non-naturally encoded amino acids are incorporated at one or more of the following positions of IFN beta: 8, 15, 19, 36, 42, 46, 48, 49, 80, 108, 111, 113, 155, and any combination thereof of SEQ ID NO: 1 or the corresponding amino acids in SEQ ID NOs: 3, 4. In some embodiments, one or more non-naturally encoded amino acids are incorporated at one or more of the following positions of IFN beta: 15, 42, 80, 108, 111, 155, and any combination thereof of SEQ ID NO: 1 or the corresponding amino acids in SEQ ID NOs: 3, 4). In some embodiments, one or more non-naturally encoded amino acids are incorporated at one or more of the following positions of IFN beta: 36, 111 of SEQ ID NO: 1 or the corresponding amino acids in SEQ ID NOs: 3, 4). In some embodiments, the polypeptide of the invention comprises one or more natural amino acid substitution, addition, or deletion. In some embodiments, the polypeptide of the invention comprises a C17S substitution (serine for a cysteine at position 17) of SEQ ID NO: 1 or the corresponding amino acids in SEQ ID NO: 3, 4. In some embodiments, the polypeptide of the invention comprises a C17S substitution (serine for a cysteine at position 17) and one or more natural amino acid substitution, addition, or deletion. In some embodiments, the polypeptide of the invention comprises one or more non-naturally encoded amino acid substitution, addition, or deletion in the signal sequence. In some embodiments, the polypeptide of the invention comprises one or more non-naturally encoded amino acid substitution, addition, or deletion in the signal sequence of SEQ ID NO: 4. In some embodiments, the polypeptide of the invention comprises one or more naturally encoded amino acid substitution, addition, or deletion in the signal sequence of SEQ ID NO: 4. In some embodiments, one or more non-natural amino acids are incorporated in the leader or signal sequence of SEQ ID NOs: 4 or other IFN beta sequence. The present invention also includes each of the above embodiments in addition to the C17S mutation in IFN beta.

In some embodiments, the non-naturally occurring amino acid at one or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4 or the corresponding amino acids in another IFN beta sequence).

In some embodiments, the non-naturally occurring amino acid in one or more of these regions is linked to a water soluble polymer, including but not limited to: Helix A (2-22); Helix B (51-71); Helix C (80-107); Helix D (118-136); Helix E (139-162); AB loop: AB1 (23-35); AB2 (36-40); AB3 (41-50) from SEQ ID NO: 1 or the corresponding amino acids of SEQ ID NOs: 3, 4. In other embodiments, the non-naturally occurring amino acid in one or more of these regions is linked to a water soluble polymer, including but not limited to, residues 25-35, 80-100, and 121-135 of interferon beta (SEQ ID NO: 1 or the corresponding amino acids from SEQ ID NO: 3, 4). In other embodiments, the non-naturally occurring amino acid in one or more of these regions is linked to a water soluble polymer, including but not limited to, residues 41-49 from interferon beta from SEQ ID NO: 1 or the corresponding amino acids from SEQ ID NO: 3, 4. In some embodiments, the non-naturally occurring amino acid at one or more of these positions is linked to a water soluble polymer, including but not limited to, positions: 28, 36, 76, 80, 107, 108, 111, 8, 15, 19, 36, 42, 46, 48, 49, 80, 108, 111, 113, 155, and any combination thereof (SEQ ID NO: 1 or the corresponding amino acids in SEQ ID NOs: 3, 4). In some embodiments, the non-naturally occurring amino acid at one or more of these positions is linked to a water soluble polymer, including but not limited to, positions: 28, 36, 76, 80, 107, 108, 111, and any combination thereof of SEQ ID NO: 1 or the corresponding amino acids in SEQ ID NOs: 3, 4. In some embodiments, the non-naturally occurring amino acid at one or more of these positions is linked to a water soluble polymer, including but not limited to, positions: 8, 15, 19, 36, 42, 46, 48, 49, 80, 108, 111, 113, 155, and any combination thereof of SEQ ID NO: 1 or the corresponding amino acids in SEQ ID NOs: 3, 4). In some embodiments, the non-naturally occurring amino acid at one or more of these positions is linked to a water soluble polymer, including but not limited to, positions: 15, 42, 80, 108, 111, 155, and any combination thereof of SEQ ID NO: 1 or the corresponding amino acids in SEQ ID NOs: 3, 4). In some embodiments, the non-naturally occurring amino acid at one or more of these positions is linked to a water soluble polymer, including but not limited to, positions: 36, 111 of SEQ ID NO: 1 or the corresponding amino acids in SEQ ID NOs: 3, 4). In some embodiments, the non-naturally occurring amino acid in the signal or leader sequence is linked to a water soluble polymer (SEQ ID NO: 4 or other IFN beta sequence). The present invention also includes each of the above embodiments in addition to the C17S mutation in IFN beta.

In some embodiments, the IFN beta polypeptide comprises a substitution, addition or deletion that modulates affinity of the IFN beta polypeptide for a IFN polypeptide receptor or binding partner, including but not limited to, a protein, polypeptide, small molecule, or nucleic acid. In some embodiments, the IFN beta polypeptide comprises a substitution, addition, or deletion that increases the stability of the IFN beta polypeptide when compared with the stability of the corresponding IFN beta without the substitution, addition, or deletion. Stability and/or solubility may be measured using a number of different assays known to those of ordinary skill in the art. Such assays include but are not limited to SE-HPLC and RP-HPLC. In some embodiments, the IFN beta polypeptide comprises a substitution, addition, or deletion that modulates the immunogenicity of the IFN beta polypeptide when compared with the immunogenicity of the corresponding IFN beta without the substitution, addition, or deletion. In some embodiments, the IFN beta polypeptide comprises a substitution, addition, or deletion that modulates serum half-life or circulation time of the IFN beta polypeptide when compared with the serum half-life or circulation time of the corresponding IFN beta without the substitution, addition, or deletion.

In some embodiments, the IFN beta polypeptide comprises a substitution, addition, or deletion that increases the aqueous solubility of the IFN beta polypeptide when compared to aqueous solubility of the corresponding IFN beta without the substitution, addition, or deletion. In some embodiments, the IFN beta polypeptide comprises a substitution, addition, or deletion that increases the solubility of the IFN beta polypeptide produced in a host cell when compared to the solubility of the corresponding IFN beta without the substitution, addition, or deletion. In some embodiments, the IFN beta polypeptide comprises a substitution, addition, or deletion that increases the expression of the IFN beta polypeptide in a host cell or increases synthesis in vitro when compared to the expression or synthesis of the corresponding IFN beta without the substitution, addition, or deletion. The IFN beta polypeptide comprising this substitution retains agonist activity and retains or improves expression levels in a host cell. In some embodiments, the IFN beta polypeptide comprises a substitution, addition, or deletion that increases protease resistance of the IFN beta polypeptide when compared to the protease resistance of the corresponding IFN beta without the substitution, addition, or deletion. In some embodiments, the IFN beta polypeptide comprises a substitution, addition, or deletion that modulates signal transduction activity of the IFN receptor when compared with the activity of the receptor upon interaction with the corresponding IFN beta polypeptide without the substitution, addition, or deletion. In some embodiments, the IFN beta polypeptide comprises a substitution, addition, or deletion that modulates its binding to another molecule such as a receptor when compared to the binding of the corresponding IFN beta polypeptide without the substitution, addition, or deletion. In some embodiments, the IFN beta polypeptide comprises a substitution, addition, or deletion that modulates its anti-viral activity compared to the anti-viral activity of the corresponding IFN beta polypeptide without the substitution, addition, or deletion. In some embodiments, the IFN beta polypeptide comprises a substitution, addition, or deletion that enhances its anti-viral activity compared to the anti-viral activity of the corresponding IFN beta polypeptide without the substitution, addition, or deletion.

In some embodiments, the IFN beta polypeptide comprises a substitution, addition, or deletion that increases compatibility of the IFN beta polypeptide with pharmaceutical preservatives (e.g., m-cresol, phenol, benzyl alcohol) when compared to compatibility of the corresponding IFN beta without the substitution, addition, or deletion. This increased compatibility would enable the preparation of a preserved pharmaceutical formulation that maintains the physiochemical properties and biological activity of the protein during storage.

In some embodiments, one or more engineered bonds are created with one or more non-natural amino acids. The intramolecular bond may be created in many ways, including but not limited to, a reaction between two amino acids in the protein under suitable conditions (one or both amino acids may be a non-natural amino acid); a reaction with two amino acids, each of which may be naturally encoded or non-naturally encoded, with a linker, polymer, or other molecule under suitable conditions; etc.

In some embodiments, one or more amino acid substitutions in the IFN beta polypeptide may be with one or more naturally occurring or non-naturally occurring amino acids. In some embodiments the amino acid substitutions in the IFN beta polypeptide may be with naturally occurring or non-naturally occurring amino acids, provided that at least one substitution is with a non-naturally encoded amino acid. In some embodiments, one or more amino acid substitutions in the IFN beta polypeptide may be with one or more naturally occurring amino acids, and additionally at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

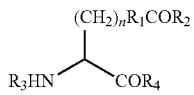

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

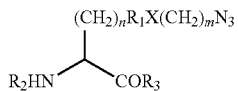

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

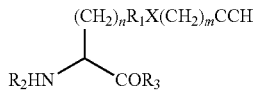

wherein n is 0-10; $R_1$ is an alkyl, aryl, substituted alkyl, or substituted aryl; X is O, N, S or not present; in is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is a IFN beta polypeptide agonist, partial agonist, antagonist, partial antagonist, or inverse agonist. In some embodiments, the IFN beta polypeptide agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the IFN beta polypeptide agonist, partial agonist, antagonist, partial antagonist, or inverse agonist comprises a non-naturally encoded amino acid and one or more post-translational modification, linker, polymer, or biologically active molecule.

The present invention also provides isolated nucleic acids comprising a polynucleotide that hybridizes under stringent conditions to SEQ ID NO: 2 or nucleic acids that encode polypeptides of SEQ ID NOs: 3, 4. The present invention also provides isolated nucleic acids comprising a polynucleotide that hybridizes under stringent conditions to SEQ ID NO: 2 or polynucleotides that hybridize under stringent conditions to polynucleotides that encode polypeptides shown as SEQ ID NOs: 3, 4 wherein the polynucleotide comprises at least one selector codon. The present invention also provides isolated nucleic acids comprising a polynucleotide that encodes the polypeptides shown as SEQ ID NOs.: 1, 3, 4. The present invention also provides isolated nucleic acids comprising a polynucleotide that encodes the polypeptides shown as SEQ ID NOs.: 1, 3, 4, with one or more non-naturally encoded amino acids. It is readily apparent to those of ordinary skill in the art that a number of different polynucleotides can encode any polypeptide of the present invention.

In some embodiments, the selector codon is selected from the group consisting of an amber codon, ochre codon, opal codon, a unique codon, a rare codon, a five-base codon, and a four-base codon.

The present invention also provides methods of making a IFN beta polypeptide linked to a water soluble polymer. In some embodiments, the method comprises contacting an isolated IFN beta polypeptide comprising a non-naturally encoded amino acid with a water soluble polymer comprising a moiety that reacts with the non-naturally encoded amino acid, In some embodiments, the non-naturally encoded amino acid incorporated into the IFN beta polypeptide is reactive toward a water soluble polymer that is otherwise unreactive toward any of the 20 common amino acids. In some embodiments, the non-naturally encoded amino acid incorporated into the IFN beta polypeptide is reactive toward a linker, polymer, or biologically active molecule that is otherwise unreactive toward any of the 20 common amino acids.

In some embodiments, the IFN beta polypeptide linked to the water soluble polymer is made by reacting a IFN beta polypeptide comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage. In some embodiments, the aminooxy, hydrazine, hydrazide or semicarbazide group is linked to the poly(ethylene glycol) molecule through a carbamate linkage.

In some embodiments, the IFN beta polypeptide linked to the water soluble polymer is made by reacting a poly(ethylene glycol) molecule comprising a carbonyl group with a polypeptide comprising a non-naturally encoded amino acid that comprises an aminooxy, hydrazine, hydrazide or semicarbazide group.

In some embodiments, the IFN beta polypeptide linked to the water soluble polymer is made by reacting a IFN beta polypeptide comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the IFN beta polypeptide linked to the water soluble polymer is made by reacting a IFN beta polypeptide comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to the IFN beta polypeptide comprises a polyalkylene glycol moiety. In some embodiments, the non-naturally encoded amino acid residue incorporated into the IFN beta polypeptide comprises a carbonyl group, an aminooxy group, a hydrazide group, a hydrazine, a semicarbazide group, an azide group, or an alkyne group. In some embodiments, the non-naturally encoded amino acid residue incorporated into the IFN beta polypeptide comprises a carbonyl moiety and the water soluble polymer comprises an aminooxy, hydrazide, hydrazine, or semicarbazide moiety. In some embodiments, the non-naturally encoded amino acid residue incorporated into the IFN beta polypeptide comprises an alkyne moiety and the water soluble polymer comprises an azide moiety. In some embodiments, the non-naturally encoded amino acid residue incorporated into the IFN beta polypeptide comprises an azide moiety and the water soluble polymer comprises an alkyne moiety.

The present invention also provides compositions comprising a IFN beta polypeptide comprising a non-naturally encoded amino acid and a pharmaceutically acceptable carrier. In some embodiments, the non-naturally encoded amino acid is linked to a water soluble polymer.

The present invention also provides cells comprising a polynucleotide encoding the IFN beta polypeptide comprising a selector codon. In some embodiments, the cells comprise an orthogonal RNA synthetase and/or an orthogonal tRNA for substituting a non-naturally encoded amino acid into the IFN beta polypeptide.

The present invention also provides methods of making a IFN beta polypeptide comprising a non-naturally encoded amino acid. In some embodiments, the methods comprise culturing cells comprising a polynucleotide or polynucleotides encoding a IFN beta polypeptide, an orthogonal RNA synthetase and/or an orthogonal tRNA under conditions to permit expression of the IFN beta polypeptide; and purifying the IFN beta polypeptide from the cells and/or culture medium.

The present invention also provides methods of increasing therapeutic half-life, serum half-life or circulation time of IFN beta polypeptides. The present invention also provides methods of modulating immunogenicity of IFN beta polypeptides. In some embodiments, the methods comprise substituting a non-naturally encoded amino acid for any one or more amino acids in naturally occurring IFN beta polypeptides and/or linking the IFN beta polypeptide to a linker, a polymer, a water soluble polymer, or a biologically active molecule.

The present invention also provides methods of treating a patient in need of such treatment with an effective amount of a IFN beta molecule of the present invention. In some embodiments, the methods comprise administering to the patient a therapeutically-effective amount of a pharmaceutical composition comprising a IFN beta polypeptide comprising a non-naturally-encoded amino acid and a pharmaceutically acceptable carrier. In some embodiments, the non-naturally encoded amino acid is linked to a water soluble polymer. In some embodiments, the IFN beta polypeptide is glycosylated. In some embodiments, the IFN beta polypeptide is not glycosylated.

The present invention also provides IFN beta polypeptides comprising a sequence shown in SEQ ID NO: 1, 3, 4, or any other IFN beta polypeptide sequence, except that at least one amino acid is substituted by a non-naturally encoded amino acid. The present invention also provides IFN beta polypeptides comprising a sequence shown as SEQ ID NO: 1, 3, 4. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a IFN beta polypeptide comprising the sequence shown in SEQ ID NO: 1, 3, 4, or any other IFN beta polypeptide sequence, wherein at least one amino acid is substituted by a non-naturally encoded amino acid. The present invention also provides pharmaceutical compositions comprising a pharmaceutically acceptable carrier and a IFN beta polypeptide comprising the sequence shown in SEQ ID NO: 1, 3, 4. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the IFN beta polypeptide via a saccharide moiety.

The present invention also provides a IFN beta polypeptide comprising a water soluble polymer linked by a covalent bond to the IFN beta polypeptide at a single amino acid. In some embodiments, the water soluble polymer comprises a poly(ethylene glycol) moiety. In some embodiments, the amino acid covalently linked to the water soluble polymer is a non-naturally encoded amino acid present in the polypeptide.

The present invention provides a IFN beta polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the polypeptide is monoPEGylated. The present invention also provides a IFN beta polypeptide comprising a linker, polymer, or biologically active molecule that is attached to one or more non-naturally encoded amino acid wherein said non-naturally encoded amino acid is ribosomally incorporated into the polypeptide at pre-selected sites.

Included within the scope of this invention is the IFN beta leader or signal sequence joined to an IFN beta coding region, as well as a heterologous signal sequence joined to an IFN beta coding region. The heterologous leader or signal sequence selected should be one that is recognized and processed, e.g. by host cell secretion system to secrete and possibly cleaved by a signal peptidase, by the host cell. A method of treating a condition or disorder with the IFN beta of the present invention is meant to imply treating with IFN beta with or without a signal or leader peptide.

The present invention also provides methods of inducing an increase in anti-viral activity in cells, said method comprising administering IFN beta to said cells in an amount effective to induce an increase in anti-viral activity.

In another embodiment, conjugation of the IFN beta polypeptide comprising one or more non-naturally occurring amino acids to another molecule, including but not limited to PEG, provides substantially purified IFN beta due to the unique chemical reaction utilized for conjugation to the non-natural amino acid. Conjugation of IFN beta comprising one or more non-naturally encoded amino acids to another molecule, such as PEG, may be performed with other purification techniques performed prior to or following the conjugation step to provide substantially pure IFN beta.

BRIEF DESCRIPTION OF THE DRAWINGS

FIG. 6A—A graph of pharmacokinetic data from Example 27, 3 µg/kg dose level group, showing serum IFN beta concentration measured in ng/mL over time elapsed in hours.

FIG. 6B—A graph of pharmacokinetic data from Example 27, 15 µg/kg dose level group, showing serum IFN beta concentration measured in ng/mL over time elapsed in hours.

FIG. 7A—A graph of pharmacokinetic data from Example 27, 50 µg/kg dose level group, showing serum IFN beta concentration measured in ng/mL over time elapsed in hours.

FIG. 7B—A graph of pharmacokinetic data from Example 27 from the M36-30K treated animals and the REBIF® controls, showing serum IFN beta concentration measured in ng/mL over time elapsed in hours.

FIG. 8A—A graph of pharmacokinetic data from Example 27 from the M36-40K treated animals and the REBIF® controls, showing serum IFN beta concentration measured in ng/mL over time elapsed in hours.

FIG. 8B—A graph of pharmacokinetic data from Example 27 from the F111-30K treated animals and the REBIF® controls, showing serum IFN beta concentration measured in ng/mL over time elapsed in hours.

FIG. 9A—A graph of pharmacokinetic data from Example 27 from the F111-40K treated animals and the REBIF® controls, showing serum IFN beta concentration measured in ng/mL over time elapsed in hours.

FIG. 9B—A graph of data from Example 27 showing Cmax of some IFN beta variants of the present invention against a control (Serum IFNbeta Cmax/Dose).

FIG. 10A—A graph of area under the curve (AUC) data from Example 27 showing AUC of some IFN beta variants of the present invention against a control (Serum IFN AUC/Dose).

FIG. 10B—A bar graph of data from Example 27 showing serum IFN beta concentrations at 168 hours following dosing with two different IFN beta variants of the present invention at different dosage levels and a control.

FIG. 11A—A graph of data from Example 27 showing Neopterin response of some IFN beta variants of the present invention at the 3 µg/kg dose group against placebo and a control (Serum Neopterin/Time).

FIG. 11B—A graph of data from Example 27 showing Neopterin response of some IFN beta variants of the present invention at the 15 µg/kg dose group against placebo and a control (Serum Neopterin/Time).

FIG. 12A—A graph of data from Example 27 showing Neopterin response of some IFN beta variants of the present invention at the 50 µg/kg dose group against placebo and a control (Serum Neopterin/Time).

FIG. 12B—A graph of data from Example 27 showing area under the curve measurements for serum neopterin versus dose for some IFN beta variants of the present invention against placebo and a control (Serum Neopterin AUC/Dose).

FIG. 15A—A graph showing serum IFN beta a1 levels as measured by antiviral activity (filled symbols and solid lines on graph) and neopterin concentrations (open symbols and dashed lines on graph) in rhesus monkeys following intravenous administration.

FIG. 15B—A graph showing serum IFN beta a1 levels as measured by antiviral activity (filled symbols and solid lines on graph) and neopterin concentrations (open symbols and dashed lines on graph) in rhesus monkeys following subcutaneous administration.

FIG. 15C—A graph showing antiviral activity of unmodified and pegylated IFN beta 1a assessed in antiviral assays using human lung carcinoma (A549) cells challenged with EMC virus. Following 2-day incubation with virus, viable cells were stained with XTT, the plates were read at 450 nm, and the absorbance, which is reflective of cell viability, is shown on the y-axis. Samples were analyzed in duplicate.

FIG. 16A—A graph of data from Example 27 showing the fold induction vs. pre-dosing with vehicle, REBIF®, and four different IFN beta variants at the 3 µg/kg dose level of the present invention of OAS 1 gene expression against time.

FIG. 16B—A graph of data from Example 27 showing the fold induction vs. pre-dosing with vehicle, REBIF®, and an average of the 3 different dose levels of four IFN beta variants of the present invention of OAS1 gene expression against time.

FIG. 17A—A graph of data from Example 27 showing the fold induction vs. pre-dosing with vehicle, REBIF®, and four different IFN beta variants at the 15 µg/kg dose level of the present invention of OAS1 gene expression against time.

FIG. 17B—A graph of data from Example 27 showing the fold induction vs. pre-dosing with vehicle, REBIF®, and four different IFN beta variants at the 50 µg/kg dose level of the present invention of OAS1 gene expression against time.

FIG. 20—A table of data collected in Example 27 for each different treatment group—N.S. indicating not significant.

FIG. 21—A table of data collected in Example 27 for each different treatment group—N.S. indicating not significant.

DEFINITIONS

Figure 1:
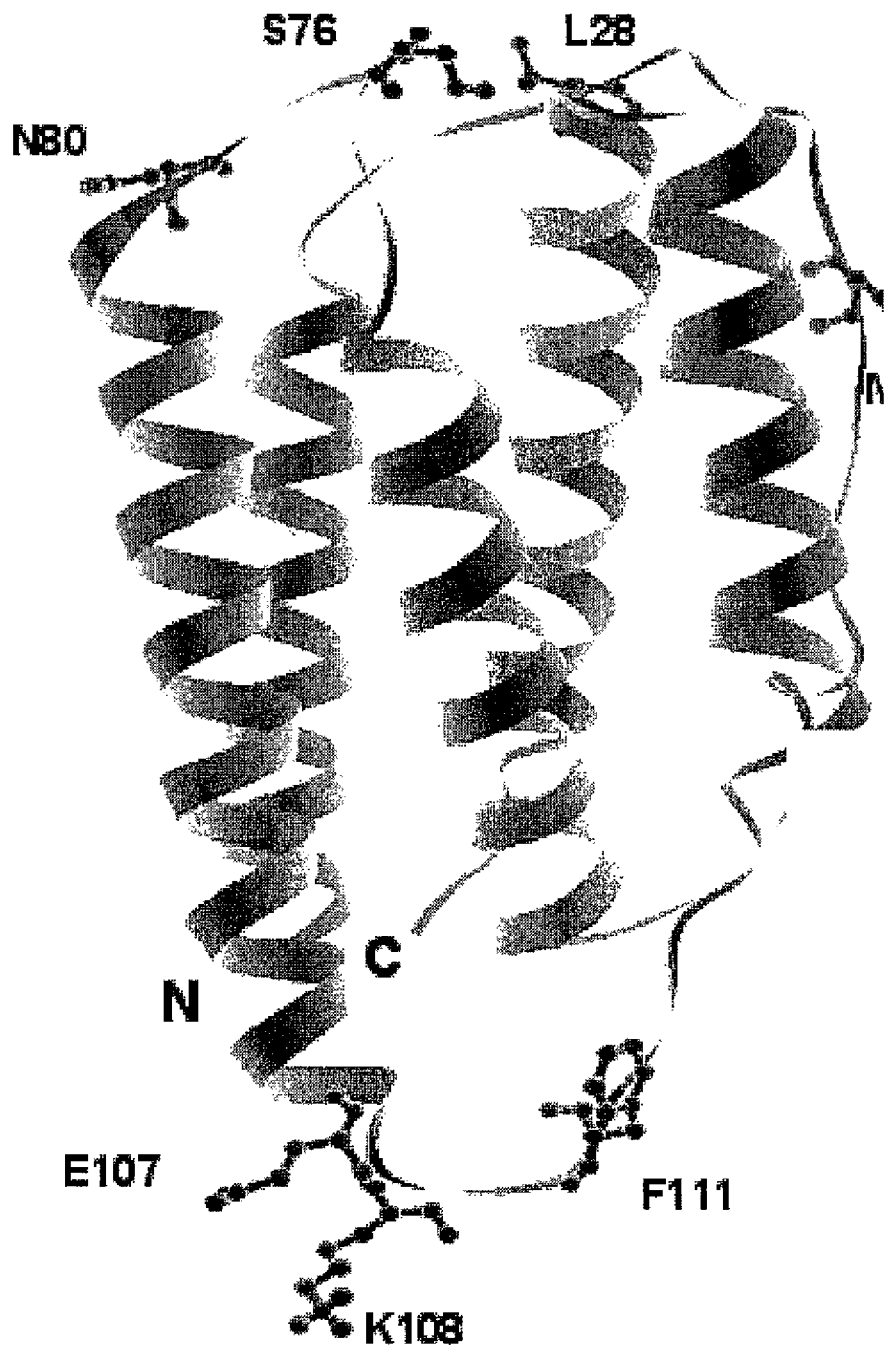
FIG. 1—A model of the crystal structure of IFN beta is shown. Each of the sites shown were substituted with a non-naturally encoded amino acid.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "IFN beta," "IFNβ," or "IFN beta polypeptide" and various hyphenated and unhyphenated forms is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to an IFN beta polypeptide that may be substantially or essentially free of components that normally accompany or interact with the protein as found in its naturally occurring environment, i.e. a native cell, or host cell in the case of recombinantly produced IFN beta polypeptides. IFN beta polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the IFN beta polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the IFN beta polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" IFN beta polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the IFN beta polypeptide has been secreted, including medium either before or after a proliferation step. The term also may encompass buffers or reagents that contain host cell lysates, such as in the case where the IFN beta polypeptide is produced intracellularly and the host cells are lysed or disrupted to release the IFN beta polypeptide.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used herein with respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

As used herein, "IFN beta polypeptide," "IFN beta" or "IFNβ" and hyphenated and unhyphenated forms thereof shall include those polypeptides and proteins that have at least one biological activity of a IFN beta, as well as 1a and 1b forms, a and b forms, IFN beta analogs, IFN beta isoforms, IFN beta mimetics, IFN beta fragments, hybrid IFN beta proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. The term "IFN beta polypeptide," "IFNβ," and "IFN beta" encompass IFN beta polypeptides comprising one or more amino acid substitutions, additions or deletions.

As used herein, "interferon" or "IFN" shall include those polypeptides and proteins that have at least one biological activity of an interferon, including but not limited to IFNα, IFNβ, IFNγ, IFNω, IFNε, or IFNτ or interferon-like cytokines such as limitin (such as those described in U.S. Pat. Nos. 4,414,150; 4,456,748; 4,727,138; 4,762,791; 4,929,554; 5,096,705; 4,695,623; 4,614,651; 4,678,751; 4,925,793; 5,460,811; 5,120,832; 4,780,530; 4,908,432; 4,970,161; 4,973,479; 4,975,276; 5,098,703; 5,278,286; 5,661,009; 6,372,206; 6,433,144; 6,472,512; 6,572,853; 6,703,225; 6,200,780; 6,299,869; 6,300,475; 6,323,006; 6,350,589; 5,705,363; 5,738,845; 5,789,551; 6,117,423; 6,174,996; 5,540,923; 5,541,293; 5,541,312; 5,554,513; 5,593,667 which are incorporated by reference herein), as well as IFN analogs, IFN isoforms, IFN mimetics, IFN fragments, hybrid IFN proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. Specific examples of IFN include, but are not limited to, IFNγ-1b (Actimmune), IFNβ-1a (AVONEX®, and REBIF®), IFNβ-1b (BETASERON®), consensus IFN, IFN alfacon-1 (INFERGEN®), IFNα-2 (INTRON A®), IFNα-2a (ROFERON-A®), Peginterferon alfa-2a (PEGASYS®), Peginterferon alfa-2b (PEG-INTRON®), IFN analog, IFN mutants, altered glycosylated human IFN, and PEG conjugated IFN analogs. Specific examples of cells modified for expression of endogenous human IFN are described in Devlin et al., J. Leukoc. Biol. 41:306 (1987); U.S. Pat. Nos. 6,610,830; 6,482,613; 6,489,144; 6,159,712; 5,814,485; 5,710,027; 5,595,888; 4,966,843; which are incorporated by reference herein. See also, U.S. Pat. Nos. 6,716,606; 6,379,661; 6,004,548; 5,830,705; 5,582,823; 4,810,643; and 6,242,218, which are incorporated by reference herein, for expression of GH family members.

Substitutions in a wide variety of amino acid positions in IFN beta have been described. Substitutions including but not limited to, those that modulate pharmaceutical stability, increase agonist activity, increase protease resistance, convert the polypeptide into an antagonist, etc. and are encompassed by the term "IFN beta polypeptide" or "IFN β." IFN beta polypeptides comprising one or more amino acid substitutions have been described in U.S. Patent Publication No. 2005/0054053. IFN-β variants exhibiting modified immunogenicity comprising at least one modification at a position selected from the group consisting of 1, 2, 3, 4, 5, 6, 8, 9, 12, 15, 16, 22, 28, 30, 32, 36, 42, 43, 46, 47, 48, 49, 51, 92, 93, 96, 100, 101, 104, 111, 113, 116, 117, 120, 121, 124, 130, 148, and 155 were described. The modifications to residues 5, 8, 15, 47, 111, 116, and 120 may be substitution mutations that are selected from the group consisting of alanine, arginine, aspartic acid, asparagine, glutamic acid, glutamine, glycine, histidine, and lysine. Modifications to residues 22, 28, 30, 32, 36, 92, 130, 148, and 155 may be selected from the group including alanine, arginine, aspartic acid, asparagine, glutamic acid, glutamine, glycine, histidine, serine, threonine and lysine. These variants were described to have increased solubility leading to reduced immunogenicity. One modification selected from the group consisting of: L5A, L5D, L5E, L5K, L5N, L5Q, L5R, L5S, L5T, F8A, F8D, F8E, F8K, F8N, F8Q, F8R, F8S, S12E, S12K, S12Q, S12R, W22E, L28Q, Y30H, L32A, E43K, E43R, L47K, Y92Q, E104R, E104K, E104H, E104Q, E104A, F111N, R113D, R113E, R113Q, R113A, L116D, L116E, L116N, L116Q, L116R, M117R, L120D, L120R, L130R, V148A, and Y155S may be present in a polypeptide of the invention. An IFN beta polypeptide of the invention may comprise one or more natural amino acid substitution. The C17S substitution has been described previously. U.S. Patent No. 2005/0054053 describes IFN beta variants with a L5Q substitution in addition to the C17S substitution (SEQ ID NO:19 of U.S. Patent No. 2005/0054053), with a L5Q and F8E substitution in addition to the C17S substitution (SEQ ID NO:20 of U.S. Patent No. 2005/0054053), with a L5Q, F8E, and F111N substitution in addition to the C17S substitution (SEQ ID NO:21 of U.S. Patent No. 2005/0054053), with a L5Q, F8E, and L116E substitution in addition to the C17S substitution (SEQ ID NO:22 of U.S. Patent No. 2005/0054053), with a F8E, F111N, and L116E substitution in addition to the C17S substitution (SEQ ID NO:23 of U.S. Patent No. 2005/0054053), with a L5Q, F8E, F111N, and L116E substitution in addition to the C17S substitution (SEQ ID NO:24 of U.S. Patent No. 2005/0054053) and with a L5Q, F8E, L47K, F111N, L116E, and L120R substitution in addition to the C17S substitution (SEQ ID NO: 25 of U.S. Patent No. 2005/0054053

In a further aspect, variant IFN beta, proteins with reduced immunogenicity exhibit reduced binding at least one human class II MHC allele. In this embodiment (as well as for other modified immunogenicity variants) at least one amino acid modification may be made in at least one of the following positions: agretope 1: residues 3-11; agretope 2: residues 5-13; agretope 3: residues 8-16; agretope 4: residues 9-17; agretope 5: residues 15-23; agretope 6: residues 22-30; agretope 7: residues 30-38; agretope 8: residues 36-44; agretope 9: residues 47-55; agretope 10: residues 57-65; agretope 11: residues 60-68; agretope 12: residues 63-71; agretope 13: residues 70-78; agretope 14: residues 79-87; agretope 15: residues 95-103; agretope 16: residues 122-130; agretope 17: residues 125-133; agretope 18: residues 129-137; agretope 19: residues 130-138; agretope 20: residues 143-151; agretope 21: residues 145-153; agretope 22: residues 146-154; agretope 23: residues 148-156; agretope 24: residues 151-159; agretope 25: residues 154-162; agretope 26: residues 156-164; agretope 27: residues 157-165. Variants also include amino acid modifications in 2 or more of these agretopes.

In a further aspect, the invention provides recombinant nucleic acids encoding the variant proteins, expression vectors containing the variant nucleic acids, host cells comprising the variant nucleic acids and/or expression vectors, and methods for producing the variant proteins. In an additional aspect, the invention provides treating an interferon responsive disorder by administering to a patient a variant protein, usually with a pharmaceutical carrier, in a therapeutically effective amount. In a further aspect, the invention provides methods for modulating immunogenicity (particularly reducing immunogenicity) of interferons (particularly IFN beta) by altering MHC Class II epitopes.

IFN beta mutants discussed in U.S. Pat. No. 7,144,574, which is incorporated by reference in its entirety, include polypeptides comprising one or more of the following modifications: D110F; C17S; Q49N; Q51T; F111N; R113T; K19R; K33R; K45R; Q51S; R113S; Q48F; Q48V; Q48W; Q48Y; D110V; D110W; D110Y that are glycosylated or not glycosylated. WO 2005/016371, which is incorporated by reference herein, describe a IFN beta-1b polypeptide that is selectively oxidized. Other mutants include, but are not limited to, an analog comprising native interferon-beta in which asparagine at position 25 is deamidated (see WO 2006/053134) and those with different glycosylation as described in WO 2006/049423, both of which are incorporated by reference herein. Codon optimization for *E. coli* expression of IFN beta is described in WO 2006/015165, which is incorporated by reference herein.

For sequences of IFN beta that lack a leader sequence, see SEQ ID NO: 1 and 3 herein. For a sequence of IFN beta with a leader sequence, see SEQ ID NO: 4 herein. In some embodiments, IFN beta polypeptides of the invention are substantially identical to SEQ ID NOs: 1, 3, 4, or any other sequence of a IFN beta polypeptide. Nucleic acid molecules encoding IFN beta polypeptides including mutants and methods to express and purify IFN beta polypeptides are well known and include, but are not limited to, those disclosed in U.S. Pat. No. 4,462,940; U.S. Pat. No. 4,518,584; U.S. Pat. No. 5,702,699; U.S. Pat. No. 6,962,978; U.S. Pat. No. 5,814,485; U.S. Pat. No. 6,887,462; U.S. Pat. No. 6,800,735; U.S. Pat. No. 6,514,729; U.S. Publication Nos. US2002/0137895, US2004/0115169, and US2005/0054053, which are incorporated by reference in their entirety herein.

The term "IFN beta polypeptide" also includes the pharmaceutically acceptable salts and prodrugs, and prodrugs of the salts, polymorphs, hydrates, solvates, biologically-active fragments, biologically active variants and stereoisomers of the naturally-occurring IFN beta as well as agonist, mimetic, and antagonist variants of the naturally-occurring IFN beta and polypeptide fusions thereof. Fusions comprising additional amino acids at the amino terminus, carboxyl terminus, or both, are encompassed by the term "IFN beta polypeptide." Exemplary fusions include, but are not limited to, e.g., methionyl IFN beta in which a methionine is linked to the N-terminus of IFN beta resulting from the recombinant expression of the mature form of IFN beta lacking the leader or signal peptide or portion thereof (a methionine is linked to the N-terminus of IFN beta resulting from the recombinant expression), fusions for the purpose of purification (including, but not limited to, to poly-histidine or affinity epitopes), fusions with serum albumin binding peptides and fusions with serum proteins such as serum albumin. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13. Chimeric molecules comprising IFN beta and one or more other molecules. The chimeric molecule can contain specific regions or fragments of one or both of the IFN beta and the other molecule(s). Any such fragments can be prepared from the proteins by standard biochemical methods, or by expressing a polynucleotide encoding the fragment. IFN beta, or a fragment thereof, can be produced as a fusion protein comprising human serum albumin (HSA), Fc, or a portion thereof. Such fusion constructs are suitable for enhancing expression of the IFN beta, or fragment thereof, in a eukaryotic host cell. Exemplary HSA portions include the N-terminal polypeptide (amino acids 1-369, 1-419, and intermediate lengths starting with amino acid 1), as disclosed in U.S. Pat. No. 5,766,883, and publication WO 97/24445, which are incorporated by reference herein. Other chimeric polypeptides can include a HSA protein with IFN beta, or fragments thereof, attached to each of the C-terminal and N-terminal ends of the HSA. Such HSA constructs are disclosed in U.S. Pat. No. 5,876,969, which is incorporated by reference herein. Other fusions may be created by fusion of interferon beta with a) the Fc portion of an immunoglobulin; b) an analog of the Fc portion of an immunoglobulin; and c) fragments of the Fc portion of an immunoglobulin. US Patent Publication No. 2005/0054053 describes circularly permuted interferon beta and fusions of IFN beta with an immunoglobulin or a region of an immunoglobulin.

Various references disclose modification of polypeptides by polymer conjugation or glycosylation. The term "IFN beta polypeptide" includes polypeptides conjugated to a polymer such as PEG and may be comprised of one or more additional derivitizations of cysteine, lysine, or other residues. In addition, the IFN beta polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Polymer modification of native IFNβ or a C17S variant thereof has been reported (EP 229108, U.S. Pat. No. 5,382, 657; EP 593868; U.S. Pat. No. 4,917,888 and WO 99/55377, which are incorporated by reference herein). Polymer conjugates of interferon-beta-1a have also been described in U.S. Pat. No. 6,962,978, which is incorporated by reference herein. Interferons comprising one or more non-naturally encoded amino acid have been described in U.S. Patent Publication No. US 2005/0220762; WO 2006/133089; and WO 2006/133088, which are incorporated by reference herein in their entirety. Basu et al. in Bioconjugate Chem 2006 17:618-630 evaluated the stability, solubility, aggregation, immunogenicity, and pharmacokinetic properties of over 20 site-selective mono-PEGylated or multi-PEGylated interferon-beta-1b polypeptides. The conjugates were formed at lysine residues or at the N-terminus.

Examples of PEGylated IFN molecules include those disclosed in U.S. Pat. Nos. 6,524,570; 6,250,469; 6,180,096; 6,177,074; 6,042,822; 5,981,709; 5,951,974; 5,908,621; 5,738,846; 5,711,944; 5,382,657, which are incorporated by reference herein. IFNβ is mentioned as one example of a polypeptide belonging to the growth hormone superfamily. WO 00/23114 discloses glycosylated and pegylated IFNβ. WO 00/23472 discloses IFNβ fusion proteins. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. IFNβ is disclosed as one example among many polypeptides that can be modified according to the technology described in U.S. Pat. No. 5,218,092, which is incorporated by reference herein. U.S. Pat. No. 5,218,092, which is incorporated by reference herein, discloses modification of granulocyte colony stimulating factor (G-CSF) and other polypeptides so as to introduce at least one additional carbohydrate chain as compared to the native polypeptide.

The term "IFN beta polypeptide" also includes glycosylated IFN beta, such as but not limited to, polypeptides glycosylated at any amino acid position, N-linked or O-linked glycosylated forms of the polypeptide. Variants containing single nucleotide changes are also considered as biologically active variants of IFN beta polypeptide. In addition, splice variants are also included. The term "IFN beta polypeptide" also includes IFN beta polypeptide heterodimers, homodimers, heteromultimers, or homomultimers of any one or more IFN beta polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

All references to amino acid positions in IFN beta described herein are based on the position in SEQ ID NO: 1, unless otherwise specified (i.e., when it is stated that the comparison is based on SEQ ID NO: 3, 4, or other IFN beta sequence). For example, the amino acid at position 1 of SEQ ID NO: 1, is a methionine and the corresponding methionine is located in SEQ ID NO: 4 at position 22. Those of skill in the art will appreciate that amino acid positions corresponding to positions in SEQ ID NO: 1 can be readily identified in any other IFN beta molecule such as SEQ ID NO: 3 and 4. Those of skill in the art will appreciate that amino acid positions corresponding to positions in SEQ ID NO: 1, 3, 4, or any other IFN beta sequence can be readily identified in any other IFN beta molecule such as IFN beta fusions, variants, fragments, etc. For example, sequence alignment programs such as BLAST can be used to align and identify a particular position in a protein that corresponds with a position in SEQ ID NO: 1, 3, 4, or other IFN beta sequence. Substitutions, deletions or additions of amino acids described herein in reference to SEQ ID NO: 1, 3, 4, or other IFN beta sequence are intended to also refer to substitutions, deletions or additions in corresponding positions in IFN beta fusions, variants, fragments, etc. described herein or known in the art and are expressly encompassed by the present invention.

The term "IFN beta polypeptide" or "IFN beta" encompasses IFN beta polypeptides comprising one or more amino acid substitutions, additions or deletions. IFN beta polypeptides of the present invention may be comprised of modifications with one or more natural amino acids in conjunction with one or more non-natural amino acid modification. Exemplary substitutions in a wide variety of amino acid positions in naturally-occurring IFN beta polypeptides have been described, including but not limited to substitutions that modulate pharmaceutical stability, that modulate one or more of the biological activities of the IFN beta polypeptide, such as but not limited to, increase agonist activity, increase solubility of the polypeptide, decrease protease susceptibility, convert the polypeptide into an antagonist, etc. and are encompassed by the term "IFN beta polypeptide." In some embodiments, the IFN beta antagonist comprises a non-naturally encoded amino acid linked to a water soluble polymer that is present in a receptor binding region of the IFN beta molecule.

In some embodiments, the IFN beta polypeptides further comprise an addition, substitution or deletion that modulates biological activity of the IFN beta polypeptide. In some embodiments, the IFN beta polypeptides further comprise an addition, substitution or deletion that modulates anti-viral activity of the IFN beta polypeptide. In some embodiments, the IFN beta polypeptides further comprise an addition, substitution or deletion that enhances anti-viral activity of the IFN beta polypeptide. For example, the additions, substitutions or deletions may modulate one or more properties or activities of IFN beta. For example, the additions, substitutions or deletions may modulate affinity for the IFN receptor, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, IFN beta polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "IFN beta polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly(ethylene glycol) or polydextran, or polypeptides of various lengths.

A "non-naturally encoded amino acid" refers to an amino acid that is not one of the common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, toxins, prokaryotic and eukaryotic cells, viruses, polysaccharides, nucleic acids and portions thereof obtained or derived from viruses, bacteria, insects, animals or any other cell or cell type, liposomes, microparticles and micelles. The IFN beta polypeptides may be added in a micellular formulation; see U.S. Pat. No. 5,833,948, which is incorporated by reference herein in its entirety. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671, 958, 4,659,839, 4,414,148, 4,699,784; 4,680,338; and 4,569, 789 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to the IFN beta and its receptor or IFN beta.

Where substituent groups are specified by their conventional chemical formulas, written from left to right, they equally encompass the chemically identical substituents that would result from writing the structure from right to left, for example, the structure $—CH_2O—$ is equivalent to the structure $—OCH_2—$.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_3$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsulfinyl, $C_1$-$C_{10}$ alkylsulfonyl, $—(CH_2)_m—O—(C_1\text{-}C_{10}$ alkyl) wherein m is from 1 to 8, aryl, substituted aryl, substituted alkoxy, fluoroalkyl, heterocyclic radical, substituted heterocyclic radical, nitroalkyl, $—NO_2$, —CN, —NRC(O)—($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, $—SO_2$, —COON, $—NR_2$, carbonyl, —C(O)—($C_1$-$C_{10}$ alkyl)-$CF_3$, —C(O)—$CF_3$, $—C(O)NR_2$, —($C_1$-$C_{10}$ aryl)-S—($C_6$-$C_{10}$ aryl), —C(O)—($C_1$-$C_{10}$ aryl), $—(CH_2)_m$, —O—(—$(CH_2)_m$—O—($C_1$-$C_{10}$ alkyl) wherein each m is from 1 to 8, $—C(O)NR_2$, $—C(S)NR_2$, $SO_2NR_2$, $—NRC(O)NR_2$, $—NRC(S)NR_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures $—CH_2CH_2—$ and $—CH_2CH_2CH_2CH_2—$, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, and $—CH{=}CH—N(CH_3)—CH_3$. Up to two heteroatoms may be consecutive, such as, for example, $—CH_2—NH—OCH_3$ and $—CH_2—O—Si(CH_3)_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to IFN beta polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water soluble polymer may or may not have its own biological activity, and may be utilized as a linker for attaching IFN beta to other substances, including but not limited to one or more IFN beta polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R'—S(O)$_2$R', —S(O)$_2$NR'R", —NRSO$_2$R', —CN and —NO$_2$ in a number ranging from zero to (2 m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to faun a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R"R'", —OC(O)R', —C(O)R', —CO$_2$R', —CONR'R", —OC(O) NR'R", —NR"C(O)R', —NR'—C(O)NR"R'", —NR"C(O)$_2$R', —NR—C(NR'R"R'")=NR"", —NR—C (NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified IFN beta relative to its non-modified form. Serum half-life is measured by taking blood samples at various time points after administration of IFN beta, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of IFN beta, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins: Structures and Molecular Properties* (WH Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) aligmnents (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus firiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the IFN beta polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc. Other protecting groups known in the art may also be used in or with the methods and compositions described herein.

By way of example only, blocking/protecting groups may be selected from:

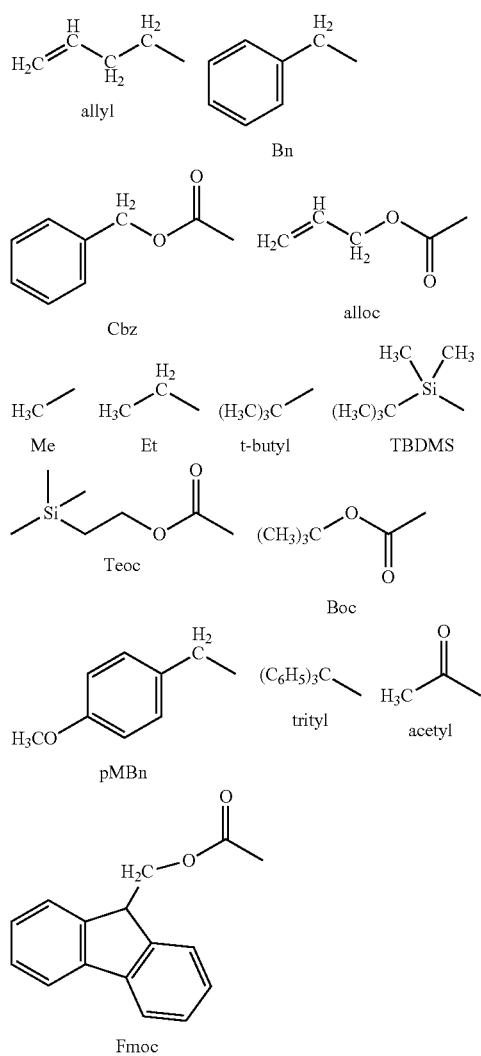

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the modified non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labelled compounds described herein, for example those into which radioactive isotopes such as $^3$H and $^{14}$C are incorporated, may be useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In some situations, non-naturally encoded amino acid polypeptides may exist as tautomers. In addition, the non-naturally encoded amino acid polypeptides described herein can exist in unsolvated as well as solvated forms with pharmaceutically acceptable solvents such as water, ethanol, and the like. The solvated forms are also considered to be disclosed herein. Those of ordinary skill in the art will recognize that some of the compounds herein can exist in several tautomeric forms. All such tautomeric forms are considered as part of the compositions described herein.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

IFN beta molecules comprising at least one unnatural amino acid are provided in the invention. In certain embodiments of the invention, the IFN beta polypeptide with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified IFN beta polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell. A linker, polymer, water soluble polymer, or other molecule may attach the molecule to the polypeptide. The molecule may be linked directly to the polypeptide.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like.

In some embodiments, the IFN beta polypeptide comprises one or more non-naturally encoded amino acids for glycosylation, acetylation, acylation, lipid-modification, palmitoylation, palmitate addition, phosphorylation, or glycolipid-linkage modification of the polypeptide. In some embodiments, the IFN beta polypeptide comprises one or more non-naturally encoded amino acids for glycosylation of the polypeptide. In some embodiments, the IFN beta polypeptide comprises one or more naturally encoded amino acids for glycosylation, acetylation, acylation, lipid-modification, palmitoylation, palmitate addition, phosphorylation, or glycolipid-linkage modification of the polypeptide. In some embodiments, the IFN beta polypeptide comprises one or more naturally encoded amino acids for glycosylation of the polypeptide.

In some embodiments, the IFN beta polypeptide comprises one or more non-naturally encoded amino acid additions and/or substitutions that enhance glycosylation of the polypeptide. In some embodiments, the IFN beta polypeptide comprises one or more deletions that enhance glycosylation of the polypeptide. In some embodiments, the IFN beta polypeptide comprises one or more non-naturally encoded amino acid additions and/or substitutions that enhance glycosylation at a different amino acid in the polypeptide. In some embodiments, the IFN beta polypeptide comprises one or more deletions that enhance glycosylation at a different amino acid in the polypeptide. In some embodiments, the IFN beta polypeptide comprises one or more non-naturally encoded amino acid additions and/or substitutions that enhance glycosylation at a non-naturally encoded amino acid in the polypeptide. In some embodiments, the IFN beta polypeptide comprises one or more non-naturally encoded amino acid additions and/or substitutions that enhance glycosylation at a naturally encoded amino acid in the polypeptide. In some embodiments, the IFN beta polypeptide comprises one or more naturally encoded amino acid additions and/or substitutions that enhance glycosylation at a different amino acid in the polypeptide. In some embodiments, the IFN beta polypeptide comprises one or more non-naturally encoded amino acid additions and/or substitutions that enhance glycosylation at a naturally encoded amino acid in the polypeptide. In some embodiments, the IFN beta polypeptide comprises one or more non-naturally encoded amino acid additions and/or substitutions that enhance glycosylation at a non-naturally encoded amino acid in the polypeptide.

In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. Any such sequence may be modified to provide a desired result with the polypeptide, including but not limited to, substituting one signal sequence with a different signal sequence, substituting a leader sequence with a different leader sequence, etc.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on IFN beta comprising at least one non-naturally encoded amino acid. Introduction of at least one non-naturally encoded amino acid into IFN beta can allow for the application of conjugation chemistries that involve specific chemical reactions, including, but not limited to, with one or more non-naturally encoded amino acids while not reacting with the commonly occurring 20 amino acids. In some embodiments, IFN beta comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in *Comprehensive Organic Synthesis*, Vol. 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) J. Org. Chem. 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more importantly, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2] cycloaddition product.

It is well established in the art that PEG can be used to modify the surfaces of biomaterials (see, e.g., U.S. Pat. No. 6,610,281; Mehvar, R., J. Pharm Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are known to those of ordinary skill in the art. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are known to those of ordinary skill in the art.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Interferon Beta

Commercial preparations of IFNβ have shown to be effective in reducing the exacerbation rate of multiple sclerosis, and more patients remain exacerbation-free for prolonged periods of time as compared with placebo-treated patients. Furthermore, the accumulation rate of disability is reduced (Neurol. 51:682-689, 1998). Three of the current products are sold under the names BETASERON® (interferon β1b, non-glycosylated, produced using recombinant bacterial cells, has a deletion of the N-terminal methionine residue and the C17S mutation), and AVONEX® and REBIF® (interferon β1a, glycosylated, produced using recombinant mammalian cells).

Additional members of the IFN family are likely to be discovered in the future. New members of the IFN family can be identified through computer-aided secondary and tertiary structure analyses of the predicted protein sequences, and by selection techniques designed to identify molecules that bind to a particular target.

Thus, the description of the IFN family is provided for illustrative purposes and by way of example only and not as a limit on the scope of the methods, compositions, strategies and techniques described herein. Further, reference to IFN beta in this application is intended to use the generic term as an example of any member of the IFN family. Thus, it is understood that the modifications and chemistries described herein with reference to IFN beta polypeptides or protein can be equally applied to any member of the IFN family, including those specifically listed herein.

III. General Recombinant Nucleic Acid Methods for Use with the Invention

In numerous embodiments of the present invention, nucleic acids encoding a IFN beta polypeptide of interest will be isolated, cloned and often altered using recombinant methods. Such embodiments are used, including but not limited to, for protein expression or during the generation of variants, derivatives, expression cassettes, or other sequences derived from a IFN beta polypeptide. In some embodiments, the sequences encoding the polypeptides of the invention are operably linked to a heterologous promoter.

A nucleotide sequence encoding a IFN beta polypeptide comprising a non-naturally encoded amino acid may be synthesized on the basis of the amino acid sequence of the parent polypeptide, including but not limited to, having the amino acid sequence shown in SEQ ID NO: 1, 3, 4 and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual (2nd Ed.)*, Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes or polynucleotides that include selector codons for production of proteins that include unnatural amino acids, orthogonal tRNAs, orthogonal synthetases, and pairs thereof.

Various types of mutagenesis are used in the invention for a variety of purposes, including but not limited to, to produce novel synthetases or tRNAs, to mutate tRNA molecules, to mutate polynucleotides encoding synthetases, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, PCT-mediated mutagenesis, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

The texts and examples found herein describe these procedures. Additional information is found in the following publications and references cited within: Ling et al., *Approaches to DNA mutagenesis: an overview*, Anal Biochem. 254(2): 157-178 (1997); Dale et al., *Oligonucleotide-directed random mutagenesis using the phosphorothioate method*, Methods Mol. Biol. 57:369-374 (1996); Smith, *In vitro mutagenesis*, Ann. Rev. Genet. 19:423-462 (1985); Botstein & Shortle, *Strategies and applications of in vitro mutagenesis*, Science 229:1193-1201 (1985); Carter, *Site-directed mutagenesis*, Biochem. J. 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection*, Proc. Natl. Acad. Sci. USA 82:488-492 (1985); Kunkel et al., *Rapid and efficient site-specific mutagenesis without phenotypic selection*, Methods in Enzymol. 154, 367-382 (1987); Bass et al., *Mutant Trp repressors with new DNA-binding specificities*, Science 242:240-245 (1988); Zoller & Smith, *Oligonucleotide-directed mutagenesis using M13-derived vectors: an efficient and general procedure for the production of point mutations in any DNA fragment*, Nucleic Acids Res. 10:6487-6500 (1982); Zoller & Smith, *Oligonucleotide-directed mutagenesis of DNA fragments cloned into M13 vectors*, Methods in Enzymol. 100:468-500 (1983); Zoller & Smith, *Oligonucleotide-directed mutagenesis: a simple method using two oligonucleotide primers and a single-stranded DNA template*, Methods in Enzymol. 154:329-350 (1987); Taylor et al., *The use of phosphorothioate-modified DNA in restriction enzyme reactions to prepare nicked DNA*, Nucl. Acids Res. 13: 8749-8764 (1985); Taylor et al., *The rapid generation of oligonucleotide-directed mutations at high frequency using phosphorothioate-modified DNA*, Nucl. Acids Res. 13: 8765-8785 (1985); Nakamaye & Eckstein, *Inhibition of restriction endonuclease Nci I cleavage by phosphorothioate groups and its application to oligonucleotide-directed mutagenesis*, Nucl. Acids Res. 14: 9679-9698 (1986); Sayers et al., *5'-3' Exonucleases in phosphorothioate-based oligonucleotide-directed mutagenesis*, Nucl. Acids Res. 16:791-802 (1988); Sayers et al., *Strand specific cleavage of phosphorothioate-containing DNA by reaction with restriction endonucleases in the presence of ethidium bromide*, (1988) Nucl. Acids Res. 16: 803-814; Kramer et al., *The gapped duplex DNA approach to oligonucleotide-directed mutation construction*, Nucl. Acids Res. 12: 9441-9456 (1984); Kramer & Fritz. *Oligonucleotide-directed construction of mutations via gapped duplex DNA*, Methods in Enzymol. 154:350-367 (1987); Kramer et al., *Improved enzymatic in vitro reactions in the gapped duplex DNA approach to oligonucleotide-directed construction of mutations*, Nucl. Acids Res. 16: 7207 (1988); Fritz et al., *Oligonucleotide-directed construction of mutations: a gapped duplex DNA procedure without enzymatic reactions in vitro*, Nucl. Acids Res. 16: 6987-6999 (1988); Kramer et al., *Different base/base mismatches are corrected with different efficiencies by the methyl-directed DNA mismatch-repair system of E. coli*, Cell 38:879-887 (1984); Carter et al., *Improved oligonucleotide site-directed mutagenesis using M13 vectors*, Nucl. Acids Res. 13: 4431-4443 (1985); Carter, *Improved oligonucleotide-directed mutagenesis using M13 vectors*, Methods in Enzymol. 154: 382-403 (1987); Eghtedarzadeh & Henikoff, *Use of oligonucleotides to generate large deletions*, Nucl. Acids Res. 14: 5115 (1986); Wells et al., *Importance of hydrogen-bond formation in stabilizing the transition state of subtilisin*, Phil. Trans. R. Soc. Lond. A 317: 415-423 (1986); Nambiar et al., *Total synthesis and cloning of a gene coding for the ribonuclease S protein*, Science 223: 1299-1301 (1984); Sakmar and Khorana, *Total synthesis and expression of a gene for the alpha-subunit of bovine rod outer segment guanine nucleotide-binding protein (transducin)*, Nucl. Acids Res. 14: 6361-6372 (1988); Wells et al., *Cassette mutagenesis: an efficient method for generation of multiple mutations at defined sites*, Gene 34:315-323 (1985); Grundström et al., *Oligonucleotide-directed mutagenesis by microscale 'shotgun' gene synthesis*, Nucl. Acids Res. 13: 3305-3316 (1985); Mandecki, *Oligonucleotide-directed double-strand break repair in plasmids of Escherichia coli: a method for site-specific mutagenesis*, Proc. Natl. Acad. Sci. USA, 83:7177-7181 (1986); Arnold, *Protein engineering for unusual environments*, Current Opinion in Biotechnology 4:450-455 (1993); Sieber, et al., Nature Biotechnology, 19:456-460 (2001); W. P. C. Stemmer, Nature 370, 389-91 (1994); and, I. A. Lorimer, I. Pastan, Nucleic Acids Res. 23, 3067-8 (1995). Additional details on many of the above methods can be found in *Methods in Enzymology* Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22(20):1859-1862, (1981) e.g., using an automated synthesizer, as described in Needham-VanDevanter et al., Nucleic Acids Res., 12:6159-6168 (1984).

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985)), infection by viral vectors, high velocity ballistic penetration by small particles with the nucleic acid either within the matrix of small beads or particles, or on the surface (Klein et al., *Nature* 327, 70-73 (1987)), and/or the like. Techniques suitable for the transfer of nucleic acid into cells in vitro include the use of liposomes, microinjection, cell fusion, DEAE-dextran, the calcium phosphate precipitation method, etc. In vivo gene transfer techniques include, but are not limited to, transfection with viral (typically retroviral) vectors and viral coat protein-liposome mediated transfection [Dzau et al., Trends in Biotechnology 11:205-210 (1993)]. In some situations it may be desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life.

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, *Gene* 8:81 (1979); Roberts, et al., *Nature*, 328:731 (1987); Schneider, E., et al., *Protein Expr. Purif.* 6(1):10-14 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the IFN beta polypeptide.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), *5'-3' Exonucleases in phosphorothioate-based oligonucleotide-directed mutagenesis. Nucleic Acids Res*, 16:791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.*, 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.*, 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology*, 20:177-182. See, also, Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases, A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121:11585-6; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods known to one of ordinary skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as a IFN beta polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

IV. Non-Naturally Encoded Amino Acids

A very wide variety of non-naturally encoded amino acids are suitable for use in the present invention. Any number of non-naturally encoded amino acids can be introduced into a IFN beta polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a IFN beta polypeptide that includes a non-naturally encoded amino acid containing an azido functional group can be reacted with a polymer (including but not limited to, polyethylene glycol) or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows (Formula I):

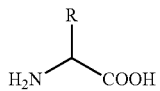

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N— or O— linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Pat. Nos. 7,045,337 and 7,083,970, which are incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

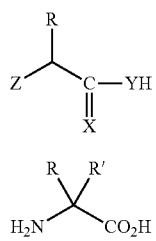

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring praline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcP-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation,* PNAS 99:19-24, which is incorporated by reference herein, for additional methionine analogs. International Application No. PCT/US06/47822 entitled "Compositions Containing, Methods Involving, and Uses of Non-natural Amino Acids and Polypeptides," which is incorporated by reference herein, describes reductive alkylation of an aromatic amine moieties, including but not limited to, p-amino-phenylalanine and reductive amination.

In one embodiment, compositions of an IFN beta polypeptide that include an unnatural amino acid (such as p-(propargyloxy)-phenyalanine) are provided. Various compositions comprising p-(propargyloxy)-phenyalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2] cycloaddition reaction.

A non-natural amino acid incorporated into a polypeptide at the amino terminus can be composed of an R group that is any substituent other than one used in the twenty natural amino acids and a $2^{nd}$ reactive group different from the NH$_2$ group normally present in α-amino acids (see Formula I). A similar non-natural amino acid can be incorporated at the carboxyl terminus with a 2$^{nd}$ reactive group different from the COOH group normally present in α-amino acids (see Formula I).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Structure and Synthesis of Non-Natural Amino Acids: Carbonyl, Carbonyl-Like, Masked Carbonyl, Protected Carbonyl Groups, and Hydroxylamine Groups In some embodiments the present invention provides IFN beta linked to a water soluble polymer, e.g., a PEG, by an oxime bond.

Many types of non-naturally encoded amino acids are suitable for formation of oxime bonds. These include, but are not limited to, non-naturally encoded amino acids containing a carbonyl, dicarbonyl, or hydroxylamine group. Such amino acids are described in U.S. Patent Publication Nos. 2006/0194256, 2006/0217532, and 2006/0217289 and WO 2006/069246 entitled "Compositions containing, methods involving, and uses of non-natural amino acids and polypeptides," which are incorporated herein by reference in their entirety. Non-naturally encoded amino acids are also described in U.S. Pat. No. 7,083,970 and U.S. Pat. No. 7,045,337, which are incorporated by reference herein in their entirety.

Some embodiments of the invention utilize IFN beta polypeptides that are substituted at one or more positions with a para-acetylphenylalanine amino acid. The synthesis of p-acetyl-(+/−)-phenylalanine and m-acetyl-(+/−)-phenylalanine are described in Zhang, Z., et al., Biochemistry 42: 6735-6746 (2003), incorporated by reference. Other carbonyl- or dicarbonyl-containing amino acids can be similarly prepared by one of ordinary skill in the art. Further, non-limiting examplary syntheses of non-natural amino acid that are included herein are presented in FIGS. 4, 24-34 and 36-39 of U.S. Pat. No. 7,083,970, which is incorporated by reference herein in its entirety.

Amino acids with an electrophilic reactive group allow for a variety of reactions to link molecules via nucleophilic addition reactions among others. Such electrophilic reactive groups include a carbonyl group (including a keto group and a dicarbonyl group), a carbonyl-like group (which has reactivity similar to a carbonyl group (including a keto group and a dicarbonyl group) and is structurally similar to a carbonyl group), a masked carbonyl group (which can be readily converted into a carbonyl group (including a keto group and a dicarbonyl group)), or a protected carbonyl group (which has reactivity similar to a carbonyl group (including a keto group and a dicarbonyl group) upon deprotection). Such amino acids include amino acids having the structure of Formula (IV):

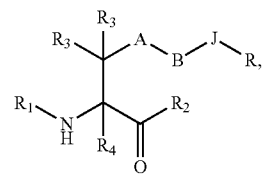

(IV)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N=, —C(R')$_2$—N=N—, and —C(R')$_2$—N(R')—N(R')—, where each R' is independently H, alkyl, or substituted alkyl;

J is

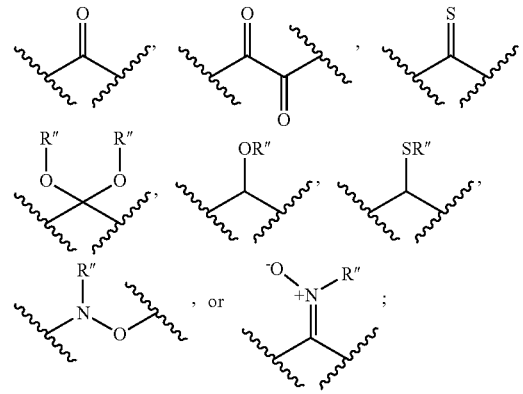

R is H, alkyl, substituted alkyl, cycloalkyl, or substituted cycloalkyl;

each R" is independently H, alkyl, substituted alkyl, or a protecting group, or when more than one R" group is present, two R" optionally form a heterocycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the —A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

or the —J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

with a proviso that when A is phenylene and each $R_3$ is H, B is present; and that when A is —$(CH_2)_4$— and each $R_3$ is H, B is not —$NHC(O)(CH_2CH_2)$—; and that when A and B are absent and each $R_3$ is H, R is not methyl.

In addition, having the structure of Formula (V) are included:

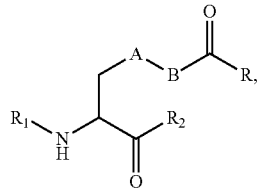

(V)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower hetero cycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_kN(R')$—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

with a proviso that when A is phenylene, B is present; and that when A is —$(CH_2)_4$—, B is not —$NHC(O)(CH_2CH_2)$—; and that when A and B are absent, R is not methyl.

In addition, amino acids having the structure of Formula (VI) are included:

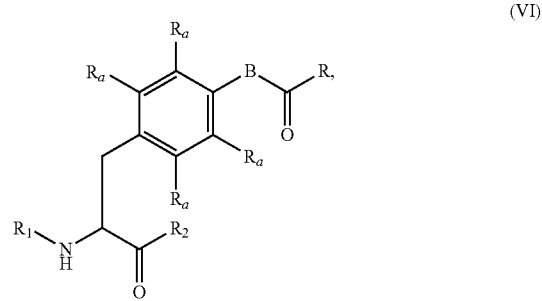

(VI)

wherein:

B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_kN(R')$—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —$N(R')_2$, —$C(O)_kR'$ where k is 1, 2, or 3, —$C(O)N(R')_2$, —OR', and —$S(O)_kR'$, where each R' is independently H, alkyl, or substituted alkyl.

In addition, the following amino acids are included:

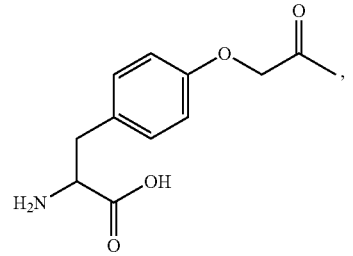

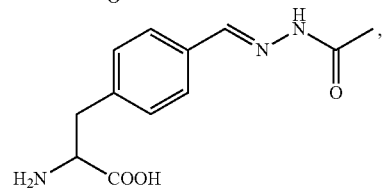

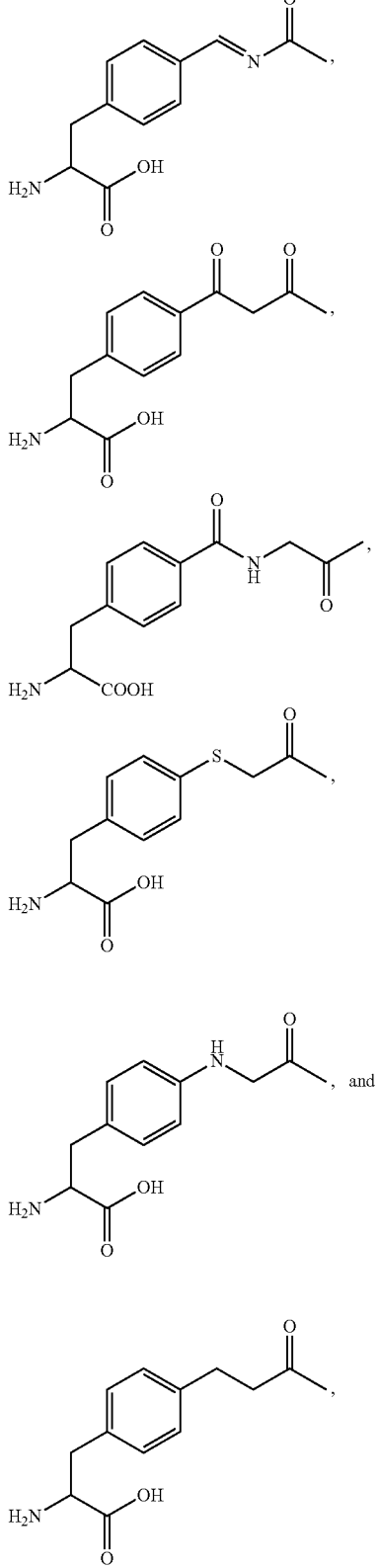

wherein such compounds are optionally amino protected group, carboxyl protected or a salt thereof. In addition, any of the following non-natural amino acids may be incorporated into a non-natural amino acid polypeptide.

In addition, the following amino acids having the structure of Formula (VII) are included:

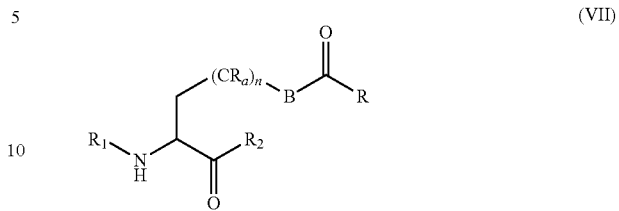

wherein
B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene), —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;
R is H, alkyl, substituted alkyl, cycloalkyl, or substituted cycloalkyl;
R$_1$ is optional, and when present, is H, an amino protecting group, resin, amino acid, polypeptide, or polynucleotide; and
R$_2$ is optional, and when present, is OH, an ester protecting group, resin, amino acid, polypeptide, or polynucleotide;
each R$_a$ is independently selected from the group consisting of H, halogen, alkyl, substituted alkyl, —N(R'), —C(O)$_k$R' where k is 1, 2, or 3, —C(O)N(R')$_2$, —OR', and —S(O)$_k$R', where each R' is independently H, alkyl, or substituted alkyl; and n is 0 to 8;
with a proviso that when A is —(CH$_2$)$_4$—, B is not —NHC(O)(CH$_2$CH$_2$)—.

In addition, the following amino acids are included:

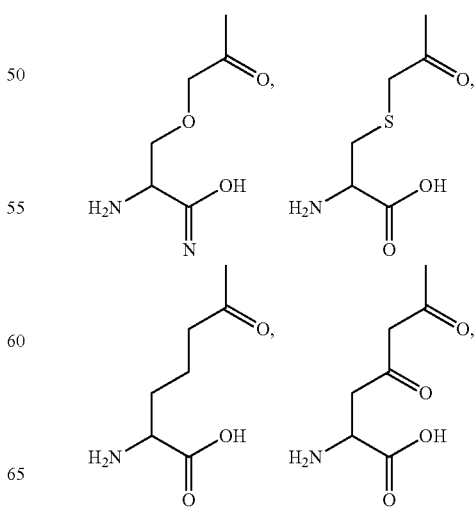

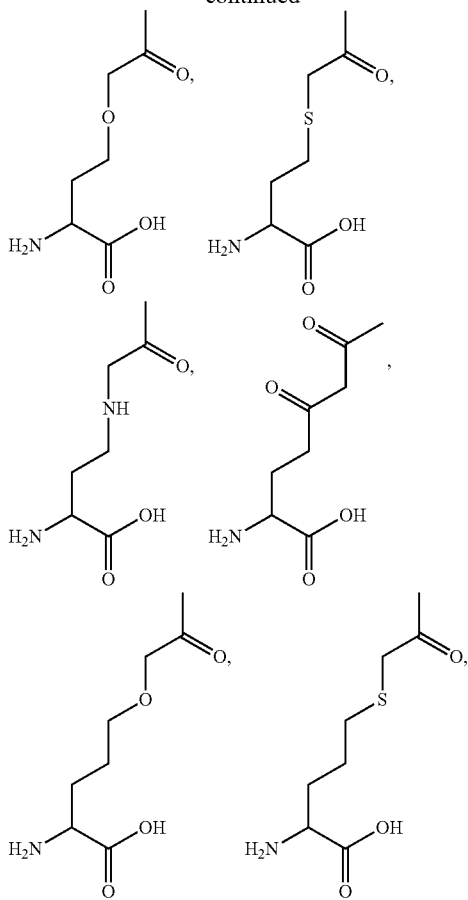

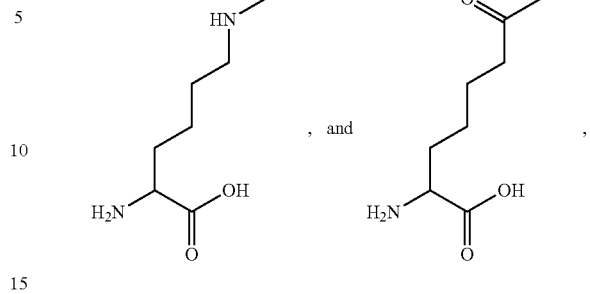

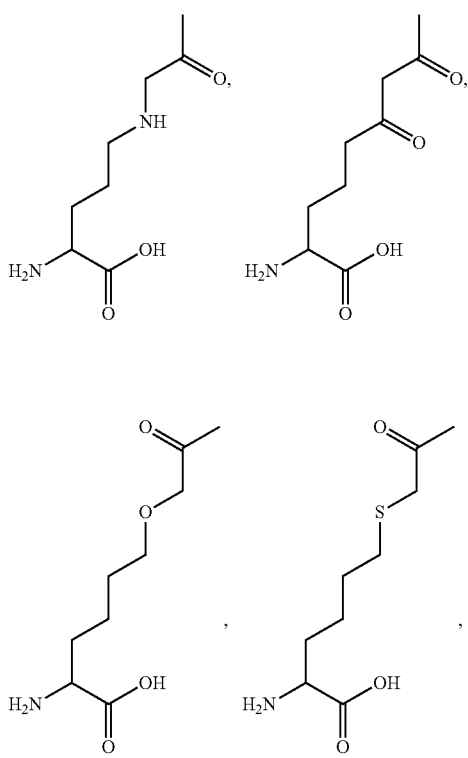

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (VIII) are included:

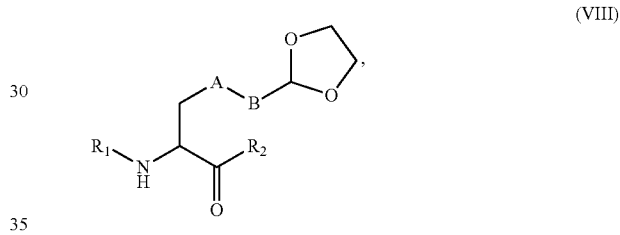

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide.

In addition, the following amino acids having the structure of Formula (IX) are included:

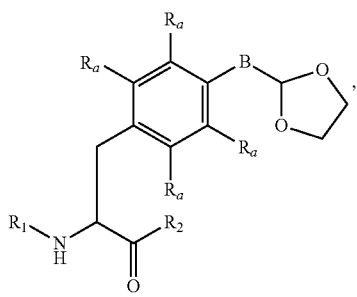
(IX)

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; wherein each $R_a$ is independently selected from the group consisting of H, halogen, alkyl, substituted alkyl, —N(R')$_2$, —C(O)$_1$R' where k is 1, 2, or 3, —C(O)N(R')$_2$, —OR', and —S(O)$_k$R', where each R' is independently H, alkyl, or substituted alkyl.

In addition, the following amino acids are included:

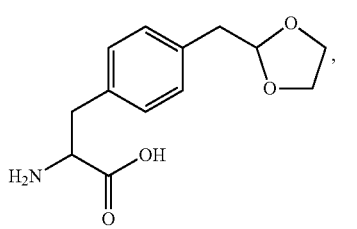

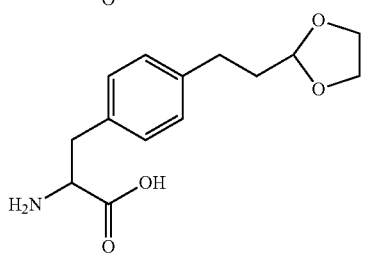

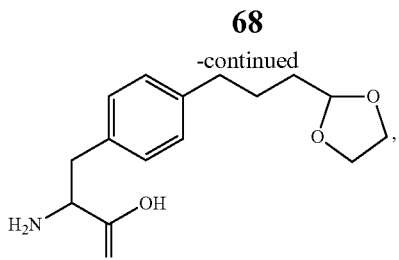

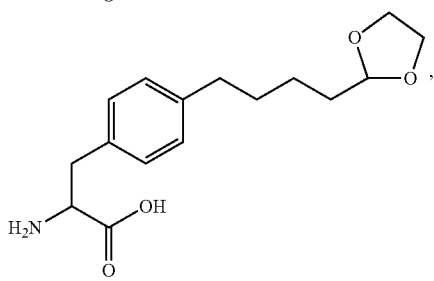

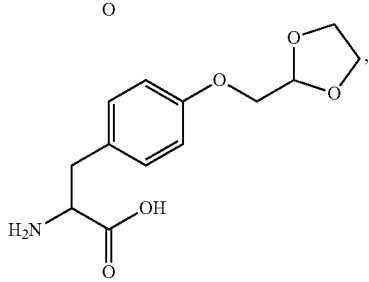

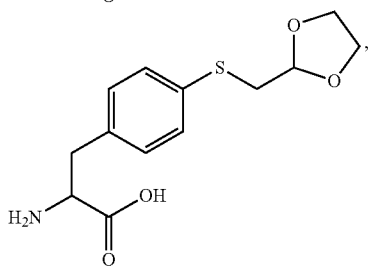

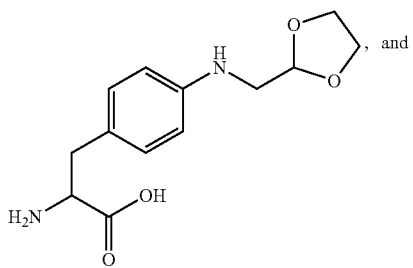

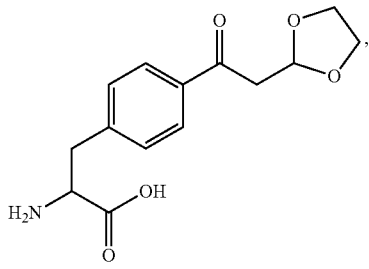

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (X) are included:

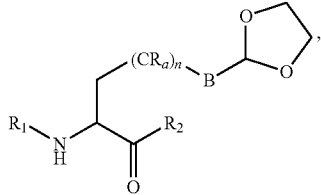
(X)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

In addition, the following amino acids are included:

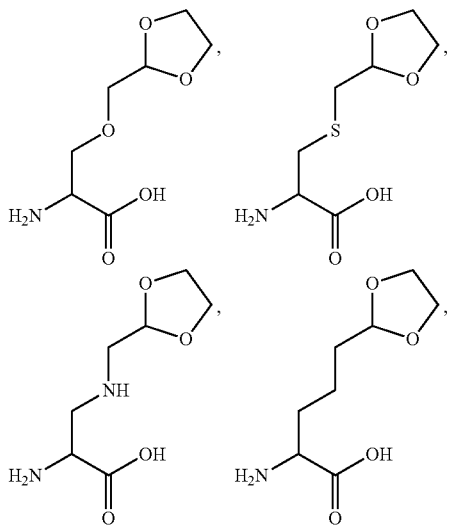

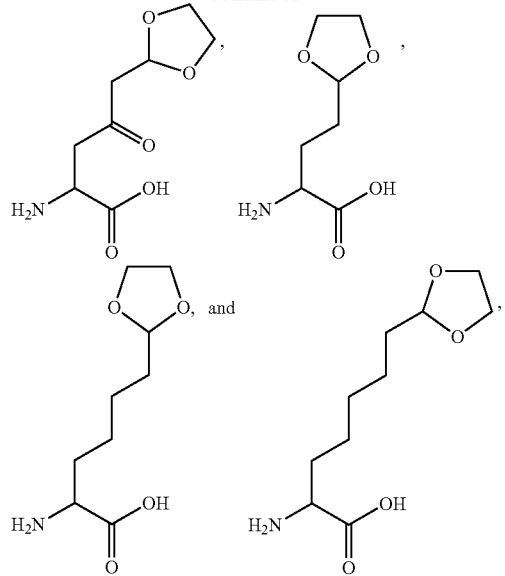

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition to monocarbonyl structures, the non-natural amino acids described herein may include groups such as dicarbonyl, dicarbonyl like, masked dicarbonyl and protected dicarbonyl groups.

For example, the following amino acids having the structure of Formula (XI) are included:

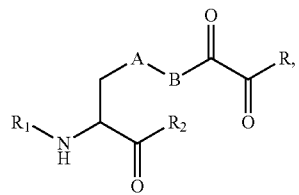
(XI)

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN (R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C (S)N(R')—, —N(R')S(O)$_k$N(R')—, —N(R')—N═, —C(R')
═N—, —C(R')═N—N(R')—, —C(R')═N—N═,
—C(R')$_2$—N═N—, and —C(R')$_2$—N(R')—N(R')—, where
each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, the following amino acids having the structure of Formula (XII) are included:

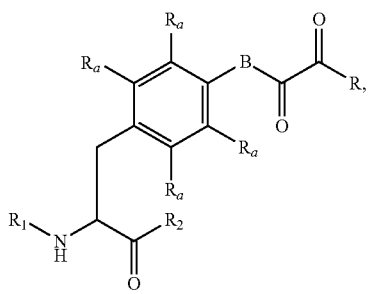

(XII)

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

wherein each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

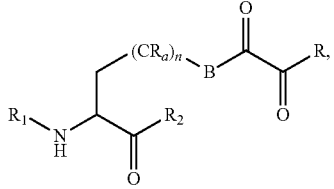

and

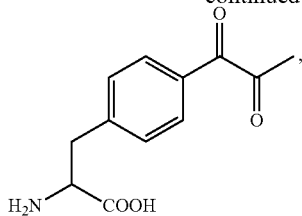

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIII) are included:

(XIII)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

In addition, the following amino acids are included:

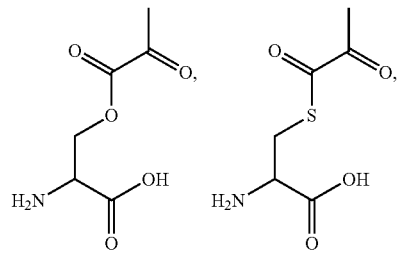
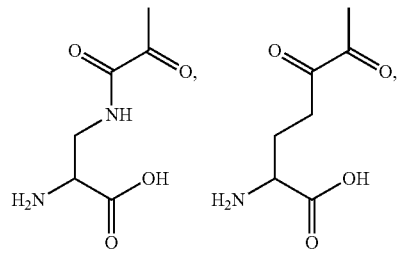
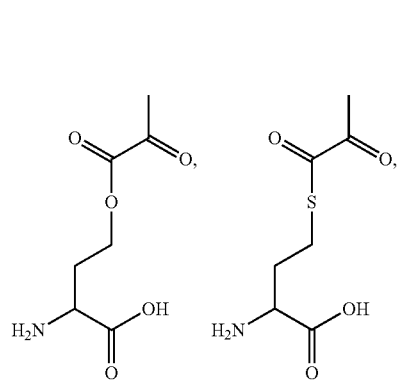
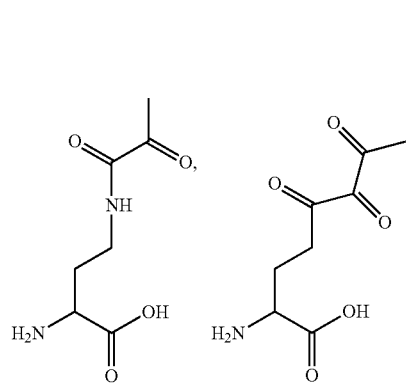
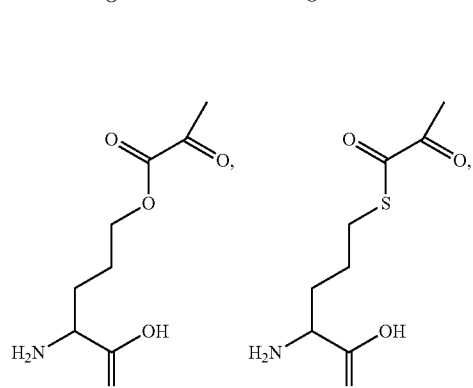

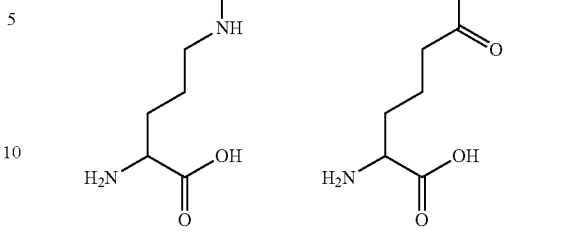
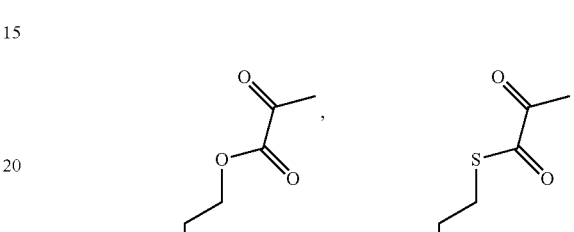
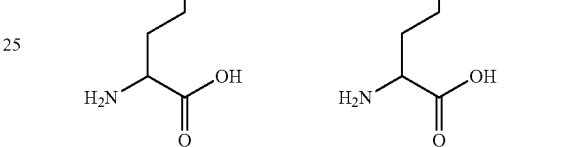
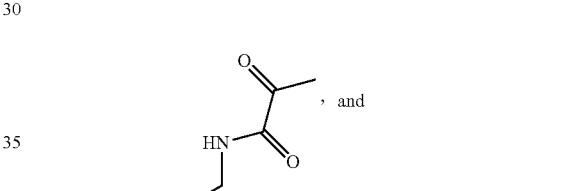
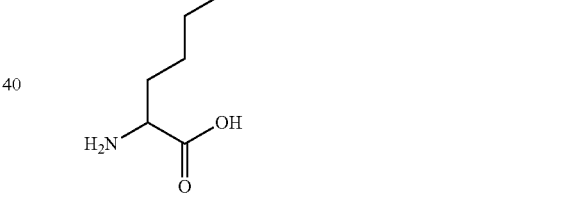
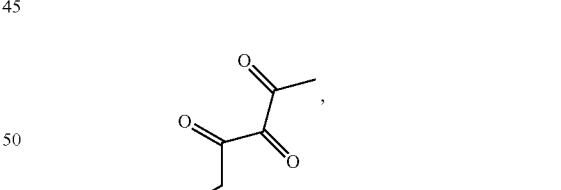

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIV) are included:

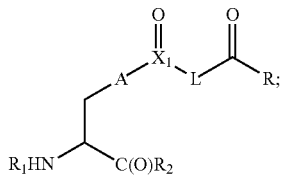

(XIV)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-A) are included:

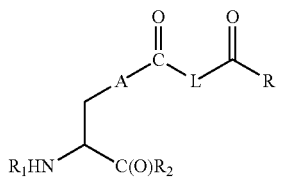

(XIV-A)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-B) are included:

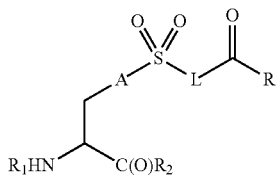

(XIV-B)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XV) are included:

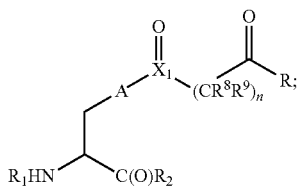

(XV)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-A) are included:

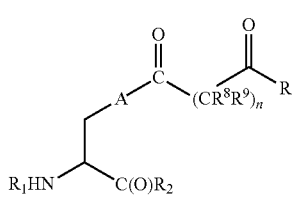

(XV-A)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-B) are included:

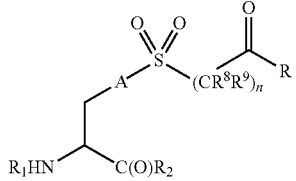

(XV-B)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XVI) are included:

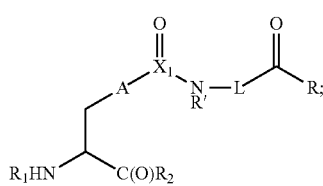

(XVI)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and L is alkylene, substituted alkylene, N(R)(alkylene) or N(R')(substituted alkylene), where R' is H, alkyl, substituted alkyl, cycloalkyl, or substituted cycloalkyl.

In addition, the following amino acids having the structure of Formula (XVI-A) are included:

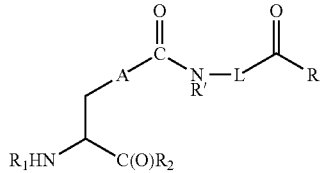

(XVI-A)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R') (substituted alkylene), where R' is H, alkyl, substituted alkyl, cycloalkyl, or substituted cycloalkyl.

In addition, the following amino acids having the structure of Formula (XVI-B) are included:

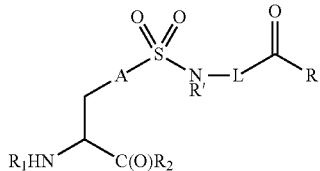
(XVI-B)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, amino acids having the structure of Formula (XVII) are included:

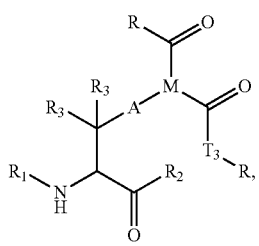
(XVII)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

M is —C($R_3$)—,

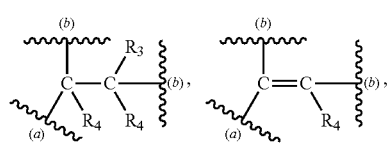

-continued

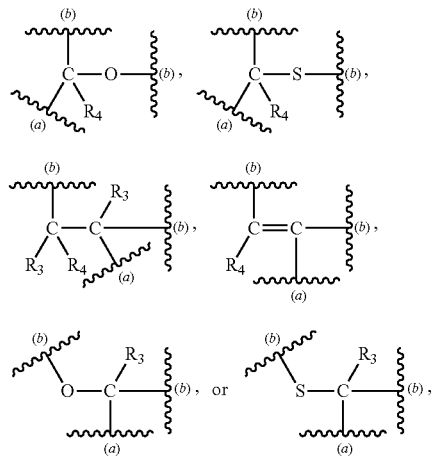

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, amino acids having the structure of Formula (XVIII) are included:

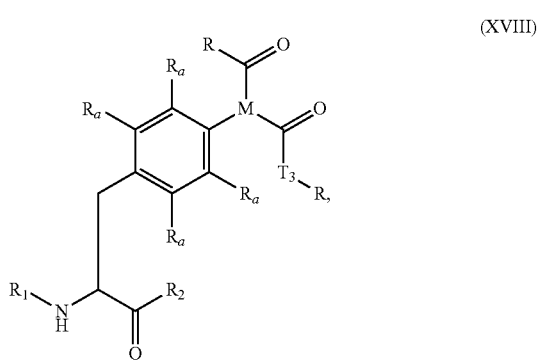
(XVIII)

wherein:

M is —C($R_3$)—,

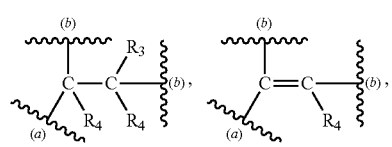

-continued

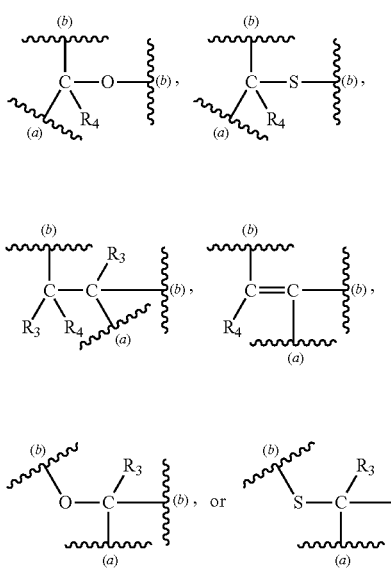

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, amino acids having the structure of Formula (XIX) are included:

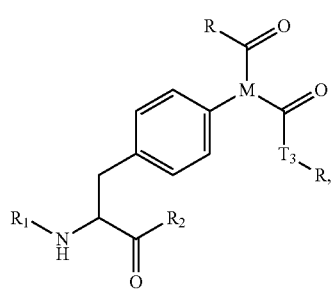

wherein:

R is H, halogen, alkyl, substituted alkyl, cycloalkyl, or substituted cycloalkyl; and $T_3$ is O, or S.

In addition, amino acids having the structure of Formula (XX) are included:

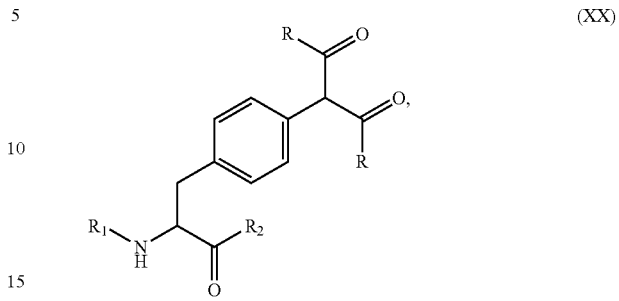

wherein:

R is H, halogen, alkyl, substituted alkyl, cycloalkyl, or substituted cycloalkyl.

In addition, the following amino acids having structures of Formula (XXI) are included:

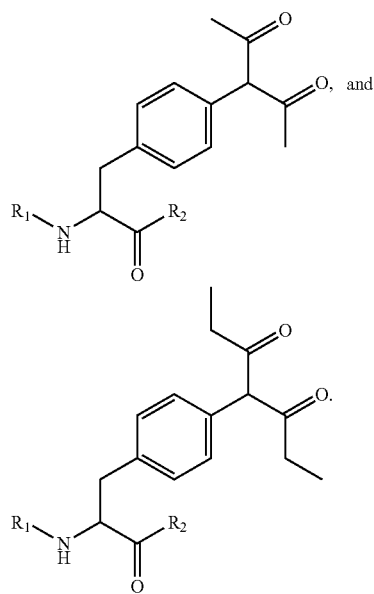

In some embodiments, a polypeptide comprising a non-natural amino acid is chemically modified to generate a reactive carbonyl or dicarbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-natural amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

The carbonyl or dicarbonyl functionality can be reacted selectively with a hydroxylamine-containing reagent under mild conditions in aqueous solution to form the corresponding oxime linkage that is stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl or dicarbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

Structure and Synthesis of Non Natural Amino Acids: Hydroxylamine-Containing Amino Acids U.S. Provisional Patent Application No. 60/638,418 is incorporated by reference in its entirety. Thus, the disclosures provided in Section V (entitled "Non-natural Amino Acids"), Part B (entitled "Structure and Synthesis of Non-Natural Amino Acids: Hydroxylamine-Containing Amino Acids"), in U.S. Provisional Patent Application No. 60/638,418 apply fully to the methods, compositions (including Formulas I-XXXV), techniques and strategies for making, purifying, characterizing, and using non-natural amino acids, non-natural amino acid polypeptides and modified non-natural amino acid polypeptides described herein to the same extent as if such disclosures were fully presented herein. U.S. Patent Publication Nos. 2006/0194256, 2006/0217532, and 2006/0217289 and WO 2006/069246 entitled "Compositions containing, methods involving, and uses of non-natural amino acids and polypeptides," are also incorporated herein by reference in their entirety.

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.*, 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 50:1239-1246; Barton et al., (1987) *Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives. Tetrahedron* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, U.S. Patent Publication No. US 2004/0198637 entitled "Protein Arrays," which is incorporated by reference herein.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

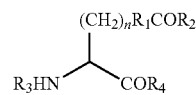

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one of ordinary skill in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., *Bioconjug. Chem.* 3: 262-268 (1992); Geoghegan, K. & Stroh, J., *Bioconjug. Chem.* 3:138-146 (1992); Gaertner et al., *J. Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

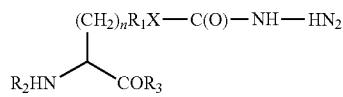

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one of ordinary skill in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., *J. Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

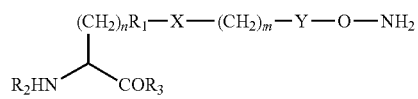

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid), have been isolated from natural sources (Rosenthal, G., *Life Sci.* 60: 1635-1641 (1997). Other aminooxy-containing amino acids can be prepared by one of ordinary skill in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing IFN beta polypeptide can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tomoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the IFN beta polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

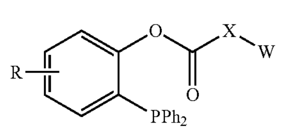

wherein X can be O, N, S or not present, Ph is phenyl, W is a water soluble polymer and R can be H, alkyl, aryl, substituted alkyl and substituted aryl groups. Exemplary R groups include but are not limited to $—CH_2$, $—C(CH_3)_3$, —OR', —NR'R", —SR', -halogen, —C(O)R', —CONR'R", $—S(O)_2R'$, $—S(O)_2NR'R"$, —CN and $—NO_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, $—CF_3$ and $—CH_2CF_3$) and acyl (including but not limited to, $—C(O)CH_3$, $—C(O)CF_3$, $—C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

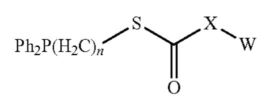

wherein n is 1-10; X can be O, N, S or not present, Ph is phenyl, and W is a water soluble polymer.

Exemplary alkyne-containing amino acids can be represented as follows:

wherein n is 0-10; $R_1$ is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one of ordinary skill in the art.

Exemplary azide-containing amino acids can be represented as follows:

wherein n is 0-10; $R_1$ is an alkyl, aryl, substituted alkyl, substituted aryl or not present; X is O, N, S or not present; in is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m=0. In some embodiments, n is 1, $R_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into IFN beta polypeptides and then reacted with water soluble polymers comprising an aldehyde functionality. In some embodiments, a water soluble polymer, drug conjugate or other payload can be coupled to a IFN beta polypeptide comprising a beta-substituted aminothiol amino acid via formation of the thiazolidine.

F. Additional Reactive Groups

Additional reactive groups and non-naturally encoded amino acids, including but not limited to para-amino-phenylalanine, that can be incorporated into IFN beta polypeptides of the invention are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594. These applications also discuss reactive groups that may be present on PEG or other polymers, including but not limited to, hydroxylamine (aminooxy) groups for conjugation.

Cellular Uptake of Unnatural Amino Acids

Unnatural amino acid uptake by a cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., U.S. Patent Publication No. US 2004/0198637 entitled "Protein Arrays" which is incorporated by reference herein; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly Design-Path™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, those identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, bio distribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology*, 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

EXAMPLES OF OLIGOSACCHARIDES THROUGH GlcNAc-LINKAGE

| Type | Base Structure |
|---|---|
| High-mannose | Manα1-6\>Manα1-6\>Manβ1-4GlcNAcβ1-4GlcNAcβ1-Asn<br>Manα1-3/　　Manα1-3/ |
| Hybrid | Manα1-6\>Manβ1-4GlcNAcβ1-4GlcNAcβ1-Asn<br>GlcNAcβ1-2-Manα1-3/ |
| Complex | GlcNAcβ1-2-Manα1-6\>Manβ1-4GlcNAcβ1-4GlcNAcβ1-Asn<br>GlcNAcβ1-2-Manα1-3/ |
| Xylose | Manα1-6\>Manβ1-4GlcNAcβ1-4GlcNAcβ1-Asn<br>Xylβ1-2/ |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.,* 118:8150-8151; Mahal, et al., (1997) *Science,* 276:1125-1128; Wang, et al., (2001) *Science* 292:498-500; Chin, et al., (2002) *J. Am. Chem. Soc.* 124: 9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2] cycloaddition reaction (see, e.g., Padwa, A. in *Comprehensive Organic Synthesis, Vol.* 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *J. Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2] cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like, These molecules can be added to an unnatural amino acid with an alkynyl group, including but not limited to, p-propargyloxyphenylalanine, or azido group, including but not limited to, p-azido-phenylalanine, respectively.

V. In Vivo Generation of IFN Beta Polypeptides Comprising Non-Naturally-Encoded Amino Acids The IFN beta polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Pat. Nos. 7,045,337 and 7,083,970 which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O-RS). Typically, the O-RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22): 6735-6746 (2003). Exemplary O-RS, or portions thereof, are encoded by polynucleotide sequences and include amino acid sequences disclosed in U.S. Pat. Nos. 7,045,337 and 7,083, 970, each incorporated herein by reference. Corresponding O-tRNA molecules for use with the O-RSs are also described in U.S. Pat. Nos. 7,045,337 and 7,083,970 which are incorporated by reference herein. Additional examples of O-tRNA/aminoacyl-tRNA synthetase pairs are described in WO 2005/007870, WO 2005/007624; and WO 2005/019415.

An example of an azide-specific O-tRNA/aminoacyl-tRNA synthetase system is described in Chin, J. W., et at, *J. Am. Chem. Soc.* 124:9026-9027 (2002). Exemplary O-RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Pat. No. 7,083,970 which is incorporated by reference herein. Exemplary O-tRNA sequences suitable for use in the present invention include, but are not limited to, nucleotide sequences SEQ ID NOs: 1-3 as disclosed in U.S. Pat. No. 7,083,970, which is incorporated by reference herein. Other examples of O-tRNA/aminoacyl-tRNA synthetase pairs specific to particular non-naturally encoded amino acids are described in U.S. Pat. No. 7,045,337 which is incorporated by reference herein. O-RS and O-tRNA that incorporate both keto- and azide-containing amino acids in *S. cerevisiae* are described in Chin, J. W., et at, *Science* 301:964-967 (2003).

Several other orthogonal pairs have been reported. Glutaminyl (see, e.g., Liu, D. R., and Schultz, P. G. (1999) *Proc. Natl. Acad. Sci. U.S.A.* 96:4780-4785), aspartyl (see, e.g., Pastrnak, M., et al., (2000) *Helv. Chim. Acta* 83:2277-2286), and tyrosyl (see, e.g., Ohno, S., et al., (1998) *J. Biochem. (Tokyo, Jpn.)* 124:1065-1068; and, Kowal, A. K., et al., (2001) *Proc. Natl. Acad. Sci. U.S.A.* 98:2268-2273) systems derived from *S. cerevisiae* tRNA's and synthetases have been described for the potential incorporation of unnatural amino acids in *E. coli*. Systems derived from the *E. coli* glutaminyl (see, e.g., Kowal, A. K., et al., (2001) *Proc. Natl. Acad. Sci. U.S.A.* 98:2268-2273) and tyrosyl (see, e.g., Edwards, H., and Schimmel, P. (1990) *Mol. Cell. Biol.* 10:1633-1641) synthetases have been described for use in *S. cerevisiae*. The *E. coli* tyrosyl system has been used for the incorporation of 3-iodo-L-tyrosine in vivo, in mammalian cells. See, Sakamoto, K., et al., (2002) *Nucleic Acids Res.* 30:4692-4699.

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the IFN beta polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O-RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-naturally encoded amino acids are described in U.S. Pat. No. 7,045,337, which is incorporated by reference herein. Methods for selecting an orthogonal tRNA-tRNA synthetase pair for use in in viva translation system of an organism are also described in U.S. Pat. Nos. 7,045,337 and 7,083,970 which are incorporated by reference herein. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O-RS; wherein the at least one recombinant O-RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O-RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a eubacterium, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O-RS, wherein the at least one recombinant O-RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, including but not limited to, at least about two times. In one aspect, the second set of mutated O-RS derived from at least one recombinant O-RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS (O-RS), thereby providing at least one recombinant O-tRNA; wherein the at least one recombinant O-tRNA recognizes a selector codon and is not efficiency recognized by the RS from the second organism and is preferentially aminoacylated by the O-RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacterium thermoautotrophicum, Escherichia coli, Halobacterium*, etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS (O-RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O-RS and inserts an amino acid into a translation product encoded by the positive marker gene, in response to the at least one selector codons. In another embodiment, the concentration of the selection and/or screening agent is varied.

Methods for generating specific O-tRNA/O-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O-RS pair, wherein the at least one specific O-tRNA/O-RS pair comprises at least one recombinant O-RS that is specific for the non-naturally encoded amino acid and the at least one recombinant O-tRNA. Specific O-tRNA/O-RS pairs produced by the methods are included. For example, the specific O-tRNA/O-RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii*, *Methanobacterium thermoautotrophicum*, *Halobacterium*, *Escherichia coli*, *A. fulgidus*, *P. furiosus*, *P. horikoshii*, *A. pernix*, *T. thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii*, *Methanobacterium thermoautotrophicum*, *Halobacterium*, *Escherichia coli*, *A. fulgidus*, *Halobacterium*, *P. furiosus*, *P. horikoshii*, *A. pernix*, *T. thermophilus*, or the like. Alternatively, the second organism can be a eukaryotic organism, including but not limited to, a yeast, a animal cell, a plant cell, a fungus, a mammalian cell, or the like. In various embodiments the first and second organisms are different.

VI. Location of Non-Naturally-Occurring Amino Acids in IFN Beta Polypeptides

The present invention contemplates incorporation of one or more non-naturally-occurring amino acids into IFN beta polypeptides. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity.

A variety of biochemical and structural approaches can be employed to select the desired sites for substitution with a non-naturally encoded amino acid within the IFN beta polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing a IFN beta molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of IFN beta polypeptides can be identified using point mutation analysis, alanine scanning, saturation mutagenesis and screening for biological activity, or homolog scanning methods known in the art. Other methods can be used to identify residues for modification of IFN beta polypeptides include, but are not limited to, sequence profiling (Bowie and Eisenberg, Science 253(5016): 164-70, (1991)), rotamer library selections (Dahiyat and Mayo, Protein Sci 5(5): 895-903 (1996); Dahiyat and Mayo, Science 278(5335): 82-7 (1997); Desjarlais and Handel, Protein Science 4: 2006-2018 (1995); Harbury et al, PNAS USA 92(18): 8408-8412 (1995); Kono et al., Proteins: Structure, Function and Genetics 19: 244-255 (1994); Hellinga and Richards, PNAS USA 91: 5803-5807 (1994)); and residue pair potentials (Jones, Protein Science 3: 567-574, (1994)), and rational design using Protein Design Automation® technology. (See U.S. Pat. Nos. 6,188,965; 6,269,312; 6,403,312; WO98/47089, which are incorporated by reference). Residues that are critical for IFN beta bioactivity, residues that are involved with pharmaceutical stability, antibody epitopes, or receptor binding residues may be mutated. U.S. Pat. Nos. 5,580,723; 5,834,250; 6,013,478; 6,428,954; and 6,451,561, which are incorporated by reference herein, describe methods for the systematic analysis of the structure and function of polypeptides such as IFN beta by identifying active domains which influence the activity of the polypeptide with a target substance. Runkel et al. Biochemistry (2000) 39:2538-2551 and Journal of Interferon and Cytokine Research (2001) 21:931-941 describe mutational and monoclonal antibody analysis of human IFN beta 1a to identify regions involved in receptor binding and biological activity. Cloning, expression, purification, BIAcore analysis, and assessment by antiviral and antiproliferative assays of IFN beta mutants were described. Basu et al. Bioconjugate Chem (2006) 17:618-630 describe site-directed mutagenesis of IFN beta and different conjugates made with PEG polymers. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of mutants of IFN beta polypeptides that contain deletions can also be examined to determine regions of the protein that are likely to be tolerant of substitution with a non-naturally encoded amino acid. In a similar manner, protease digestion and monoclonal antibodies can be used to identify regions of IFN beta that are responsible for binding the IFN receptor. Once residues that are likely to be intolerant to substitution with non-naturally encoded amino acids have been eliminated, the impact of proposed substitutions at each of the remaining positions can be examined. Models may be generated from the three-dimensional crystal structures of other IFN family members and IFN receptors. Protein Data Bank (PDB, available on the World Wide Web at rcsb.org) is a centralized database containing three-dimensional structural data of large molecules of proteins and nucleic acids. Models may be made investigating the secondary and tertiary structure of polypeptides, if three-dimensional structural data is not available. Thus, those of ordinary skill in the art can readily identify amino acid positions that can be substituted with non-naturally encoded amino acids.

In some embodiments, the IFN beta polypeptides of the invention comprise one or more non-naturally occurring amino acids positioned in a region of the protein that does not disrupt the structure of the polypeptide.

Exemplary residues of incorporation of a non-naturally encoded amino acid may be those that are excluded from potential receptor binding regions, may be fully or partially solvent exposed, have minimal or no hydrogen-bonding interactions with nearby residues, may be minimally exposed to nearby reactive residues, may be on one or more of the exposed faces, may be a site or sites that are juxtaposed to a second IFN beta, or other molecule or fragment thereof, may be in regions that are highly flexible, or structurally rigid, as predicted by the three-dimensional, secondary, tertiary, or quaternary structure of IFN beta, bound or unbound to its receptor, or coupled or not coupled to another biologically active molecule, or may modulate the conformation of the IFN beta itself or a dimer or multimer comprising one or more IFN beta, by altering the flexibility or rigidity of the complete structure as desired.

One of ordinary skill in the art recognizes that such analysis of IFN beta enables the determination of which amino acid residues are surface exposed compared to amino acid residues that are buried within the tertiary structure of the protein. Therefore, it is an embodiment of the present invention to substitute a non-naturally encoded amino acid for an amino acid that is a surface exposed residue.

In some embodiments, one or more non-naturally encoded amino acids are incorporated in one or more of the following positions in IFN beta: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4).

In some embodiments, one or more non-naturally encoded amino acids are incorporated at any position in one or more of the following regions corresponding to secondary structures in interferon beta as follows: Helix A (2-22); Helix B (51-71); Helix C (80-107); Helix D (118-136); helix E (139-162); AB loop: AB1 (23-35); AB2 (36-40); AB3 (41-50) from SEQ ID NO: 1 or the corresponding amino acids of SEQ ID NOs: 3, 4. In other embodiments, the non-naturally encoded amino acid is substituted at a position selected from the group consisting of residues 25-35, 80-100, and 121-135 of interferon beta (SEQ ID NO: 1 or the corresponding amino acids from SEQ ID NO: 3, 4). In other embodiments, the non-naturally encoded amino acid is substituted at a position selected from the group consisting of residues 41-49 from interferon beta from SEQ ID NO: 1 or the corresponding amino acids from SEQ ID NO: 3, 4. In some embodiments, one or more non-naturally encoded amino acids are incorporated at one or more of the following positions of IFN beta: 28, 36, 76, 80, 107, 108, 111, and any combination thereof of SEQ ID NO: 1 or the corresponding amino acids in SEQ ID NOs: 3, 4. In some embodiments, one or more non-naturally encoded amino acids are incorporated at one or more of the following positions of IFN beta: 8, 15, 19, 36, 42, 46, 48, 49, 80, 108, 111, 113, 155, and any combination thereof of SEQ ID NO: 1 or the corresponding amino acids in SEQ ID NOs: 3, 4. In some embodiments, one or more non-naturally encoded amino acids are incorporated at one or more of the following positions of IFN beta: 15, 42, 80, 108, 111, 155, and any combination thereof of SEQ ID NO: 1 or the corresponding amino acids in SEQ ID NOs: 3, 4). In some embodiments, the polypeptide of the invention comprises one or more natural amino acid substitution, addition, or deletion. In some embodiments, the polypeptide of the invention comprises a C17S substitution (serine for a cysteine at position 17) of SEQ ID NO: 1 or the corresponding amino acids in SEQ ID NO: 3, 4. In some embodiments, the polypeptide of the invention comprises a C17S substitution (serine for a cysteine at position 17) and one or more natural amino acid substitution, addition, or deletion. In some embodiments, the polypeptide of the invention comprises one or more non-naturally encoded amino acid substitution, addition, or deletion in the signal sequence. In some embodiments, the polypeptide of the invention comprises one or more non-naturally encoded amino acid substitution, addition, or deletion in the signal sequence of SEQ ID NO: 4. In some embodiments, the polypeptide of the invention comprises one or more naturally encoded amino acid substitution, addition, or deletion in the signal sequence of SEQ ID NO: 4. In some embodiments, one or more non-natural amino acids are incorporated in the leader or signal sequence of SEQ ID NOs: 4 or other IFN beta sequence.

An examination of the crystal structure of IFN beta or IFN family member(s) and its interaction with the IFN receptor can indicate which certain amino acid residues have side chains that are fully or partially accessible to solvent. The side chain of a non-naturally encoded amino acid at these positions may point away from the protein surface and out into the solvent.

In some embodiments, the non-naturally occurring amino acid at one or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4 or the corresponding amino acids in another IFN beta sequence).

In some embodiments, the non-naturally occurring amino acid in one or more of these regions is linked to a water soluble polymer, including but not limited to: Helix A (2-22); Helix B (51-71); Helix C (80-107); Helix D (118-136); Helix E (139-162); AB loop: AB1 (23-35); AB2 (36-40); AB3 (41-50) from SEQ ID NO: 1 or the corresponding amino acids of SEQ ID NOs: 3, 4. In other embodiments, the non-naturally occurring amino acid in one or more of these regions is linked to a water soluble polymer, including but not limited to, residues 25-35, 80-100, and 121-135 of interferon beta (SEQ ID NO: 1 or the corresponding amino acids from SEQ ID NO: 3, 4). In other embodiments, the non-naturally occurring amino acid in one or more of these regions is linked to a water soluble polymer, including but not limited to, residues 41-49 from interferon beta from SEQ ID NO: 1 or the corresponding amino acids from SEQ ID NO: 3, 4. In some embodiments, the non-naturally occurring amino acid at one or more of these positions is linked to a water soluble polymer, including but not limited to, positions: 28, 36, 76, 80, 107, 108, 111, and any combination thereof of SEQ ID NO: 1 or the corresponding amino acids in SEQ ID NOs: 3, 4. In some embodiments, the non-naturally occurring amino acid at one or more of these positions is linked to a water soluble polymer, including but not limited to, positions: 8, 15, 19, 36, 42, 46, 48, 49, 80, 108, 111, 113, 155, and any combination thereof of SEQ ID NO: 1 or the corresponding amino acids in SEQ ID NOs: 3, 4). In some embodiments, the non-naturally occurring amino acid at one or more of these positions is linked to a water soluble polymer, including but not limited to, positions: 15, 42, 80, 108, 111, 155, and any combination thereof of SEQ ID NO: 1 or the corresponding amino acids in SEQ ID NOs: 3, 4). In some embodiments, the non-naturally occurring amino acid in the signal or leader sequence is linked to a water soluble polymer (SEQ ID NO: 4 or other IFN beta sequence).

A wide variety of non-naturally encoded amino acids can be substituted for, or incorporated into, a given position in a IFN beta polypeptide. In general, a particular non-naturally encoded amino acid is selected for incorporation based on an examination of the three dimensional crystal structure of a IFN beta polypeptide or other IFN family member with its receptor, a preference for conservative substitutions (i.e., aryl-based non-naturally encoded amino acids, such as p-acetylphenylalaninc or O-propargyltyrosine substituting for Phe, Tyr or Trp), and the specific conjugation chemistry that one desires to introduce into the IFN beta polypeptide (e.g., the introduction of 4-azidophenylalanine if one wants to effect a Huisgen [3+2] cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the IFN beta polypeptide to affect other biological traits of the IFN beta polypeptide. In some cases, the other additions, substitutions or deletions may increase the stability (including but not limited to, resistance to proteolytic degradation) of the IFN beta polypeptide or increase affinity of the IFN beta polypeptide for its receptor. In some cases, the other additions, substitutions or deletions may increase the pharmaceutical stability of the IFN beta polypeptide. In some cases, the other additions, substitutions or deletions may enhance the anti-viral activity of the IFN beta polypeptide. In some cases, the other additions, substitutions or deletions may increase the solubility (including but not limited to, when expressed in E. coli or other host cells) of the IFN beta polypeptide. In some embodiments additions, substitutions or deletions may increase the IFN beta polypeptide solubility following expression in E. coli or other recombinant host cells. In some embodiments sites are selected for substitution with a naturally encoded or non-natural amino acid in addition to another site for incorporation of a non-natural amino acid that results in increasing the polypeptide solubility following expression in E. coli or other recombinant host cells. In some embodiments, the IFN beta polypeptides comprise another addition, substitution or deletion that modulates affinity for the IFN beta polypeptide receptor, binding proteins, or associated ligand, modulates signal transduction after binding to the IFN receptor, modulates circulating half-life, modulates release or bio-availability, facilitates purification, or improves or alters a particular route of administration. In some embodiments, the IFN beta polypeptides comprise an addition, substitution or deletion that increases the affinity of the IFN beta variant for its receptor. Similarly, IFN beta polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, IFN beta size reduction, or other traits of the polypeptide.

In some embodiments, the substitution of a non-naturally encoded amino acid generates an IFN beta antagonist. In some embodiments, a non-naturally encoded amino acid is substituted or added in a region involved with receptor binding. In some embodiments, IFN beta antagonists comprise at least one substitution that cause IFN beta to act as an antagonist. In some embodiments, the IFN beta antagonist comprises a non-naturally encoded amino acid linked to a water soluble polymer that is present in a receptor binding region of the IFN beta molecule.

In some cases, 1, 2, 3, 4, 5, 6, 7, 8, 9, 10, or more amino acids are substituted with one or more non-naturally-encoded amino acids. In some cases, the IFN beta polypeptide further includes 1, 2, 3, 4, 5, 6, 7, 8, 9, 10, or more substitutions of one or more non-naturally encoded amino acids for naturally-occurring amino acids. For example, in some embodiments, one or more residues in IFN beta are substituted with one or more non-naturally encoded amino acids. In some cases, the one or more non-naturally encoded residues are linked to one or more lower molecular weight linear or branched PEGs, thereby enhancing binding affinity and comparable serum half-life relative to the species attached to a single, higher molecular weight PEG.

In some embodiments, up to two of the following residues of IFN beta are substituted with one or more non-naturally-encoded amino acids.

VII. Expression in Non-Eukaryotes and Eukaryotes

To obtain high level expression of a cloned IFN beta polynucleotide, one typically subclones polynucleotides encoding a IFN beta polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing IFN beta polypeptides of the invention are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the IFN beta polypeptides of the invention, host cells for expression are selected based on their ability to use the orthogonal components. Exemplary host cells include Gram-positive bacteria (including but not limited to *B. brevis, B. subtilis*, or *Streptomyces*) and Grain-negative bacteria (*E. coli, Pseudomonas fluorescens, Pseudomonas aeruginosa, Pseudomonas putida*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 μg/liter, at least 50 μg/liter, at least 75 μg/liter, at least 100 μg/liter, at least 200 μg/liter, at least 250 μg/liter, or at least 500 μg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

A number of vectors suitable for expression of IFN beta are commercially available. Useful expression vectors for eukaryotic hosts, include but are not limited to, vectors comprising expression control sequences from SV40, bovine papilloma virus, adenovirus and cytomegalovirus. Such vectors include pcDNA3.1(+)\Hyg (Invitrogen, Carlsbad, Calif., USA) and pCI-neo (Stratagene, La Jolla, Calif., USA). Bacterial plasmids, such as plasmids from E. coli, including pBR322, pET3a and pET12a, wider host range plasmids, such as RP4, phage DNAs, e.g., the numerous derivatives of phage lambda, e.g., NM989, and other DNA phages, such as M13 and filamentous single stranded DNA phages may be used. The 2µ plasmid and derivatives thereof, the POT1 vector (U.S. Pat. No. 4,931,373 which is incorporated by reference), the pJSO37 vector described in (Oldcels, Ann. New York Aced. Sci. 782, 202 207, 1996) and pPICZ A, B or C (Invitrogen) may be used with yeast host cells. For insect cells, the vectors include but are not limited to, pVL941, pBG311 (Cate et al., "Isolation of the Bovine and Human Genes for Mullerian Inhibiting Substance And Expression of the Human Gene In Animal Cells", Cell, 45, pp. 685 98 (1986), pBluebac 4.5 and pMelbac (Invitrogen, Carlsbad, Calif.).

The nucleotide sequence encoding an IFNB polypeptide may or may not also include sequence that encodes a signal peptide. The signal peptide is present when the polypeptide is to be secreted from the cells in which it is expressed. Such signal peptide may be any sequence. The signal peptide may be prokaryotic or eukaryotic. Coloma, M (1992) J. Imm. Methods 152:89 104) describe a signal peptide for use in mammalian cells (murine 1 g kappa light chain signal peptide). Other signal peptides include but are not limited to, the α-factor signal peptide from S. cerevisiae (U.S. Pat. No. 4,870,008 which is incorporated by reference herein), the signal peptide of mouse salivary amylase (O. Hagenbuchle et al., Nature 289, 1981, pp. 643-646), a modified carboxypeptidase signal peptide (L. A. Valls et al., Cell 48, 1987, pp. 887-897), the yeast BAR1 signal peptide (WO 87/02670, which is incorporated by reference herein), and the yeast aspartic protease 3 (YAP3) signal peptide (cf. M. Egel-Mitani et al., Yeast 6, 1990, pp. 127-137).

Examples of suitable mammalian host cells are known to those of ordinary skill in the art. Such host cells may be Chinese hamster ovary (CHO) cells, (e.g. CHO-K1; ATCC CCL-61), Green Monkey cells (COS) (e.g. COS1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. These cell lines and others are available from public depositories such as the American Type Culture Collection, Rockville, Md. In order to provide improved glycosylation of the IFN beta polypeptide, a mammalian host cell may be modified to express sialyltransferase, e.g. 1,6-sialyltransferase, e.g. as described in U.S. Pat. No. 5,047,335, which is incorporated by reference herein.

Methods for the introduction of exogenous DNA into mammalian host cells include but are not limited to, calcium phosphare-mediated transfection, electroporation, DEAE-dextran mediated transfection, liposome-mediated transfection, viral vectors and the transfection methods described by Life Technologies Ltd, Paisley, UK using Lipofectamin 2000 and Roche Diagnostics Corporation, Indianapolis, USA using FuGENE 6. These methods are well known in the art and are described by Ausbel et al. (eds.), 1996, Current Protocols in Molecular Biology, John Wiley & Sons, New York, USA. The cultivation of mammalian cells may be performed according to established methods, e.g. as disclosed in (Animal Cell Biotechnology, Methods and Protocols, Edited by Nigel Jenkins, 1999, Human Press Inc. Totowa, N.J., USA and Harrison Mass. and Rae IF, General Techniques of Cell Culture, Cambridge University Press 1997).

I. Expression Systems, Culture and Isolation

IFN beta polypeptides may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding a IFN beta polypeptide. Such yeasts include, but are not limited to, ascosporogenous yeasts (Endomycetales), basidiosporogenous yeasts and yeasts belonging to the Fungi imperfecti (Blastomycetes) group. The ascosporogenous yeasts are divided into two families, Spermophthoraceae and Saccharomycetaceae. The latter is comprised of four subfamilies, Schizosaccharomycoideae (e.g., genus Schizosaccharomyces), Nadsonioideae, Lipomycoideae and Saccharomycoideae (e.g., genera Pichia, Kluyveromyces and Saccharomyces). The basidiosporogenous yeasts include the genera Leucosporidium, Rhodosporidium, Sporidiobolus, Filobasidium, and Filobasidiella. Yeasts belonging to the Fungi Imperfecti (Blastomycetes) group are divided into two families, Sporobolomycetaceae (e.g., genera Sporobolomyces and Bullera) and Cryptococcaceae (e.g., genus Candida).

Of particular interest for use with the present invention are species within the genera Pichia, Kluyveromyces, Saccharomyces, Schizosaccharomyces, Hansenula, Torulopsis, and Candida, including, but not limited to, P. pastoris, P. guillerimondii, S. cerevisiae, S. carlsbergensis, S. diastaticus, S. douglasii, S. kluyveri, S. norbensis, S. oviformis, K. lactis, K. fragilis, C. albicans, C. maltosa, and H. polymorpha.

The selection of suitable yeast for expression of IFN beta polypeptides is within the skill of one of ordinary skill in the art. In selecting yeast hosts for expression, suitable hosts may include those shown to have, for example, good secretion capacity, low proteolytic activity, good secretion capacity, good soluble protein production, and overall robustness. Yeast are generally available from a variety of sources including, but not limited to, the Yeast Genetic Stock Center, Depaitinent of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a IFN beta polypeptide, are included in the progeny intended by this definition.

Expression and transformation vectors, including extrachromosomal replicons or integrating vectors, have been developed for transformation into many yeast hosts. For example, expression vectors have been developed for S. cerevisiae (Sikorski et al., GENETICS (1989) 122:19; Ito et al., J. BACTE- RIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GENETICS AND GENOMICS (1986) 202:302); *K. fragilis* (Das et al., J. BACTERIOL. (1984) 158:1165); *K. lactis* (De Louvencourt et al., J. BACTERIOL. (1983) 154:737; Van den Berg et al., BIOTECHNOLOGY (NY) (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach et al., NATURE (1982) 300:706); and *Y. lipolytica; A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475-479); *T. reesia* (EP 0 244 234); and filamentous fungi such as, e.g., *Neurospora, Penicillium, Tolypocladium* (WO 91/00357), each incorporated by reference herein.

Control sequences for yeast vectors are known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:12073); and other glycolytic enzymes, such as pyruvate decarboxylase, triose-phosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2µ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/07862; WO 98/37208; and WO 98/26080; European Patent Applications EP 0 946 736; EP 0 732 403; EP 0 480 480; WO 90/10277; EP 0 340 986; EP 0 329 203; EP 0 324 274; and EP 0 164 556. See also Gellissen et al., ANTONIE VAN LEEUWENHOEK (1992) 62(1-2):79-93; Romans et al., YEAST (1992) 8(6):423-488; Goeddel, METHODS IN ENZYMOLOGY (1990) 185:3-7, each incorporated by reference herein.

The yeast host strains may be grown in fermentors during the amplification stage using standard feed batch fermentation methods known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a IFN beta polypeptide, are included in the progeny intended by this definition. Baculovirus expression of IFN beta polypeptides has been described in U.S. Pat. No. 7,144,574, which is incorporated by reference herein.

The selection of suitable insect cells for expression of IFN beta polypeptides is known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those of ordinary skill in the art and fully described in SUMMERS AND SMITH, TEXAS AGRICULTURAL EXPERIMENT STATION BULLETIN No. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM; A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is known to those of ordinary skill in the art. See, e.g., U.S. Pat. Nos. 6,368,825; 6,342,216; 6,338,846; 6,261,805; 6,245,528; 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032; WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographacalifornica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlueBac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN NO. 1555 (1987); Smith et al., MOL. CELL. BIOL. (1983) 3:2156; Luckow and Summers, VIROLOGY (1989) 170:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 11(4):91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273(22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190: 139; Jakobsson et al., J. BIOL. CHEM. (1996) 271:22203; Rowles et al., J. BIOL. CHEM. (1996) 271(37):22376; Reverey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHNIQUES (1993) 14(2):274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Maim and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., *The Regulation of Baculovirus Gene Expression* in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those of ordinary skill in the art. See Miller et al., BIOESSAYS (1989) 11(4):91; SUMMERS AND SMITH, TEXAS AGRICULTURAL EXPERIMENT STATION BULLETIN No. 1555 (1987).

Recombinant baculovirus expression vectors have been developed for infection into several insect cells. For example, recombinant baculoviruses have been developed for, inter alfa, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression, and cell culture technology is generally known to those of ordinary skill in the art.

*E. Coli, Pseudomonas* species, and other Prokaryotes Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3) transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce IFN beta polypeptides at high levels. Examples of such vectors are known to those of ordinary skill in the art and include the pET29 series from Novagen, and the pPOP vectors described in WO99/05297, which is incorporated by reference herein. Such expression systems produce high levels of IFN beta polypeptides in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid Up-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074].

In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of snRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a IFN beta polypeptide, are included in the progeny intended by this definition.

The selection of suitable host bacteria for expression of IFN beta polypeptides is known to those of ordinary skill in the art. In selecting bacterial hosts for expression, suitable hosts may include those shown to have, inter cilia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable *E. coli* hosts include, but are not limited to, strains of BL21, DH10B, or derivatives thereof. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescein*, *Pseudomonas aeruginosa*, and *Pseudomonas putida*. *Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, Mich. available on the World Wide Web at dow.com).

Once a recombinant host cell strain has been established (i.e., the expression construct has been introduced into the host cell and host cells with the proper expression construct are isolated), the recombinant host cell strain is cultured under conditions appropriate for production of IFN beta polypeptides. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the IFN beta polypeptide accumulates intracellularly) or harvesting of culture supernatant in either batch or continuous formats. For production in prokaryotic host cells, batch culture and cell harvest are preferred.

The IFN beta polypeptides of the present invention are normally purified after expression in recombinant systems. The IFN beta polypeptide may be purified from host cells or culture medium by a variety of methods known to the art. IFN beta polypeptides produced in bacterial host cells may be poorly soluble or insoluble (in the form of inclusion bodies). In one embodiment of the present invention, amino acid substitutions may readily be made in the IFN beta polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of the IFN beta polypeptides. When handling inclusion bodies of IFN beta polypeptide, it may be advantageous to minimize the homogenization time on repetitions in order to maximize the yield of inclusion bodies without loss due to factors such as solubilization, mechanical shearing or proteolysis.

Insoluble or precipitated IFN beta polypeptide may then be solubilized using any of a number of suitable solubilization agents known to the art. The IFN beta polypeptide may be solubilized with urea or guanidine hydrochloride. The volume of the solubilized IFN beta polypeptide should be minimized so that large batches may be produced using conveniently manageable batch sizes. This factor may be significant in a large-scale commercial setting where the recombinant host may be grown in batches that are thousands of liters in volume. In addition, when manufacturing IFN beta polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the IFN beta polypeptide inclusion bodies in place of the harsher denaturing agent guanidine hydrochloride. The use of urea significantly reduces the risk of damage to stainless steel equipment utilized in the manufacturing and purification process of IFN beta polypeptide while efficiently solubilizing the IFN beta polypeptide inclusion bodies.

In the case of soluble IFN beta protein, the IFN beta may be secreted into the periplasmic space or into the culture medium. In addition, soluble IFN beta may be present in the cytoplasm of the host cells. It may be desired to concentrate soluble IFN beta prior to performing purification steps. Standard techniques known to those of ordinary skill in the art may be used to concentrate soluble IFN beta from, for example, cell lysates or culture medium. In addition, standard techniques known to those of ordinary skill in the art may be used to disrupt host cells and release soluble IFN beta from the cytoplasm or periplasmic space of the host cells.

When IFN beta polypeptide is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. The cleaved IFN beta polypeptide may be purified from the cleaved fusion sequence by methods known to those of ordinary skill in the art. Such methods will be determined by the identity and properties of the fusion sequence and the IFN beta polypeptide, as will be apparent to one of ordinary skill in the art. Methods for purification may include, but are not limited to, size-exclusion chromatography, hydrophobic interaction chromatography, ion-exchange chromatography or dialysis or any combination thereof.

The IFN beta polypeptide may also be purified to remove DNA from the protein solution. DNA may be removed by any suitable method known to the art, such as precipitation or ion exchange chromatography, but may be removed by precipitation with a nucleic acid precipitating agent, such as, but not limited to, protamine sulfate. The IFN beta polypeptide may be separated from the precipitated DNA using standard well known methods including, but not limited to, centrifugation or filtration. Removal of host nucleic acid molecules is an important factor in a setting where the IFN beta polypeptide is to be used to treat humans and the methods of the present invention reduce host cell DNA to pharmaceutically acceptable levels.

Methods for small-scale or large-scale fermentation can also be used in protein expression, including but not limited to, femmentors, shake flasks, fluidized bed bioreactors, hollow fiber bioreactors, roller bottle culture systems, and stirred tank bioreactor systems. Each of these methods can be performed in a batch, fed-batch, or continuous mode process.

Human IFN beta polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the IFN beta polypeptide of the present invention includes separating deamidated and clipped forms of the IFN beta polypeptide variant from the intact form.

Any of the following exemplary procedures can be employed for purification of IFN beta polypeptides of the invention: affinity chromatography; anion- or cation-exchange chromatography (using, including but not limited to, DEAE SEPHAROSE); chromatography on silica; high performance liquid chromatography (HPLC); reverse phase HPLC; gel filtration (using, including but not limited to, SEPHADEX G-75); hydrophobic interaction chromatography; size-exclusion chromatography; metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, peptides comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods known to those of ordinary skill in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins or peptides comprising unnatural amino acids) are used as purification reagents, including but not limited to, for affinity-based purification of proteins or peptides comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production. Antibodies generated against polypeptides of the present invention may be obtained by administering the polypeptides or epitope-bearing fragments, or cells to an animal, preferably a non-human animal, using routine protocols. One of ordinary skill in the art could generate antibodies using a variety of known techniques. Also, transgenic mice, or other organisms, including other mammals, may be used to express humanized antibodies. The above-described antibodies may be employed to isolate or to identify clones expressing the polypeptide or to purify the polypeptides. Antibodies against polypeptides of the present invention may also be employed to treat diseases, Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use as a vaccine, a polypeptide or a nucleic acid vector will be normally provided as a vaccine formulation (composition). The formulation may further comprise a suitable carrier. Since a polypeptide may be broken down in the stomach, it may be administered parenterally (for instance, subcutaneous, intramuscular, intravenous, or intra-dermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The vaccine formulation may also include adjuvant systems for enhancing the immunogenicity of the formulation which are known to those of ordinary skill in the art. The dosage will depend on the specific activity of the vaccine and can be readily determined by routine experimentation.

In addition to other references noted herein, a variety of purification/protein folding methods are known to those of ordinary skill in the art, including, but not limited to, those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana, (1997) *Bioseparation of Proteins*, Academic Press, Inc.; Bollag et al. (1996) *Protein Methods,* 2nd Edition Wiley-Liss, NY; Walker, (1996) *The Protein Protocols Handbook* Humana Press, NJ, Harris and Angal, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice 3rd Edition* Springer Verlag, NY; Janson and Ryden, (1998) *Protein Purification: Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins or peptides can possess a conformation different from the desired conformations of the relevant polypeptides. In one aspect of the invention, the expressed protein or polypeptide is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) *J. Biol. Chem.,* 268: 14065-14070; Kreitman and Pastan (1993) *Bioconjug. Chem.,* 4: 581-585; and Buchner, et al., (1992) *Anal. Biochem.,* 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of IFN beta polypeptide, the IFN beta polypeptide thus produced may be misfolded and thus lacks or has reduced biological activity. The bioactivity of the protein may be restored by "refolding". In general, misfolded IFN beta polypeptide is refolded by solubilizing (where the IFN beta polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. IFN beta polypeptide may be refolded using standard methods known in the art, such as those described in U.S. Pat. Nos. 4,511,502, 4,511,503, and 4,512,922, which are incorporated by reference herein. The IFN beta polypeptide may also be cofolded with other proteins to form heterodimers or heteromultimers.

After refolding, the IFN beta may be further purified. Purification of IFN beta may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, IFN beta may be exchanged into different buffers and/or concentrated by any of a variety of methods known to the art, including, but not limited to, diafiltration and dialysis. IFN beta that is provided as a single purified protein may be subject to aggregation and precipitation.

The purified IFN beta may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the IFN beta, the IFN beta is sufficiently pure for use as a pharmaceutical product or for further processing, such as conjugation with a water soluble polymer such as PEG.

In some embodiments, pharmacokinetically the IFN beta polypeptides of the present invention have dose linear Cmax and AUC. In some embodiments, the pharmacokinetics of the IFN beta polypeptides of the present invention have a Cmax not less than 60%, 65%, 70%, 75%, 80%, 85%, 90%, 95%, or 100% of REBIF® at the equivalent dose. In some embodiments, the pharmacokinetics of the IFN beta polypeptides of the present invention have a Cmax not less than 100% of REBIF® at the equivalent dose. In some embodiments, the pharmacokinetics of the IFN beta polypeptides of the present invention have a Cmax not less than 105%, 110%, 115%, 120%, 125%, 130%, 135%, 140%, 145%, 150%, 155%, 160%, 165%, 170%, 175%, 180%, 185%, 190%, 195%, 200% or more of REBIF® at the equivalent dose. In some embodiments, the pharmacokinetics of the IFN beta polypeptides of the present invention have a Cmax not less than 60%, 65%, 70%, 75%, 80%, 85%, 90%, 95%, or 100% of AVONEX® or another control administered at the equivalent dose. In some embodiments, the pharmacokinetics of the IFN beta polypeptides of the present invention have a Cmax not less than 100% of AVONEX® or another control administered at the equivalent dose. In some embodiments, the pharmacokinetics of the IFN beta polypeptides of the present invention have a Cmax not less than 105%, 110%, 115%, 120%, 125%, 130%, 135%, 140%, 145%, 150%, 155%, 160%, 165%, 170%, 175%, 180%, 185%, 190%, 195%, 200% or more of AVONEX® or another control administered at the equivalent dose. In some embodiments, the pharmacokinetics of the IFN beta polypeptides of the present invention have PK trough levels sufficient to support once per week dosing allometrically.

In some embodiments, the pharmacodynamics of the IFN beta polypeptides of the present invention induce neopterin and sustain neopterin levels for one week. In some embodiments, the IFN beta polypeptides of the present invention induce sustained neopterin levels for 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, or more days. In some embodiments, the pharmacodynamics of the IFN beta polypeptides of the present invention induce OAS1 gene expression not less than a positive control (a currently marketed IFN beta therapeutic) and sustains levels for one week. In some embodiments, the IFN beta polypeptides of the present invention induce OAS1 gene expression not less than a positive control (a currently marketed IFN beta therapeutic) and sustains levels for 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, or more days. In some embodiments of the present invention, injection site reactions are no worse than the positive controls in Example 27 at equivalent dose. In some embodiments of the present invention, injection site reactions are better than the positive controls in Example 27 at equivalent dose. In other embodiments, there are 5%, 10%, 15%, 20%, 25%, 30%, 35%, 40%, 45%, 50%, 60%, 70%, or 80% fewer injection site reactions caused by the IFN beta polypeptides of the present invention.

Certain IFN beta molecules may be used as therapeutic agents in the absence of other active ingredients or proteins (other than excipients, carriers, and stabilizers, serum albumin and the like), or they may be complexed with another protein or a polymer.

General Purification Methods Any one of a variety of isolation steps may be performed on the cell lysate, extract, culture medium, inclusion bodies, periplasmic space of the host cells, cytoplasm of the host cells, or other material, comprising IFN beta polypeptide or on any IFN beta polypeptide mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the IFN beta polypeptide may be reduced and denatured by first denaturing the resultant purified IFN beta polypeptide in urea, followed by dilution into TRIS buffer containing a reducing agent (such as DTT) at a suitable pH. In another embodiment, the IFN beta polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured IFN beta polypeptide mixture may then be further isolated or purified.

As stated herein, the pH of the first IFN beta polypeptide mixture may be adjusted prior to performing any subsequent isolation steps. In addition, the first IFN beta polypeptide mixture or any subsequent mixture thereof may be concentrated using techniques known in the art. Moreover, the elution buffer comprising the first IFN beta polypeptide mixture or any subsequent mixture thereof may be exchanged for a buffer suitable for the next isolation step using techniques known to those of ordinary skill in the art.

Ion Exchange Chromatography In one embodiment, and as an optional, additional step, ion exchange chromatography may be performed on the first IFN beta polypeptide mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the IFN beta polypeptide at any stage of the purification process to isolate substantially purified IFN beta polypeptide. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding IFN beta over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate (S), or sulfoethyl (SE). The cation exchange matrix may be a strong cation exchanger, preferably having an IFN beta binding pH range of about 2.5 to about 6.0. Alternatively, the strong cation exchanger may have an IFN beta binding pH range of about pH 2.5 to about pH 5.5. The cation exchange matrix may be a strong cation exchanger having an IFN beta binding pH of about 3.0. Alternatively, the cation exchange matrix may be a strong cation exchanger, preferably having an IFN beta binding pH range of about 6.0 to about 8.0. The cation exchange matrix may be a strong cation exchanger preferably having an IFN beta binding pH range of about 8.0 to about 12.5. Alternatively, the strong cation exchanger may have an IFN beta binding pH range of about pH 8.0 to about pH 12.0.

Prior to loading the IFN beta, the cation exchange matrix may be equilibrated, for example, using several column volumes of a dilute, weak acid, e.g., four column volumes of 20 mM acetic acid, pH 3. Following equilibration, the IFN beta may be added and the column may be washed one to several times, prior to elution of substantially purified IFN beta, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified IFN beta may be eluted by contacting the cation exchanger matrix with a buffer having a sufficiently low pH or ionic strength to displace the IFN beta from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes.

Following adsorption of the IFN beta polypeptide to the cation exchanger matrix, substantially purified IFN beta polypeptide may be eluted by contacting the matrix with a buffer having a sufficiently high pH or ionic strength to displace the IFN beta polypeptide from the matrix. Suitable buffers for use in high pH elution of substantially purified IFN beta polypeptide may include, but not limited to, citrate, phosphate, formate, acetate, HEPES, and MES buffers ranging in concentration from at least about 5 mM to at least about 100 mM.

Reverse-Phase Chromatography RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the IFN beta polypeptide to isolate substantially purified IFN beta polypeptide. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the IFN beta polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, and triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Techniques Hydrophobic interaction chromatography (HIC) may be performed on the IFN beta polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.).

Briefly, prior to loading, the HIC column may be equilibrated using standard buffers known to those of ordinary skill in the art, such as an acetic acid/sodium chloride solution or HEPES containing ammonium sulfate. Ammonium sulfate may be used as the buffer for loading the HIC column. After loading the IFN beta polypeptide, the column may then washed using standard buffers and conditions to remove unwanted materials but retaining the IFN beta polypeptide on the HIC column. The IFN beta polypeptide may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the IFN beta molecules. The eluant may then be concentrated, for example, by filtration such as diafiltration or ultrafiltration. Diafiltration may be utilized to remove the salt used to elute the IFN beta polypeptide.

Other Purification Techniques Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first IFN beta polypeptide mixture or any subsequent mixture thereof, to remove any excess salts and to replace the buffer with a suitable buffer for the next isolation step or even formulation of the final drug product.

The yield of IFN beta polypeptide, including substantially purified IFN beta polypeptide, may be monitored at each step described herein using techniques known to those of ordinary skill in the art. Such techniques may also be used to assess the yield of substantially purified IFN beta polypeptide following the last isolation step. For example, the yield of IFN beta polypeptide may be monitored using any of several reverse phase high pressure liquid chromatography columns, having a variety of alkyl chain lengths such as cyano RP-HPLC, $C_{19}$RP-HPLC; as well as cation exchange HPLC and gel filtration HPLC.

In specific embodiments of the present invention, the yield of IFN beta after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the IFN beta in the starting material for each purification step.

Purity may be determined using standard techniques, such as SDS-PAGE, or by measuring IFN beta polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of IFN beta polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The IFN beta polypeptide fractions which are within the IPC limits are pooled.

DEAE Sepharose (Pharmacia) material consists of diethylaminoethyl (DEAE)-groups which are covalently bound to the surface of Sepharose beads. The binding of IFN beta polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and IFN beta polypeptide is eluted with a buffer with increased ionic strength. The column is packed with DEAE Sepharose fast flow. The column volume is adjusted to assure a IFN beta polypeptide load in the range of 3-10 mg IFN beta polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, IFN beta polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at $-70°$ C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, Limulus Amebocyte Lysate (LAL) assays. The Endosafe™-PTS assay is a colorimetric, single tube system that utilizes cartridges preloaded with LAL reagent, chromogenic substrate, and control standard endotoxin along with a handheld spectrophotometer. Alternate methods include, but are not limited to, a Kinetic LAL method that is turbidmetric and uses a 96 well format.

A wide variety of methods and procedures can be used to assess the yield and purity of a IFN beta protein comprising one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one of ordinary skill in the art.

Additional methods include, but are not limited to: SDS-PAGE coupled with protein staining methods, immunoblotting, matrix assisted laser desorption/ionization-mass spectrometry (MALDI-MS), liquid chromatography/mass spectrometry, isoelectric focusing, analytical anion exchange, chromatofocusing, and circular dichroism.

VIII. Expression in Alternate Systems

Several strategies have been employed to introduce unnatural amino acids into proteins in non-recombinant host cells, mutagenized host cells, or in cell-free systems. These systems are also suitable for use in making the IFN beta polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem,* 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.,* 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.,* 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskorn, J. Kellermann and R. Huber, *Eur. J. Biochem.,* 230:788 (1995); and, N. Budisa, W. Kambrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.,* 428:68 (1998); J. C. van Hest, K. L. Kiick and D. A. Tirrell, *J. Am. Chem. Soc.,* 122:1282 (2000); and, K. L. Kiick and D. A. Tirrell, *Tetrahedron,* 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala[294] by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soil and S. Nishimura, *J. Biol. Chem.,* 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doling, H. D. Mootz, L. A. Nangle, T. L. Hendrickson, V. de Crecy-Lagard, P. Schimmel and P. Marliere, *Science,* 292:501 (2001). ValRS can misaminoacylate tRNAVal with Cys, Thr, or aminobutyrate (Abu); these non-cognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature,* 192: 1227-1232 (1961); Hofmann, K., Bohn, H. *Studies on polypeptides. XXXVI. The effect of pyrazole-imidazole replacements on the S-protein activating potency of an S-peptide fragment, J. Am. Chem,* 88(24):5914-5919 (1966); Kaiser, E. T. *Synthetic approaches to biologically active peptides and proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987);

Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266(5183):243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238(4832): 1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enyzme active sites, Science,* 226 (4674):505-511 (1984); Neet, K. E., Nanci A, Koshland, D. E. *Properties of thiol-subtilisin, J. Biol. Chem.,* 243(24):6392-6401 (1968); Polgar, L. et M. L. Bender. *A new enzyme containing a synthetically formed active site. Thiol-subtilisin. J. Am. Chem Soc,* 88:3153-3154 (1966); and, Pollack, S. J., Nakayama, G. Schultz, P. G. *Introduction of nucleophiles and spectroscopic probes into antibody combining sites, Science,* 242(488 0:1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am. Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based oligonoucleotide-directed mutagensis, Nucleic Acids Res,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2)$_3$'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Ace. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{Asn}_{CCCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin, Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based amino acylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing E. coli lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Stephan in Scientist 2005 Oct. 10; pages 30-33 describes additional methods to incorporate non-naturally encoded amino acids into proteins. Lu et al. in Mol. Cell. 2001 October; 8(4):759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, Science, 268:439 (1995); and, D. A. Dougherty, Curr. Opin. Chem. Biol., 4:645 (2000), A Xenopus oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, J. Meseth, F. Talabot, M. Peitsch, J. Knowles, H. Vogel and A. Chollet, J. Biol. Chem., 271:19991 (1996); the incorporation of biotinylated amino acids to identify surface-exposed residues in ion channels, see, e.g., J. P. Gallivan, H. A. Lester and D. A. Dougherty, Chem. Biol., 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, Cell, 96:89 (1999); and, T. Lu, A. Y. Ting, J. Mainland, L. Y. Jan, P. G. Schultz and J. Yang, Nat. Neurosci., 4:239 (2001).

The ability to incorporate unnatural amino acids directly into proteins in vivo offers a wide variety of advantages including but not limited to, high yields of mutant proteins, technical ease, the potential to study the mutant proteins in cells or possibly in living organisms and the use of these mutant proteins in therapeutic treatments and diagnostic uses. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.*, 7:419 (1998).

It may also be possible to obtain expression of a IFN beta polynucleotide of the present invention using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering,* 74:309-316 (2001); Kim, D. M. and J. R. Swartz, *Biotechnology Letters,* 22, 1537-1542, (2000); Kim, D. M., and J. R. Swartz, *Biotechnology Progress,* 16, 385-390, (2000); Kim, D. M., and J. R. Swartz, Biotechnology and Bioengineering, 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of IFN beta polypeptides comprising a non-naturally encoded amino acid includes the mRNA-peptide fusion technique. See, e.g., R. Roberts and J. Szostak, *Proc. Natl. Acad. Sci. (USA)* 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of IFN beta polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl. Acad. Sci. (USA)* 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 (α or β), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

IX. Macromolecular Polymers Coupled to IFN Beta Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to IFN beta polypeptides of the present invention to modulate biological properties of the IFN beta polypeptide, and/or provide new biological properties to the IFN beta molecule. These macromolecular polymers can be linked to the IFN beta polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated IFN beta polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tin, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereat hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutarnic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG: IFN beta polypeptide conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of IFN beta polypeptide used for therapy gives an acceptable rate of change and maintains desired response at a beneficial level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the IFN beta polypeptide by the formula:

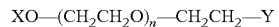

$$XO\text{---}(CH_2CH_2O)_n\text{---}CH_2CH_2\text{---}Y$$

where n is 2 to 10,000 and X is H or a terminal modification, including but not limited to, a $C_{1-4}$ alkyl, a protecting group, or a terminal functional group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a IFN beta polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the IFN beta polypeptide to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the IFN beta polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PEG is between about 100 Da and about 50,000 Da. In some embodiments, PEG is between about 100 Da and about 40,000 Da. In some embodiments, PEG is between about 1,000 Da and about 40,000 Da. In some embodiments, PEG is between about 5,000 Da and about 40,000 Da. In some embodiments, PEG is between about 10,000 Da and about 40,000 Da. Branched chain PEGs, including but not limited to, PEG molecules with each chain having a MW ranging from 1-100 kDa (including but not limited to, 1-50 kDa or 5-20 kDa) can also be used. The molecular weight of each chain of the branched chain PEG may be, including but not limited to, between about 1,000 Da and about 100,000 Da or more. The molecular weight of each chain of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PEG is between about 1,000 Da and about 50,000 Da. In some embodiments, the molecular weight of each chain of the branched chain PEG is between about 1,000 Da and about 40,000 Da. In some embodiments, the molecular weight of each chain of the branched chain PEG is between about 5,000 Da and about 40,000 Da. In some embodiments, the molecular weight of each chain of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the IFN beta polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and polypropylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula $CH_2CH_2O—(CH_2CH_2O)$, $CH_2CH_2—$, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and about 50,000 Da. In some embodiments, the molecular weight of PEG is between about 100 Da and about 40,000 Da. In some embodiments, the molecular weight of PEG is between about 1,000 Da and about 40,000 Da. In some embodiments, the molecular weight of PEG is between about 5,000 Da and about 40,000 Da. In some embodiments, the molecular weight of PEG is between about 10,000 Da and about 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(—YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

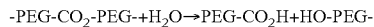

-PEG-CO$_2$-PEG-+H$_2$O→PEG-CO$_2$H+HO-PEG-

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da, In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

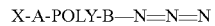

X-A-POLY-B—N═N═N wherein:
N═N═N is an azide moiety;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech.Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900, 461). All of the above references and patents are incorporated herein by reference.

In certain embodiments of the present invention, the polymer derivatives of the invention comprise a polymer backbone having the structure:

wherein:
X is a functional group as described above; and
n is about 20 to about 4000.
In another embodiment, the polymer derivatives of the invention comprise a polymer backbone having the structure:

wherein:
W is an aliphatic or aromatic linker moiety comprising between 1-10 carbon atoms;
n is about 20 to about 4000; and
X is a functional group as described above. m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

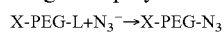

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to forth an azide-containing polymer derivative product wherein the azide is separated from the polymer backbone by a linking group.

An exemplary reaction scheme is shown below:

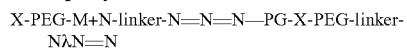

wherein:
PEG is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

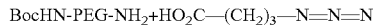

$$BocHN\text{-}PEG\text{-}NH_2 + HO_2C\text{-}(CH_2)_3\text{-}N{=}N{=}N$$

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

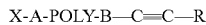

$$X\text{-}A\text{-}POLY\text{-}B\text{-}C{\equiv}C\text{-}R$$

wherein:
R can be either H or an alkyl, alkene, alkyoxy, or aryl or substituted aryl group;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

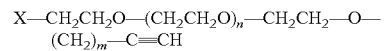

$$X\text{-}CH_2CH_2O\text{-}(CH_2CH_2O)_n\text{-}CH_2CH_2\text{-}O\text{-}(CH_2)_m\text{-}C{\equiv}CH$$

wherein:
X is a functional group as described above;
n is about 20 to about 4000; and
m is between 1 and 10.
Specific examples of each of the heterobifunctional PEG polymers are shown below.

The acetylene-containing PEG derivatives of the invention can be prepared using methods known to those of ordinary skill in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

$$X\text{-}PEG\text{-}Nu + L\text{-}A\text{-}C \rightarrow X\text{-}PEG\text{-}Nu\text{-}A\text{-}C{\equiv}CR'$$

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:

PEG is poly(ethylene glycol) and X is a capping group such as alkoxy or a functional group as described above; and R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are known to those of ordinary skill in the art.

Purification of the crude product can usually be accomplished by methods known in the art including, but are not limited to, precipitation of the product followed by chromatography, if necessary.

Water soluble polymers can be linked to the IFN beta polypeptides of the invention. The water soluble polymers may be linked via a non-naturally encoded amino acid incorporated in the IFN beta polypeptide or any functional group or substituent of a non-naturally encoded or naturally encoded amino acid, or any functional group or substituent added to a non-naturally encoded or naturally encoded amino acid. Alternatively, the water soluble polymers are linked to a IFN beta polypeptide incorporating a non-naturally encoded amino acid via a naturally-occurring amino acid (including but not limited to, cysteine, lysine or the amine group of the N-terminal residue). In some cases, the IFN beta polypeptides of the invention comprise 1, 2, 3, 4, 5, 6, 7, 8, 9, non-natural amino acids, wherein one or more non-naturally-encoded amino acid(s) are linked to water soluble polymer(s) (including but not limited to, PEG and/or oligosaccharides). In some cases, the IFN beta polypeptides of the invention further comprise 1, 2, 3, 4, 5, 6, 7, 8, 9, 10, or more naturally-encoded amino acid(s) linked to water soluble polymers. In some cases, the IFN beta polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the IFN beta polypeptide relative to the unconjugated form.

The number of water soluble polymers linked to a IFN beta polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of IFN beta is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a IFN beta polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

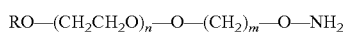

where R is a simple alkyl (methyl, ethyl, propyl, etc.), in is 2-10 and n is 100-1,000 (i.e., average molecular weight is between 5-40 kDa).

In some embodiments, the hydrazine- or hydrazide-containing PEG derivative will have the structure:

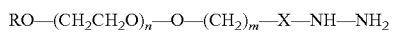

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

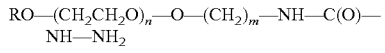

where R is a simple alkyl (methyl, ethyl, propyl, etc.), m is 2-10 and n is 100-1,000.

In another embodiment of the invention, a IFN beta polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

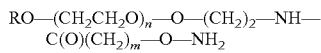

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

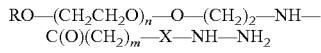

where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

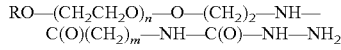

where R is a simple alkyl (methyl, ethyl, propyl, etc.), m is 2-10 and n is 100-1,000.

In another embodiment of the invention, a IFN beta polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, may be from 5-20 kDa.

In another embodiment of the invention, a IFN beta polypeptide comprising a non-naturally encoded amino acid is modified with a PEG derivative having a branched structure. For instance, in some embodiments, the hydrazine- or hydrazide-terminal PEG derivative will have the following structure:

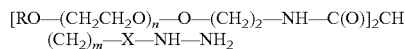

where R is a simple alkyl (methyl, ethyl, propyl, etc.), in is 2-10 and n is 100-1,000, and X is optionally a carbonyl group (C=O) that can be present or absent.

In some embodiments, the PEG derivatives containing a semicarbazide group will have the structure:

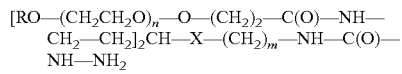

where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

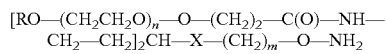

where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the IFN beta polypeptide can modulate the binding of the IFN beta polypeptide to the IFN betapolypeptide receptor. In some embodiments, the linkages are arranged such that the IFN beta polypeptide binds the IFN beta polypeptide receptor with a $K_d$ of about 400 nM or lower, with a $K_d$ of 150 nM or lower, and in some cases with a $K_d$ of 100 nM or lower, as measured by an equilibrium binding assay, such as that described in Spencer et al., *J. Biol. Chem.*, 263:7862-7867 (1988).

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-52 (1985)). All references and patents cited are incorporated by reference herein.

PEGylation (i.e., addition of any water soluble polymer) of IFN beta polypeptides containing a non-naturally encoded amino acid, such as p-azido-L-phenylalanine, is carried out by any convenient method. For example, IFN beta polypeptide is PEGylated with an alkyne-terminated mPEG derivative. Briefly, an excess of solid mPEG(5000)-O—CH$_2$—C≡CH is added, with stirring, to an aqueous solution of p-azido-L-Phe-containing IFN beta polypeptide at room temperature. Typically, the aqueous solution is buffered with a buffer having a pK$_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated IFN beta polypeptide variants from free mPEG(5000)-O—CH$_2$—C≡CH and any high-molecular weight complexes of the pegylated IFN beta polypeptide which may form when unblocked PEG is activated at both ends of the molecule, thereby crosslinking IFN beta polypeptide variant molecules. The conditions during hydrophobic interaction chromatography are such that free mPEG(5000)-O—CH$_2$—C≡CH flows through the column, while any crosslinked PEGylated IFN beta polypeptide variant complexes elute after the desired forms, which contain one IFN beta polypeptide variant molecule conjugated to one or more PEG groups. Suitable conditions vary depending on the relative sizes of the cross-linked complexes versus the desired conjugates and are readily determined by those of ordinary skill in the art. The eluent containing the desired conjugates is concentrated by ultrafiltration and desalted by diafiltration.

If necessary, the PEGylated IFN beta polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, A Z in PROTEIN PURIFICATION METHODS, A PRACTICAL APPROACH (Harris & Angal, Eds.) IRL Press 1989, 293-306). The purity of the IFN beta-PEG conjugate can be assessed by proteolytic degradation (including but not limited to, trypsin cleavage) followed by mass spectrometry analysis. Pepinsky R B., et al., *J. Pharmcol. & Exp. Ther.* 297(3):1059-66 (2001).

A water soluble polymer linked to an amino acid of a IFN beta polypeptide of the invention can be further derivatized or substituted without limitation.

Azide-Containing PEG Derivatives

In another embodiment of the invention, a IFN beta polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

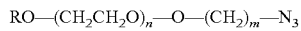

where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

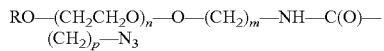

where R is a simple alkyl (methyl, ethyl, propyl, etc.), m is 2-10, p is 2-10 and n is 100-1,000 (i.e., average molecular weight is between 5-40 kDa).

In another embodiment of the invention, a IFN beta polypeptide comprising a alkyne-containing amino acid is modified with a branched PEG derivative that contains a terminal azide moiety, with each chain of the branched PEG having a MW ranging from 10-40 kDa and may be from 5-20 kDa. For instance, in some embodiments, the azide-terminal PEG derivative will have the following structure:

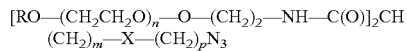

where R is a simple alkyl (methyl, ethyl, propyl, etc.), m is 2-10, p is 2-10, and n is 100-1,000, and X is optionally an O, N, S or carbonyl group (C-0), in each case that can be present or absent.

Alkene-Containing PEG Derivatives

In another embodiment of the invention, a IFN beta polypeptide is modified with a PEG derivative that contains an alkyne moiety that will react with an azide moiety present on the side chain of the non-naturally encoded amino acid.

In some embodiments, the alkyne-terminal PEG derivative will have the following structure:

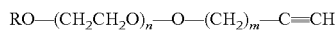

where R is a simple alkyl (methyl, ethyl, propyl, etc.), in is 2-10 and n is 100-1,000 (i.e., average molecular weight is between 5-40 kDa).

In another embodiment, a IFN beta polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

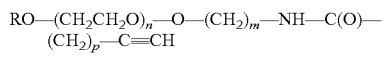

where R is a simple alkyl (methyl, ethyl, propyl, etc.), m is 2-10, p is 2-10 and n is 100-1,000.

In another embodiment of the invention, a IFN beta polypeptide comprising an azide-containing amino acid is modified with a branched PEG derivative that contains a terminal alkyne moiety, with each chain of the branched PEG having a MW ranging from 10-40 kDa and may be from 5-20 kDa. For instance, in some embodiments, the alkyne-terminal PEG derivative will have the following structure:

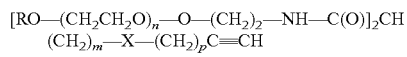

where R is a simple alkyl (methyl, ethyl, propyl, etc.), in is 2-10, p is 2-10, and n is 100-1,000, and X is optionally an O, N, S or carbonyl group (C═O), or not present.

Phosphine-Containing PEG Derivatives

In another embodiment of the invention, a IFN beta polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

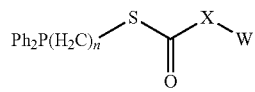

wherein n is 1-10; X can be O, N, S or not present, Ph is phenyl, and W is a water soluble polymer.

In some embodiments, the PEG derivative will have the structure:

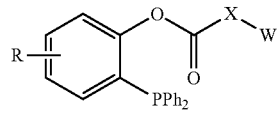

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2$R', —$S(O)_2$NR'R", —CN and —$NO_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

Other PEG Derivatives and General PEGylation Techniques

Other exemplary PEG molecules that may be linked to IFN beta polypeptides, as well as PEGylation methods include, but are not limited to, those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949;

2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, hi-functional, multi-functional, or any combination thereof.

Additional polymer and PEG derivatives including but not limited to, hydroxylamine (aminooxy) PEG derivatives, are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

Heterologous Fc Fusion Proteins

The interferon beta compounds described above may be fused directly or via a peptide linker to the Fc portion of an immunoglobulin. Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class.

As used herein, the Fc portion of an immunoglobulin has the meaning commonly given to the term in the field of immunology. Specifically, this term refers to an antibody fragment which is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through noncovalent interactions and disulfide bonds. The Fc portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C. A. K., ed., W.H. Freeman and Co., 1992, the teachings of which are herein incorporated by reference. The Fc portion can further include one or more glycosylation sites. The amino acid sequences of numerous representative Fc proteins containing a hinge region, CH2 and CH3 domains, and one N-glycosylation site are well known in the art.

There are five types of human immunoglobulin Fc regions with different effector functions and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fc receptor. There are four IgG subclasses G1, G2, G3, and G4, each of which has different effector functions. G1, G2, and G3 can bind C1q and fix complement while G4 cannot. Even though G3 is able to bind C1q more efficiently than G1, G1 is more effective at mediating complement-directed cell lysis. G2 fixes complement very inefficiently. The C1q binding site in IgG is located at the carboxy terminal region of the CH2 domain.

All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

IgA can exist both in a monomeric and dimeric form held together by a J-chain. IgA is the second most abundant Ig in serum, but it has a half-life of only 6 days. IgA has three effector functions. It binds to an IgA specific receptor on macrophages and eosinophils, which drives phagocytosis and degranulation, respectively. It can also fix complement via an unknown alternative pathway.

IgM is expressed as either a pentamer or a hexamer, both of which are held together by a J-chain. IgM has a serum half-life of 5 days. It binds weakly to C1q via a binding site located in its CH3 domain. IgD has a half-life of 3 days in serum. It is unclear what effector functions are attributable to this Ig. IgE is a monomeric Ig and has a serum half-life of 2.5 days. IgE binds to two Fc receptors which drives degranulation and results in the release of proinflammatory agents.

Depending on the desired in vivo effect, the heterologous fusion proteins of the present invention may contain any of the isotypes described above or may contain mutated Fc regions wherein the complement and/or Fc receptor binding functions have been altered. Thus, the heterologous fusion proteins of the present invention may contain the entire Fc portion of an immunoglobulin, fragments of the Fc portion of an immunoglobulin, or analogs thereof fused to an interferon beta compound.

The fusion proteins of the present invention can consist of single chain proteins or as multi-chain polypeptides. Two or more Fc fusion proteins can be produced such that they interact through disulfide bonds that naturally form between Fc regions. These multimers can be homogeneous with respect to the interferon beta compound or they may contain different interferon beta compounds fused at the N-terminus of the Fc portion of the fusion protein.

Regardless of the final structure of the fusion protein, the Fc or Fc-like region may serve to prolong the in vivo plasma half-life of the interferon beta compound fused at the N-terminus. Also, the interferon beta component of a fusion protein compound should retain at least one biological activity of interferon beta. An increase in therapeutic or circulating half-life can be demonstrated using the method described herein or known in the art, wherein the half-life of the fusion protein is compared to the half-life of the interferon beta compound alone. Biological activity can be determined by in vitro and in vivo methods known in the art.

Since the Fc region of IgG produced by proteolysis has the same in vivo half-life as the intact IgG molecule and Fab fragments are rapidly degraded, it is believed that the relevant sequence for prolonging half-life reside in the CH2 and/or CH3 domains. Further, it has been shown in the literature that the catabolic rates of IgG variants that do not bind the high-affinity Fc receptor or C1q are indistinguishable from the rate of clearance of the parent wild-type antibody, indicating that the catabolic site is distinct from the sites involved in Fc receptor or C1q binding. [Wawrzynczak et al., (1992) Molecular Immunology 29:221]. Site-directed mutagenesis studies using a murine IgG1 Fc region suggested that the site of the IgG1 Fc region that controls the catabolic rate is located at the CH2-CH3 domain interface. Fc regions can be modified at the catabolic site to optimize the half-life of the fusion proteins. The Fc region used for the fusion proteins of the present invention may be derived from an IgG1 or an IgG4 Fc region, and may contain both the CH2 and CH3 regions including the hinge region.

Fc-IFN beta fusion proteins are described in WO 2006/000448, which is incorporated by reference.

Heterologous Albumin Fusion Proteins

Interferon beta described herein may be fused directly or via a peptide linker, water soluble polymer, or prodrug linker to albumin or an analog, fragment, or derivative thereof. Generally, the albumin proteins that are part of the fusion proteins of the present invention may be derived from albumin cloned from any species, including human. Human serum albumin (HSA) consists of a single non-glycosylated polypeptide chain of 585 amino acids with a formula molecular weight of 66,500. The amino acid sequence of human HSA is known [See Meloun, et al. (1975) FEBS Letters 58:136; Behrens, et al. (1975) Fed. Proc. 34:591; Lawn, et al. (1981) Nucleic Acids Research 9:6102-6114; Minghetti, et al. (1986) J. Biol. Chem. 261:6747, each of which are incorporated by reference herein]. A variety of polymorphic variants as well as analogs and fragments of albumin have been described. [See Weitkamp, et al., (1973) Ann. Hum. Genet. 37:219]. For example, in EP 322,094, various shorter forms of HSA. Some of these fragments of HSA are disclosed, including HSA(1-373), HSA(1-388), HSA(1-389), HSA(1-369), and HSA(1-419) and fragments between 1-369 and 1-419. EP 399,666 discloses albumin fragments that include HSA(1-177) and HSA(1-200) and fragments between HSA(1-177) and HSA(1-200).

It is understood that the heterologous fusion proteins of the present invention include interferon beta compounds that are coupled to any albumin protein including fragments, analogs, and derivatives wherein such fusion protein is biologically active and has a longer plasma half-life than the interferon beta compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the interferon beta compound of interest.

The heterologous fusion proteins of the present invention encompass proteins having conservative amino acid substitutions in the interferon beta compound and/or the Fc or albumin portion of the fusion protein. A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Except as otherwise specifically provided herein, conservative substitutions are preferably made with naturally occurring amino acids.

Wild-type albumin and immunoglobulin proteins can be obtained from a variety of sources. For example, these proteins can be obtained from a cDNA library prepared from tissue or cells which express the mRNA of interest at a detectable level. Libraries can be screened with probes designed using the published DNA or protein sequence for the particular protein of interest. For example, immunoglobulin light or heavy chain constant regions are described in Adams, et al. (1980) Biochemistry 19:2711-2719; Goughet, et al. (1980) Biochemistry 19:2702-2710; Dolby, et al. (1980) Proc. Natl. Acad. Sci. USA 77:6027-6031; Rice et al. (1982) Proc. Natl. Acad. Sci. USA 79:7862-7862; Falkner, et al. (1982) Nature 298:286-288; and Morrison, et al. (1984) Ann. Rev. Immunol. 2:239-256. Some references disclosing albumin protein and DNA sequences include Meloun, et al. (1975) FEBS Letters 58:136; Behrens, et al. (1975) Fed. Proc. 34:591; Lawn, et al. (1981) Nucleic Acids Research 9:6102-6114; and Minghetti, et al. (1986) J. Biol. Chem. 261:6747.

Characterization of the Heterologous Fusion Proteins of the Present Invention

Numerous methods exist to characterize the fusion proteins of the present invention. Some of these methods include, but are not limited to: SDS-PAGE coupled with protein staining methods or immunoblotting using anti-IgG or anti-HSA antibodies. Other methods include matrix assisted laser desorption/ionization-mass spectrometry (MALDI-MS), liquid chromatography/mass spectrometry, isoelectric focusing, analytical anion exchange, chromatofocusing, and circular dichroism, for example.

Enhancing Affinity for Serum Albumin

Various molecules can also be fused to the IFN beta polypeptides of the invention to modulate the half-life of IFN beta polypeptides in serum. In some embodiments, molecules are linked or fused to IFN beta polypeptides of the invention to enhance affinity for endogenous serum albumin in an animal.

For example, in some cases, a recombinant fusion of a IFN beta polypeptide and an albumin binding sequence is made. Exemplary albumin binding sequences include, but are not limited to, the albumin binding domain from streptococcal protein G (see. e.g., Makrides et al., J. Pharmacal. Exp. Ther. 277:534-542 (1996) and Sjolander et al., J, Immunol. Methods 201:115-123 (1997)), or albumin-binding peptides such as those described in, e.g., Dennis, et al., J. Biol. Chem. 277:35035-35043 (2002).

In other embodiments, the IFN beta polypeptides of the present invention are acylated with fatty acids. In some cases, the fatty acids promote binding to serum albumin. See, e.g., Kurtzhals, et al., Biochem. J. 312:725-731 (1995).

In other embodiments, the IFN beta polypeptides of the invention are fused directly with serum albumin (including but not limited to, human serum albumin). Those of skill in the art will recognize that a wide variety of other molecules can also be linked to IFN beta in the present invention to modulate binding to serum albumin or other serum components.

X. Glycosylation of IFN Beta Polypeptides

The invention includes IFN beta polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to IFN beta polypeptides either in vivo or in vitro. In some embodiments of the invention, a IFN beta polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the IFN beta polypeptide. See, e.g., H. Liu, et al. J. Am. Chem. Soc. 125: 1702-1703 (2003).

In some embodiments of the invention, a IFN beta polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid.

In some embodiments of the invention, a IFN beta polypeptide comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

WO 2007/022799 describe processes for producing recombinant human IFN beta under serum-free culture conditions and purification of IFN beta with a unique glycosylation pattern.

XI. IFN beta Dieters and Multimers

The present invention also provides for IFN beta and IFN beta analog combinations such as homodimers, heterodimers, homomultimers, or heteromultimers (i.e., trimers, tetramers, etc.) where IFN beta containing one or more non-naturally encoded amino acids is bound to another IFN beta or IFN beta variant thereof or any other polypeptide that is not IFN beta or IFN beta variant thereof, either directly to the polypeptide backbone or via a linker. Due to its increased molecular weight compared to monomers, the IFN beta dimer or multimer conjugates may exhibit new or desirable properties, including but not limited to different pharmacological, pharmacokinetic, pharmacodynamic, modulated therapeutic half-life, or modulated plasma half-life relative to the monomeric IFN beta. In some embodiments, IFN beta dimers of the invention will modulate signal transduction of the IFN receptor. In other embodiments, the IFN beta dimers or multimers of the present invention will act as a IFN receptor antagonist, agonist, or modulator.

In some embodiments, one or more of the IFN beta molecules present in a IFN beta containing dimer or multimer comprises a non-naturally encoded amino acid linked to a water soluble polymer.

In some embodiments, the IFN beta polypeptides are linked directly, including but not limited to, via an Asn-Lys amide linkage or Cys-Cys disulfide linkage. In some embodiments, the IFN beta polypeptides, and/or the linked non-IFN beta molecule, will comprise different non-naturally encoded amino acids to facilitate dimerization, including but not limited to, an alkyne in one non-naturally encoded amino acid of a first IFN beta polypeptide and an azide in a second non-naturally encoded amino acid of a second molecule will be conjugated via a Huisgen [3+2] cycloaddition. Alternatively, IFN beta, and/or the linked non-IFN beta molecule comprising a ketone-containing non-naturally encoded amino acid can be conjugated to a second polypeptide comprising a hydroxylamine-containing non-naturally encoded amino acid and the polypeptides are reacted via formation of the corresponding oxime.

Alternatively, the two IFN beta polypeptides, and/or the linked non-IFN beta molecule, are linked via a linker. Any hetero- or homo-bifunctional linker can be used to link the two molecules, and/or the linked non-IFN beta molecules, which can have the same or different primary sequence. In some cases, the linker used to tether the IFN beta, and/or the linked non-IFN beta molecules together can be a bifunctional PEG reagent. The linker may have a wide range of molecular weight or molecular length. Larger or smaller molecular weight linkers may be used to provide a desired spatial relationship or conformation between IFN beta and the linked entity or between IFN beta and its receptor, or between the linked entity and its binding partner, if any. Linkers having longer or shorter molecular length may also be used to provide a desired space or flexibility between IFN beta and the linked entity, or between the linked entity and its binding partner, if any.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more IFN beta polypeptide, formed by reactions with water soluble activated polymers that have the structure:

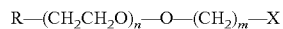

$$R\text{—}(CH_2CH_2O)_n\text{—}O\text{—}(CH_2)_m\text{—}X$$

wherein n is from about 5 to 3,000, in is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, dimes, mesylates, tosylates, and tresylate, alkene, and ketone.

XII. Measurement of IFN Beta Polypeptide Activity and Affinity of IFN Beta Polypeptide for the IFN Receptor IFN beta polypeptide activity can be determined using standard or known in vitro or in vivo assays. IFN beta polypeptides may be analyzed for biological activity by suitable methods known in the art. Such assays include, but are not limited to, activation of interferon-responsive genes, receptor binding assays, anti-viral activity assays, cytopathic effect inhibition assays, (Familletti et. al., Meth. Enzymol. 78:387-394), anti-proliferative assays, (Aebersold and Sample, Meth. Enzymol. 119:579-582), immunomodulatory assays (U.S. Pat. Nos. 4,914,033; 4,753,795), and assays that monitor the induction of MHC molecules (e.g., Hokland et al, Meth. Enzymol. 119:688-693), as described in Meager, J. Immunol. Meth., 261:21-36 (2002).

IFN beta polypeptides may be analyzed for their ability to activate interferon-sensitive signal transduction pathways. One example is the interferon-stimulated response element (ISRE) assay. Cells which constitutively express the type I interferon receptor (for example Hela cells, 293T cells) are transiently transfected with an ISRE-luciferase vector (pISRE-luc, Clontech). After transfection, the cells are treated with an interferon beta polypeptide. A number of protein concentrations, for example from 0.0001-10 ng/mL, are tested to generate a dose-response curve. If the interferon beta polypeptide binds and activates the IFN receptor, the resulting signal transduction cascade induces luciferase expression. Luminescence can be measured in a number of ways, for example by using a TOPCOUNT™ or FUSION™ microplate reader and STEADY-GLO® Luciferase Assay System (Promega).

IFN beta polypeptides may be analyzed for their ability to bind to the type I interferon receptor (IFNAR). The IFN receptor can be prepared using techniques and methods that are known to one of ordinary skill in the art. The hIFN receptor can be prepared as described in U.S. Pat. Nos. 6,566,132; 5,889,151; 5,861,258; 5,731,169; 5,578,707, which is incorporated by reference herein. For example, cells or cell lines that modulate growth or MHC Class I or II antigen production in response to hIFN or bind hIFN (including but not limited to, cells containing active IFN receptors such as human lymphoblastoid Daudi cells, or recombinant IFN receptor producing cells) can be used to monitor hIFN receptor binding. For a non-PEGylated or PEGylated IFN beta polypeptide comprising a non-natural amino acid, the affinity of IFN beta for its receptor can be measured by using a BIACORE® biosensor (Pharmacia). Suitable binding assays include, but are not limited to, BIACORE® assays (Pearce et al., Biochemistry 38:81-89 (1999)) and ALPHASCREEN® assays (PerkinElmer). ALPHASCREEN® is a bead-based non-radioactive luminescent proximity assay where the donor beads are excited by a laser at 680 nm to release singlet oxygen. The singlet oxygen diffuses and reacts with the thioxene derivative on the surface of acceptor beads leading to fluorescence emission at ~600 nm. The fluorescence emission occurs only when the donor and acceptor beads are brought into close proximity by molecular interactions occurring when each is linked to ligand and receptor respectively. This ligand-receptor interaction can be competed away using receptor-binding variants while non-binding variants will not compete.

Regardless of which methods are used to create the present hIFN analogs, the analogs are subject to assays for biological activity. Tritiated thymidine assays may be conducted to ascertain the degree of cell division. Other biological assays, however, may be used to ascertain the desired activity. IFN beta polypeptides may be analyzed for their antiviral activity and/or antiproliferative activity. Antiproliferative assays are know to those of ordinary skill of the art. Basu et al. in Bioconjugate Chem (2006) 17:618-630 describe an anti-proliferation assay using A549 cells and MTT to measure proliferation. Biological assays such as assaying for the ability to inhibit viral replication, also provides indication of IFN activity. Assays known to one of ordinary skill of the art may be also used to assess the biological activity and potential side effects of IFN beta polypeptides of the invention.

Platanias et al. in Experimental Hematology 1999; 27:1583-1592, which is incorporated by reference herein, discuss signaling pathways activated by interferons including the Jak-Stat pathway. Assays evaluating signaling and pathways downstream from interferon receptor binding may be used to evaluate IFN polypeptides of the invention.

Viral replication assays or in vivo studies may be performed with IFN beta polypeptides of the invention to screen for anti-viral activity. Viral replication assays are known to those skilled in the art and may involve HCV (Hepatitis C Virus), VSV (Vesicular Stomatitis Virus), or EMCV (Encephalomyocarditis Virus). The reduction of cytopathic effect (CPE) of cells such as baby hamster kidney BHK21 cells infected with VSV may also be measured with IFN beta polypeptides. Various cell lines and calculation algorithms may be used to determine potency in CPE assays. Comparisons are made with known reference standards and international units may be calculated. Other in vitro assays may be used to ascertain biological activity. In general, the test for biological activity should provide analysis for the desired result, such as increase or decrease in biological activity (as compared to non-altered IFN beta), different biological activity (as compared to non-altered IFN beta), receptor affinity analysis, or serum half-life analysis.

Other assays include, but are not limited to, antibody neutralization of antiviral activity, induction of protein kinase, oligoadenylate 2,5-A synthetase or phosphodiesterase activities (EP 41313 which is incorporated by reference herein); immunomodulatory assays (U.S. Pat. No. 4,753,795, which is incorporated by reference herein), growth inhibition assays, and binding assays with cells that express interferon receptors (U.S. Pat. No. 7,144,574, which is incorporated by reference herein).

Regardless of which methods are used to create the IFN beta polypeptides, the IFN beta polypeptides are subject to assays for biological activity. In general, the test for biological activity should provide analysis for the desired result, such as increase or decrease in biological activity (as compared to modified IFN beta), different biological activity (as compared to modified IFN beta), receptor or binding partner affinity analysis, conformational or structural changes of the IFN beta itself or its receptor (as compared to the modified IFN beta), or serum half-life analysis.

The above compilation of references for assay methodologies is not exhaustive, and those of ordinary skill in the art will recognize other assays useful for testing for the desired end result. Alterations to such assays are known to those of ordinary skill in the art.

Measurement of Antibody Formation to Polypeptides and Preclinical Testing for Immunogenicity Assays to measure and assess antibody formation include, but are not limited to, bioassays and binding assays. Bioassays include but are not limited to, assays that use serum from animal subjects or patients to detect neutralizing antibodies. The ability of the serum to neutralize the biological activity of the exogenous molecule is measured. Cell-based bioassays, for example, may measure proliferation, cytotoxicity, signaling, or cytokine release. Binding assays that detect both neutralizing and non-neutralizing antibodies measure the ability of serum to bind to exogenous protein. Methods for measuring such antibodies include but are not limited to, ELISA. The significance of the presence of both of these antibodies is discussed in Schellekens, H et al. Clinical Therapeutics 2002; 24(11):1720-1740, which is incorporated by reference herein.

Schellekens, H et al. Clinical Therapeutics 2002; 24(10: 1720-1740, which is incorporated by reference in its entirety, also discuss animal testing in non-human primates and in transgenic mouse models that express the endogenous human protein as well as in vitro testing methods. Whiteley et al. in J. Clin. Invest. 1989; 84:1550-1554, which is incorporated by reference herein, discuss the use of transgenic mice in immunogenicity studies with human insulin. Wadhwa, M. et al. J of Immunol Methods 2003; 278:1-17, which is incorporated by reference herein, discusses a number of techniques for detection and measurement of immunogenicity such as surface plasmon resonance (SPR; Biacore), radioimmunoprecipitation assays (RIPA), immunoassays such as solid phase binding immunoassays, bridging and competitive ELISA, and immunoblotting. Other techniques include but are not limited to electrochemiluminescence (ECL).

Chirino et al. DDT 2004; 9(2):82-90, which is incorporated by reference herein, describe ex vivo T cell activation assays for investigating the immunogenicity of protein therapeutics. Uptake of wild type and variant interferon proteins by antigen presenting cells is monitored. Ex vivo T-cell activation assays may be used to experimentally quantitate immunogenicity. In this method, antigen presenting cells and naive T cells from matched donors are challenged with a peptide or whole protein of interest one or more times. Then, T cell activation can be detected using a number of methods, for example by monitoring production of cytokines or measuring uptake of tritiated thymidine, Other suitable T-cell assays include those disclosed in Meidenbauer, et al. Prostate 43, 88-100 (2000); Schultes, B. C and Whiteside, T. L., J. Immunol. Methods 279, 1-15 (2003); and Stickler, et al., J. Immunotherapy, 23, 654-660 (2000). PBMC donors used for the above-described T-cell activation assays may comprise class II MHC alleles that are common in patients requiring treatment for interferon beta responsive disorders. For example, for most diseases and disorders, it is desirable to test donors comprising all of the alleles that are prevalent in the population. However, for diseases or disorders that are linked with specific MHC alleles, it may be more appropriate to focus screening on alleles that confer susceptibility to interferon beta responsive disorders. The MHC haplotype of PBMC donors or patients that raise an immune response to interferon beta may be compared with the MHC haplotype of patients who do not raise a response. This data may be used to guide preclinical and clinical studies as well as aiding in identification of patients who will be especially likely to respond favorably or unfavorably to the interferon beta therapeutic. Immunogenicity may be measured in transgenic mouse systems. For example, mice expressing fully or partially human class II MHC molecules may be used. Immunogenicity may be tested by administering the interferon beta variants to one or more animals, including rodents and primates, and monitoring for antibody formation. Non-human primates with defined MHC haplotypes may be especially useful, as the sequences and hence peptide binding specificities of the MHC molecules in non-human primates may be very similar to the sequences and peptide binding specificities of humans. Similarly, genetically engineered mouse models expressing human MHC peptide-binding domains may be used (see for example Sonderstrup et. al. Immunol. Rev. 172: 335-343 (1999) and Forsthuber et. al. J. Immunol. 167: 119-125 (2001)).

Additional methods for assessing polypeptides of the invention are known to those of ordinary skill in the art.

XIII. Measurement of Potency, Functional In Vivo Half-Life, and Pharmacokinetic Parameters An important aspect of the invention is the prolonged biological half-life that is obtained by construction of the IFN beta polypeptide with or without conjugation of the polypeptide to a water soluble polymer moiety. The rapid post administration decrease of IFN beta polypeptide serum concentrations has made it important to evaluate biological responses to treatment with conjugated and non-conjugated IFN beta polypeptide and variants thereof. The conjugated and non-conjugated IFN beta polypeptide and variants thereof of the present invention may have prolonged serum half-lives also after administration via, e.g. subcutaneous or i.v. administration, making it possible to measure by, e.g. ELISA method or by a primary screening assay. ELISA or RIA kits from commercial sources may be used such as Invitrogen (Carlsbad, Calif.). Measurement of in vivo biological half-life is carried out as described herein.

The potency and functional in vivo half-life of an IFN beta polypeptide comprising a non-naturally encoded amino acid can be determined according to protocols known to those of ordinary skill in the art.

Pharmacokinetic parameters for a IFN beta polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a IFN beta polypeptide comprising a non-naturally encoded amino acid not conjugated to a water soluble polymer and about 4 days for a IFN beta polypeptide comprising a non-naturally encoded amino acid and conjugated to a water soluble polymer. Pharmacokinetic data for IFN beta without a non-naturally encoded amino acid can be compared directly to the data obtained for IFN beta polypeptides comprising a non-naturally encoded amino acid.

Basu et al. in Bioconjugate Chem (2006) 17:618-630 describe pharmacokinetic and immunogenicity studies of IFN beta polypeptides in mice and rats. Pharmacokinetic parameters can also be evaluated in a primate, e.g., cynomolgus monkeys. Typically, a single injection is administered either subcutaneously or intravenously, and serum IFN beta levels are monitored over time.

The specific activity of IFN beta polypeptides in accordance with this invention can be determined by various assays known in the art. The biological activity of the IFN beta polypeptide muteins, or fragments thereof, obtained and purified in accordance with this invention can be tested by methods described or referenced herein or known to those of ordinary skill in the art.

IFN beta polypeptides may be analyzed for their efficacy in treating an animal model of disease, such as the mouse or rat EAE model for multiple sclerosis. An animal model such as the commonly used experimental autoimmune encephalomyelitis (RAE) model can be used to establish efficacy of a polypeptide of the invention. In the EAE model, immunization with myelin or myelin derived proteins elicits a disease mimicking the majority of the inflammatory and neurologic features of multiple sclerosis in humans. EAE has been used in mice, rats, rabbits, and marmosets (Cannella et al. PNAS, 95, 10100 5, 1998, Zaprianova et al. Morfologiia, 112, 25 8, 1997, Hassouna et al. J. Urology, 130, 806 10, 1983, Genain & Hauser J. Mol. Med. 75, 187 97, 1997). Other models include Theiler's murine encephalomyelitis virus (TMEV) model (Murray et al. J. Neurosci. 18, 7306 14, 1998), may be used to establish efficacy of the IFN beta polypeptide.

XIV Administration and Pharmaceutical Compositions

The polypeptides or proteins of the invention (including but not limited to, IFN beta, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention. Compositions may be in a water-soluble form, such as being present as pharmaceutically acceptable salts, which is meant to include both acid and base addition salts.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of a IFN beta polypeptide modified to include one or more unnatural amino acids to a natural amino acid IFN beta polypeptide and comparison of a IFN beta polypeptide modified to include one or more unnatural amino acids to a currently available IFN beta treatment), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

IFN beta polypeptides of the invention may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The IFN beta polypeptide, may be used alone or in combination with other suitable components such as a pharmaceutical carrier. The IFN beta polypeptide may be used in combination with other agents or therapeutics.

The IFN beta polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of IFN beta can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs e.g. IFN beta, interleukins, antibodies, FGFs, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acid polypeptides at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human IFN beta polypeptides of the invention can be administered directly to a mammalian subject. Administration is by any of the routes normally used for introducing IFN beta polypeptide to a subject. The IFN beta polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces), pulmonary, intraocular, intranasal, and transdermal administration, although the most suitable route in any given case will depend on the nature and severity of the condition being treated. Administration can be either local or systemic. The formulations of compounds can be presented in unit-dose or multi-dose sealed containers, such as ampoules and vials. IFN beta polypeptides of the invention can be prepared in a mixture in a unit dosage injectable form (including but not limited to, solution, suspension, or emulsion) with a pharmaceutically acceptable carrier. IFN beta polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions and formulations of the invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, 17$^{th}$ ed. 1985)).

Suitable carriers include but are not limited to, buffers containing succinate, phosphate, borate, HEPES, citrate, histidine, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium and sodium chloride; fillers such as microcrystalline cellulose, lactose, corn and other starches; binding agents; sweeteners and other flavoring agents; coloring agents; and/or nonionic surfactants including but not limited to TWEEN™ (including but not limited to, Tween 80 (polysorbate 80) and Tween 20 (polysorbate 20), PLURONICS® and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names PLURONICS®, R-PLURONICS®, TETRONICS® and R-TETRONICS® (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated IFN beta against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, benzalkonium chloride, metacresol, methyl/propyl parabene, cresol, and phenol, or a combination thereof. U.S. Pat. No. 7,144,574, which is incorporated by reference herein, describe additional materials that may be suitable in pharmaceutical compositions and formulations of the invention and other delivery preparations.

IFN beta polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers,* 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. All references and patents cited are incorporated by reference herein.

Liposomally entrapped IFN beta polypeptides can be prepared by methods described in, e.g., DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003). All references and patents cited are incorporated by reference herein. A number of formulations of IFN beta have been described, including but not limited to, intranasal formulations, hydrogel formulations, and liquid formulations (see WO 2005/120551, WO 2005/110466, and WO 2005/058346 which are incorporated by reference herein). Other formulations are discussed in WO 95/31479 and WO 95/31213, which are incorporated by reference herein.

The dose administered to a patient in the context of the present invention should be sufficient to cause a beneficial response in the subject over time. Generally, the total pharmaceutically effective amount of the IFN beta polypeptide of the present invention administered parenterally per dose is in the range of about 0.01 μg/kg/day to about 100 μg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available IFN beta polypeptide products approved for use in humans. Generally, a PEGylated IFN beta polypeptide of the invention can be administered by any of the routes of administration described above.

XV. Therapeutic Uses of IFN Beta Polypeptides of the Invention

The IFN beta polypeptides of the invention are useful for treating a wide range of disorders.

IFN beta polypeptides of the invention may be administered to individuals with multiple sclerosis. It may be used as a treatment for a variety of malignancies, cancers, tumors or tumour angiogenesis, such as acute myeloid leukemia, multiple myeloma, Hodgkin's disease, basal cell carcinoma, ovarian carcinoma, cervical dysplasia, cervical carcinoma, laryngeal papillomatosis, mycosis fungoides, glioma, acute myeloid leukemia, multiple myeloma, Hodgkin's disease, melanoma, breast carcinoma, non-small cell lung cancer, malignant melanoma (adjuvant, late stage, as well as prophylactic), carcinoid tumour, B-cell lymphoma, T-cell lymphoma, follicular lymphoma, Kaposi's sarcoma, chronic myelogenous leukaemia, renal cell carcinoma, recurrent superficial bladder cancer, colorectal carcinoma, hairy cell leukaemia, and osteosarcoma. IFN beta may be used as a therapeutic agent against a variety of viral infections, including but not limited to viral hepatitis, herpes zoster and genitalia, papilloma viruses, viral encephalitis, cytomegalovirus pneumonia, herpetic keratitis, herpes simplex, rhinovirus chronic persistent hepatitis, chronic active HCV (type I), chronic active HCV (type II) and chronic hepatitis B, ulcerative colitis, Guillain-Barre syndrome, glioma, idiopathic pulmonary fibrosis, abnormal cell growth, or for immunomodulation.

IFN beta polypeptides of the invention may be used for the treatment of multiple sclerosis (MS), such as any of the generally recognized four types of MS (benign, relapsing remitting MS (RIMS), primary progressive MS (PPMS) and secondary progressive MS (SPMS)) and for monosymptomatic MS), cancer or tumours, hepatitis, e.g. hepatitis B and hepatitis C, or a herpes infection (the latter treatment optionally being combined with a treatment with IL-10).

Also, the invention includes a method of treating a mammal that has circulating antibodies against IFN beta 1a, e.g. AVONEX® or REBIF®, or against IFN beta 1b, e.g. BETASERON®. Such method involves the administration of an effective amount of a MN beta polypeptide that has a reduced or no reaction with said antibodies. The mammals to be treated may suffer from any of the diseases listed above or any condition in which IFN beta is a useful treatment. Also included in this invention is a method of making a pharmaceutical product for use in treatment of mammals having circulating antibodies against IFN beta 1a, e.g. AVONEX® or REBIF®, or against IFN beta 1b, e.g. BETASERON®. IFN beta polypeptides of the present invention that have a reduced reaction or no reaction with such circulation antibodies (e.g. the reaction is reduced by at least about 25%, at least about 50%, at least about 75% or at least about 100% (i.e. no reaction) is formulated into an injectable or otherwise suitable formulation. Antibodies, in particular neutralizing antibodies, formed in a mammal in response to having been treated with any of the commercially available IFN beta preparations (REBIF®, BETASERON®, AVONEX®) may be referred to as "circulating antibodies."

WO 2007/042602, which is incorporated by reference herein, describes the use of IFN beta for the prevention or treatment of ischemia reperfusion injury or multi-organ failure. Several conditions, including abdominal injuries, bowel infraction, cardiovascular surgery and shock, can lead to intestinal ischemia-reperfusion injury (IRI). Besides causing local injury, IRI also triggers systemic inflammatory response in remote organs resulting in a syndrome called multi-organ failure. In this syndrome lungs are especially vulnerable. US patent publication no. US 2004/0105843, which is incorporated by reference herein, describes the use of interferon beta in hypoxia/ischemia related blood flow resistance in a patient.

WO 2007/025991, which is incorporated by reference herein, describe a method for treating a patient having demyelinating optic neuritis (DON) comprising the sequential or simultaneous administration of a steroid compound and an interferon-beta protein. Also, patients with manifestations of early ON (optic neuritis) appeared to benefit with IFN beta treatment.

WO2006/064026, which is incorporated by reference herein, describe the use of IFN beta to treat HCV infected individuals who have not received previous treatment with IFN alpha.

WO 2003/075944 describe interferon beta-like polypeptides for treatment of stroke or transient ischemic attack. IFN beta combined with other agents may be used, including interferon beta in conjunction with factor XIII to treat inflammatory bowel disease e.g. ulcerative colitis and Crohn's diseases; IFN beta with an IL-2R antagonist for autoimmune diseases such as multiple sclerosis; or IFN beta with ribavirin (see WO 2004/017921; WO 2004/002500; WO 2004/075903, which are incorporated by reference herein). IFN beta polypeptides may be used for CML monotherapy, B cell lymphoma monotherapy, follicular lymphoma therapy, hepatitis C monotherapy, multiple myeloma monotherapy, or renal carcinoma monotherapy. IFN beta polypeptides may be used in combination with cytarabine for CML therapy, in combination with doxorubicin-based regimens for B cell lymphoma therapy, as an adjunct to CHOP-like region for follicular lymphoma therapy, in combination with ribavirin for hepatitis C therapy, in combination with VBMCP, BCNU or VBMCP+HiCy for multiple myeloma therapy, or in combination with Vinblastine, floxuridine, 5-fluoruouracil or IL-10 for renal carcinoma therapy.

Average quantities of the IFN beta may vary and in particular should be based upon the recommendations and prescription of a qualified physician. The exact amount of IFN beta is a matter of preference subject to such factors as the exact type of condition being treated, the condition of the patient being treated, as well as the other ingredients in the composition. The invention also provides for administration of a therapeutically effective amount of another active agent. The amount to be given may be readily determined by one of ordinary skill in the art based upon therapy with IFN beta.

Pharmaceutical compositions of the invention may be manufactured in a conventional manner.

EXAMPLES

The following examples are offered to illustrate, but do not to limit the claimed invention.

Example 1

This example describes some of the many potential sets of criteria for the selection of sites of incorporation of non-naturally encoded amino acids into IFN beta.

Based on analysis of the crystal structure with PDB ID 1AU1, seven sites were selected: 28, 36, 76, 80, 107, 108, and 111 for substitution with the non-naturally encoded amino acid p-acetylphenylalanine. See FIG. 1. Residue 80 (N80) is a glycosylation site. In some embodiments, one or more non-naturally encoded amino acids are incorporated at one or more of the following positions of IFN beta: 28, 36, 76, 80, 107, 108, 111, and any combination thereof of SEQ ID NO: 1 or the corresponding amino acids in SEQ ID NOs: 3, 4. In some embodiments, the non-naturally occurring amino acid at one or more of these positions is linked to a water soluble polymer, including but not limited to, positions: 28, 36, 76, 80, 107, 108, 111, and any combination thereof of SEQ ID NO: 1 or the corresponding amino acids in SEQ ID NOs: 3, 4.

In a separate analysis, average Cx values were calculated for interferon beta based on the crystal structure PDB ID 1AU1. Using the Cx program (Pintar et al. (2002) Bioinformatics, 18, pp 980), the extent of protrusion for each protein atom was evaluated. The coordinates for this structure is available from the Protein Data Bank (PDB) (Bernstein et al. *J. Mol. Biol.* 1997, 112, pp 535). Karpusas, M., Nolte, M., Benton, C. B., Meier, W., Lipscomb, W. N., Goelz, S. describe the crystal structure of human interferon beta in Proc Natl Acad Sci 1997 94:11813-11818. The following criteria were used to evaluate each position of interferon beta for the introduction of a non-naturally encoded amino acid: the residue (a) should not interfere with binding of the IFN Receptor based on structural analysis, b) should not be affected by alanine or homolog scanning mutagenesis (c) should be surface exposed and exhibit minimal van der Waals or hydrogen bonding interactions with surrounding residues, (d) should be either deleted or variable in interferon beta variants, (e) would result in conservative changes upon substitution with a non-naturally encoded amino acid and (f) could be found in either highly flexible regions or structurally rigid regions.

The following represents the residues involved with the different helices: residues 2-22 (helix A); residues 51-71 (helix B); residues 80-107 (helix C); residues 118-136 (helix D); and residues 139-162 (helix E). The AB loop can be represented as segments—AB1 (residues 23-35); AB2 (residues 36-40); and AB3 (residues 41-50). Interferon beta is glycosylated at position 80 (Asn80). A free cysteine is at position 17 (Cys17) in the wild-type sequence of interferon beta. The neutralizing antibody binding region is residues 41-49. There are two putative binding regions for the IFN receptor (IFN alpha R2): 1) residues 25-35 and 2) residues 121-135. The putative binding region for IFN alpha R1 is: residues 80-100.

In some embodiments, one or more non-naturally encoded amino acids are incorporated in one or more of the following positions in IFN beta: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4).

Figure 2:
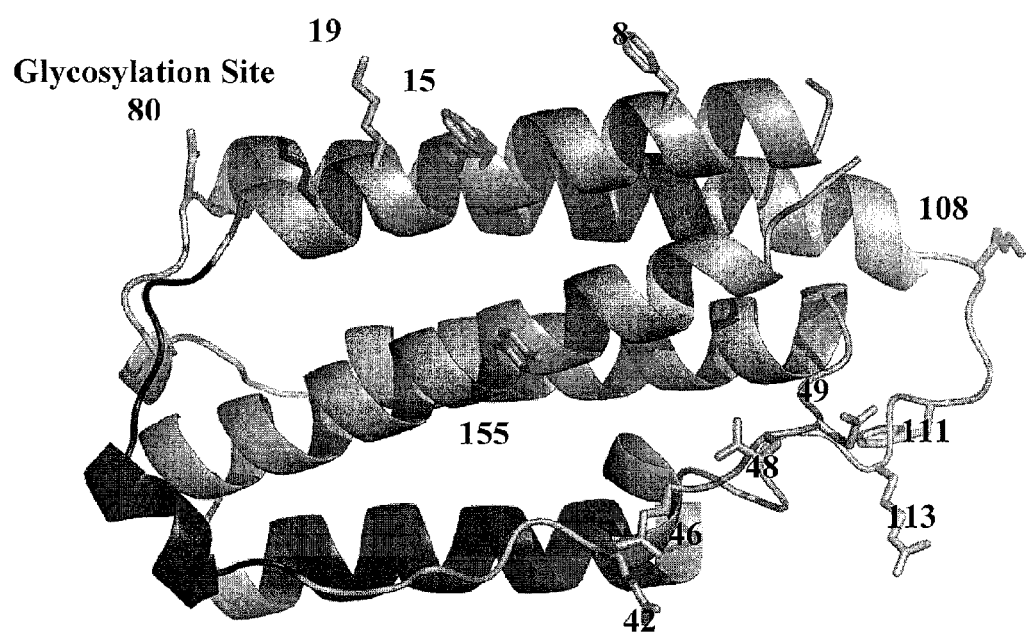
FIG. 2—A model of the crystal structure of IFN beta is shown. Selected sites for substitution with a non-naturally encoded amino acid are shown.

In some embodiments, one or more non-naturally encoded amino acids are incorporated at any position in one or more of the following regions corresponding to secondary structures in interferon beta as follows: Helix A (2-22); Helix B (51-71); Helix C (80-107); Helix D (118-136); helix E (139-162); AB loop: AB1 (23-35); AB2 (36-40); AB3 (41-50) from SEQ ID NO: 1 or the corresponding amino acids of SEQ ID NOs: 3, 4. In other embodiments, the non-naturally encoded amino acid is substituted at a position selected from the group consisting of residues 25-35, 80-100, and 121-135 of interferon beta (SEQ ID NO: 1 or the corresponding amino acids from SEQ ID NO: 3, 4). In other embodiments, the non-naturally encoded amino acid is substituted at a position selected from the group consisting of residues 41-49 from interferon beta from SEQ ID NO: 1 or the corresponding amino acids from SEQ ID NO: 3, 4. In some embodiments, one or more non-naturally encoded amino acids are incorporated at one or more of the following positions of IFN beta: 8, 15, 19, 36, 42, 46, 48, 49, 80, 108, 111, 113, 155, and any combination thereof of SEQ ID NO: 1 or the corresponding amino acids in SEQ ID NOs: 3, 4. See FIGS. 1 and 2 and Table 2. In some embodiments, one or more non-naturally encoded amino acids are incorporated at one or more of the following positions of IFN beta: 15, 42, 80, 108, 111, 155, and any combination thereof (SEQ ID NO: 1 or the corresponding amino acids in SEQ ID NOs: 3, 4). In some embodiments, the polypeptide of the invention comprises one or more natural amino acid substitution, addition, or deletion. In some embodiments, the polypeptide of the invention comprises a C17S substitution (serine for a cysteine at position 17) of SEQ ID NO: 1 or the corresponding amino acids in SEQ ID NO: 3, 4. In some embodiments, the polypeptide of the invention comprises a C17S substitution (serine for a cysteine at position 17) and one or more natural amino acid substitution, addition, or deletion. In some embodiments, the polypeptide of the invention comprises one or more non-naturally encoded amino acid substitution, addition, or deletion in the signal sequence. In some embodiments, the polypeptide of the invention comprises one or more non-naturally encoded amino acid substitution, addition, or deletion in the signal sequence of SEQ ID NO: 4. In some embodiments, the polypeptide of the invention comprises one or more naturally encoded amino acid substitution, addition, or deletion in the signal sequence of SEQ ID NO: 4. In some embodiments, one or more non-natural amino acids are incorporated in the leader or signal sequence of SEQ ID NOs: 4 or other IFN beta sequence.

In some embodiments, the non-naturally occurring amino acid at one or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4 or the corresponding amino acids in another IFN beta sequence).

In some embodiments, the non-naturally occurring amino acid in one or more of these regions is linked to a water soluble polymer, including but not limited to: Helix A (2-22); Helix B (51-71); Helix C (80-107); Helix D (118-136); Helix E (139-162); AB loop: AB1 (23-35); AB2 (36-40); AB3 (41-50) from SEQ ID NO: 1 or the corresponding amino acids of SEQ ID NOs: 3, 4. In other embodiments, the non-naturally occurring amino acid in one or more of these regions is linked to a water soluble polymer, including but not limited to, residues 25-35, 80-100, and 121-135 of interferon beta (SEQ ID NO: 1 or the corresponding amino acids from SEQ ID NO: 3, 4). In other embodiments, the non-naturally occurring amino acid in one or more of these regions is linked to a water soluble polymer, including but not limited to, residues 41-49 from interferon beta from SEQ ID NO: 1 or the corresponding amino acids from SEQ ID NO: 3, 4. In some embodiments, the non-naturally occurring amino acid at one or more of these positions is linked to a water soluble polymer, including but not limited to, positions: 8, 15, 19, 36, 42, 46, 48, 49, 80, 108, 111, 113, 155, and any combination thereof (SEQ ID NO: 1 or the corresponding amino acids in SEQ ID NOs: 3, 4). In some embodiments, the non-naturally occurring amino acid at one or more of these positions is linked to a water soluble polymer, including but not limited to, positions: 15, 42, 80, 108, 111, 155, and any combination thereof (SEQ ID NO: 1 or the corresponding amino acids in SEQ ID NOs: 3, 4). In some embodiments, the non-naturally occurring amino acid in the signal or leader sequence is linked to a water soluble polymer (SEQ ID NO: 4 or other IFN beta sequence).

The amino acid sequence of IFN beta without a leader or signal sequence/peptide but with a C17S substitution is shown as SEQ ID NO: 1. The amino acid sequence of IFN beta without a leader or signal sequence/peptide and without a C17S substitution is shown as SEQ ID NO: 3. The amino acid sequence of IFN beta with a leader or signal sequence/peptide and without a C17S substitution is shown as SEQ ID NO: 4.

TABLE 2

| Residue # | Average Cx | Residue | Position | |
|---|---|---|---|---|
| 8 | 1.645714 | Phe8 | A Helix | |
| 15 | 1.508571 | Phe15 | A Helix | |
| 19 | 1.698 | Lys19 | A Helix | |
| 36 | 0.75 | Met36 | AB loop | |
| 42 | 1.942 | Glu42 | AB loop | Neutralizing Ab region |
| 46 | 1.878 | Gln46 | AB loop | Neutralizing Ab region |
| 48 | 1.86 | Gln48 | AB loop | Neutralizing Ab region |
| 49 | 2.642 | Gln49 | AB loop | Neutralizing Ab region |
| 80 | 1.46 | Asn80 | C Helix | |
| 108 | 3.99 | Lys108 | CD loop | |
| 111 | 2.484286 | Phe111 | D Helix | |
| 113 | 3.427143 | Arg113 | D Helix | |
| 155 | 1.27 | Tyr155 | E Helix | |

Example 2

This example details cloning and expression of a IFN beta polypeptide including a non-naturally encoded amino acid in *E. coli*. This example also describes methods to assess the biological activity of modified IFN beta polypeptides.

Methods for cloning IFN beta are known to those of ordinary skill in the art. Polypeptide and polynucleotide sequences for IFN beta and cloning of IFN beta into host cells as well as purification of IFN beta are detailed in Goeddel et al., Nucleic Acids Res. 8, 4057 (1980), U.S. Pat. Nos. 7,144,574; 6,531,111; 4,966,843; 5,376,567; 5,795,779; 7,144,574; 4,462,940; 4,894,330; 4,518,584; 5,702,699; 6,962,978; 5,814,485; 6,887,462; 6,800,735; 6,514,729; and U.S. Publication Nos. US2002/0137895, US2004/0115169, and US2005/0054053, all of which are incorporated by reference in their entirety herein.

cDNA encoding IFN beta without a leader or signal sequence and with a C17S substitution is shown as SEQ ID NO: 2. Modifications to the wild-type IFN gene sequence were made at the 5' end to make it more A-T rich at the first four codons. These modifications at the 5' end did not alter the amino acid sequence, The polypeptide encoded by this sequence is shown as SEQ ID NO: 1.

SEQ ID NO: 3 is an amino acid sequence of IFN beta without a leader or signal sequence and without a C17S substitution.

SEQ ID NO: 4 is an amino acid sequence of IFN beta with a leader sequence and without a C17S substitution.

Figure 3:
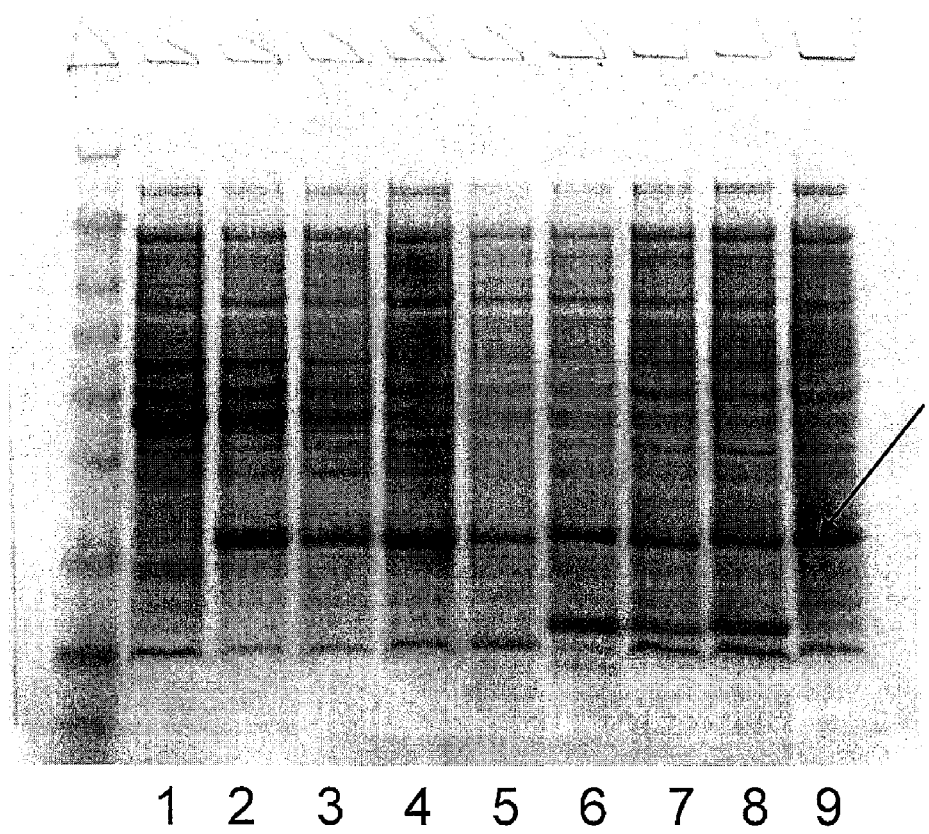
FIG. 3—SDS PAGE analysis of the expression of IFN beta polypeptides of the present invention is shown.

An introduced translation system that comprises an orthogonal tRNA (O-tRNA) and an orthogonal aminoacyl tRNA synthetase (O-RS) is used to express IFN beta containing a non-naturally encoded amino acid. The O-RS preferentially aminoacylates the O-tRNA with a non-naturally encoded amino acid. In turn the translation system inserts the non-naturally encoded amino acid into IFN beta, in response to an encoded selector codon. Suitable O-RS and O-tRNA sequences are described in WO 2006/068802 entitled "Compositions of Aminoacyl-tRNA Synthetase and Uses Thereof" (E9—SEQ ID NO: 5 & D286R mutant of E9—SEQ ID NO: 24) and WO 2007/021297 entitled "Compositions of tRNA and Uses Thereof" (F13; SEQ ID NO: 6), which are incorporated by reference in their entirety herein.

for example, refers to an IFN beta polypeptide with a para-acetylphenylalanine substitution at position 28 (leucine) (see SEQ ID NO: 3 for original sequence prior to substitution). The following IFN polypeptides shown in FIG. 3 did not have a C17S substitution: L28pAF, M36pAF, S76pAF, N80pAF, E107pAF, K108pAF, and F111pAF. The polynucleotide sequence obtained from CODA was not the native IFN beta polynucleotide sequence, though the IFN beta amino acid sequence resulting from the polynucleotide sequence was unaltered. For the sample shown in lane 9, the first four codons of the IFN beta polynucleotide sequence were modified so that this region was more A-T rich, though the IFN beta amino acid sequence was unaltered.

TABLE 3

O-RS and O-tRNA sequences.

| | | |
|---|---|---|
| SEQ ID NO: 7 | *M. jannaschii* mtRNA$_{CUA}^{Tyr}$ | tRNA |
| SEQ ID NO: 8 | HLAD03; an optimized amber supressor tRNA | tRNA |
| SEQ ID NO: 9 | HL325A; an optimized AGGA frameshift supressor tRNA | tRNA |
| SEQ ID NO: 10 | Aminoacyl tRNA synthetase for the incorporation of p-azido-L-phenylalanine p-Az-PheRS(6) | RS |
| SEQ ID NO: 11 | Aminoacyl tRNA synthetase for the incorporation of p-benzoyl-L-phenylalanine p-BpaRS(1) | RS |
| SEQ ID NO: 12 | Aminoacyl tRNA synthetase for the incorporation of propargyl-phenylalanine Propargyl-PheRS | RS |
| SEQ ID NO: 13 | Aminoacyl tRNA synthetase for the incorporation of propargyl-phenylalanine Propargyl-PheRS | RS |
| SEQ ID NO: 14 | Aminoacyl tRNA synthetase for the incorporation of propargyl-phenylalanine Propargyl-PheRS | RS |
| SEQ ID NO: 15 | Aminoacyl tRNA synthetase for the incorporation of p-azido-phenylatanine p-Az-PheRS(1) | RS |
| SEQ ID NO: 16 | Aminoacyl tRNA synthetase for the incorporation of p-azido-phenylalanine p-Az-PheRS(3) | RS |
| SEQ ID NO: 17 | Aminoacyl tRNA synthetase for the incorporation of p-azido-phenylalanine p-Az-PheRS(4) | RS |
| SEQ ID NO: 18 | Aminoacyl tRNA synthetase for the incorporation of p-azicio-phenylalanine p-Az-PheRS(2) | RS |
| SEQ ID NO: 19 | Aminoacyl tRNA synthetase for the incorporation of p-acetyl-phenylalanine (LW1) | RS |
| SEQ ID NO: 20 | Aminoacyl tRNA synthetase for the incorporation of p-acetyl-phenylalanine (LW5) | RS |
| SEQ ID NO: 21 | Aminoacyl tRNA synthetase for the incorporation of p-acetyl-phenylalanine (LW6) | RS |
| SEQ ID NO: 22 | Aminoacyl tRNA synthetase for the incorporation of p-azido-phenylalanine (AzPheRS-5) | RS |
| SEQ ID NO: 23 | Aminoacyl tRNA synthetase for the incorporation of p-azido-phenylalanine (AzPheRS-6) | RS |

The transformation of *E. coli* with plasmids containing the modified IFN beta polynucleotide sequence and the orthogonal aminoacyl tRNA synthetase/tRNA pair (specific for the desired non-naturally encoded amino acid) allows the site-specific incorporation of non-naturally encoded amino acid into the IFN beta polypeptide. Expression of IFN beta polypeptides was under control of the T7 promoter.

Suppression with Para-Acetyl-Phenylalanine (pAF)

Expression constructs were generated based on the polypeptide sequence shown as SEQ ID NO: 3. Each construct had an amber stop codon that would generate a IFN beta polypeptide with a non-naturally encoded amino acid substitution at one of these positions: 28, 36, 76, 80, 107, 108, 111.

Figure 4:
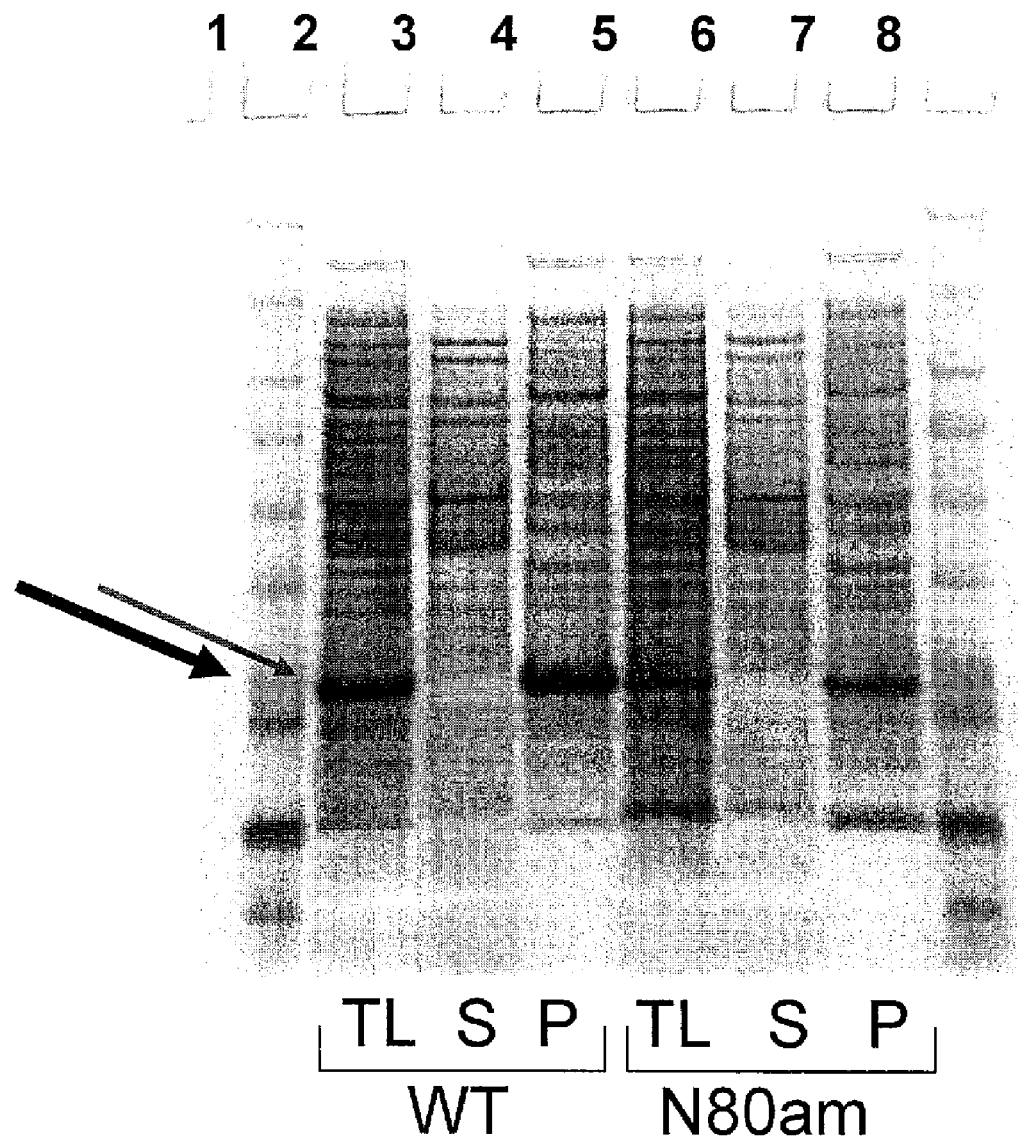
FIG. 4—SDS PAGE analysis of the expression of IFN beta polypeptides of the present invention is shown.
Figure 5:
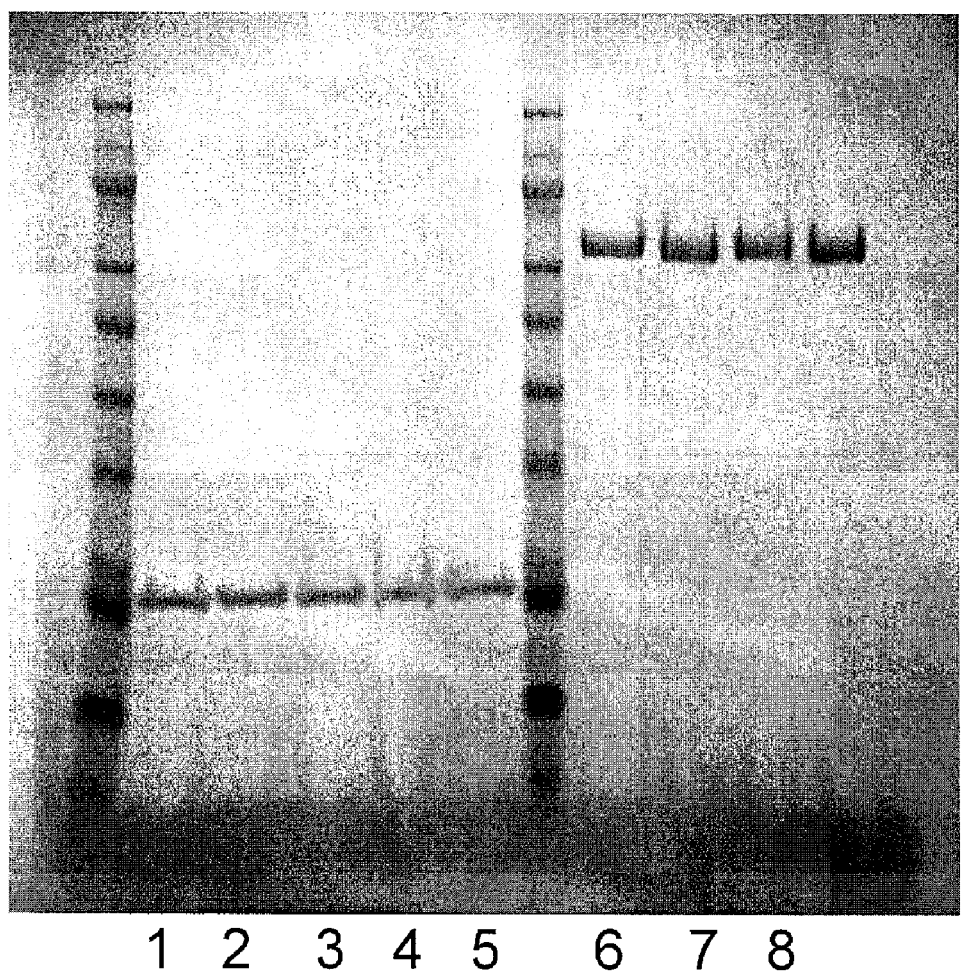
FIG. 5—IFN beta polypeptides before and after PEGylation of the present invention are shown.
Figure 10:
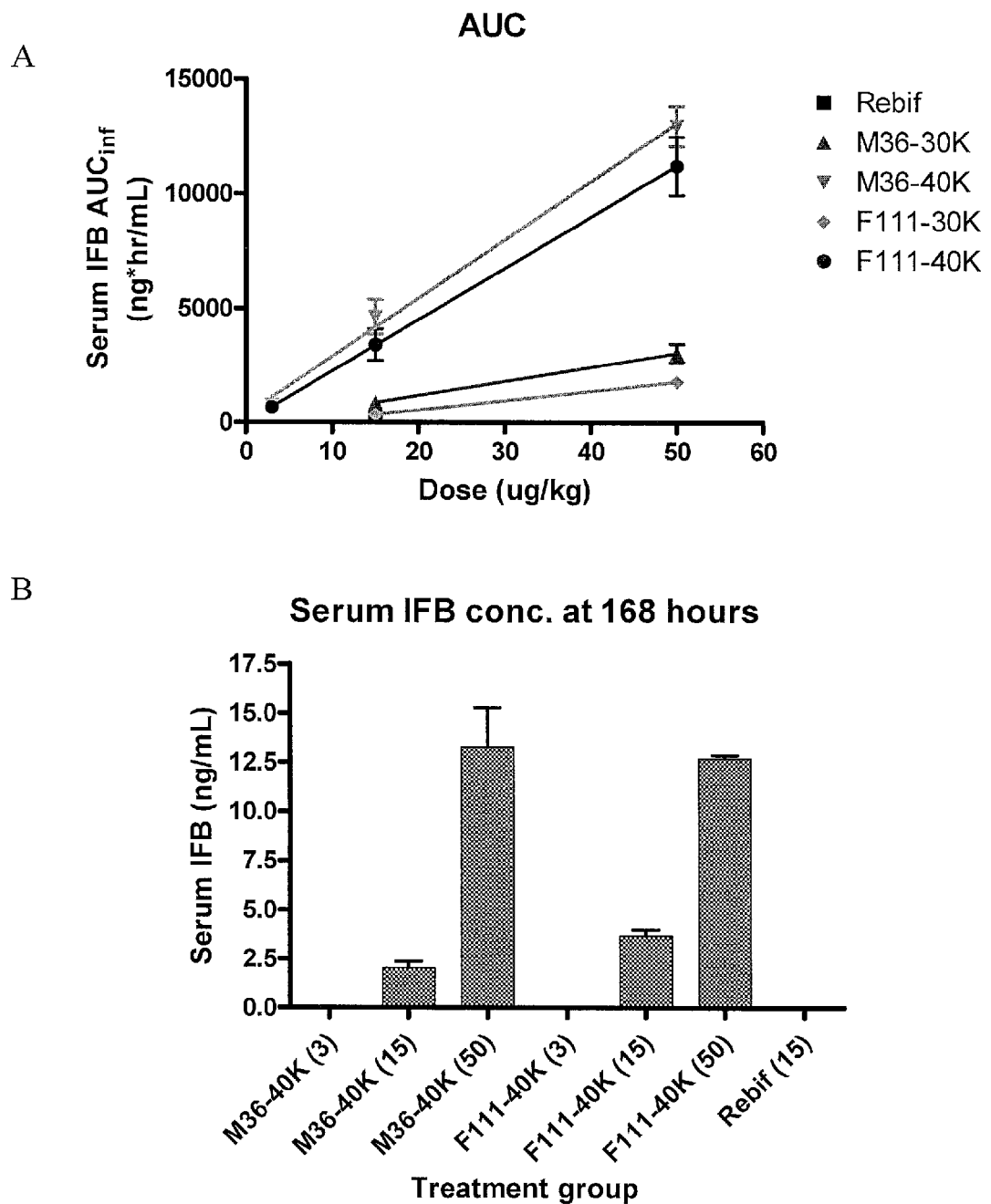
Figure 13:
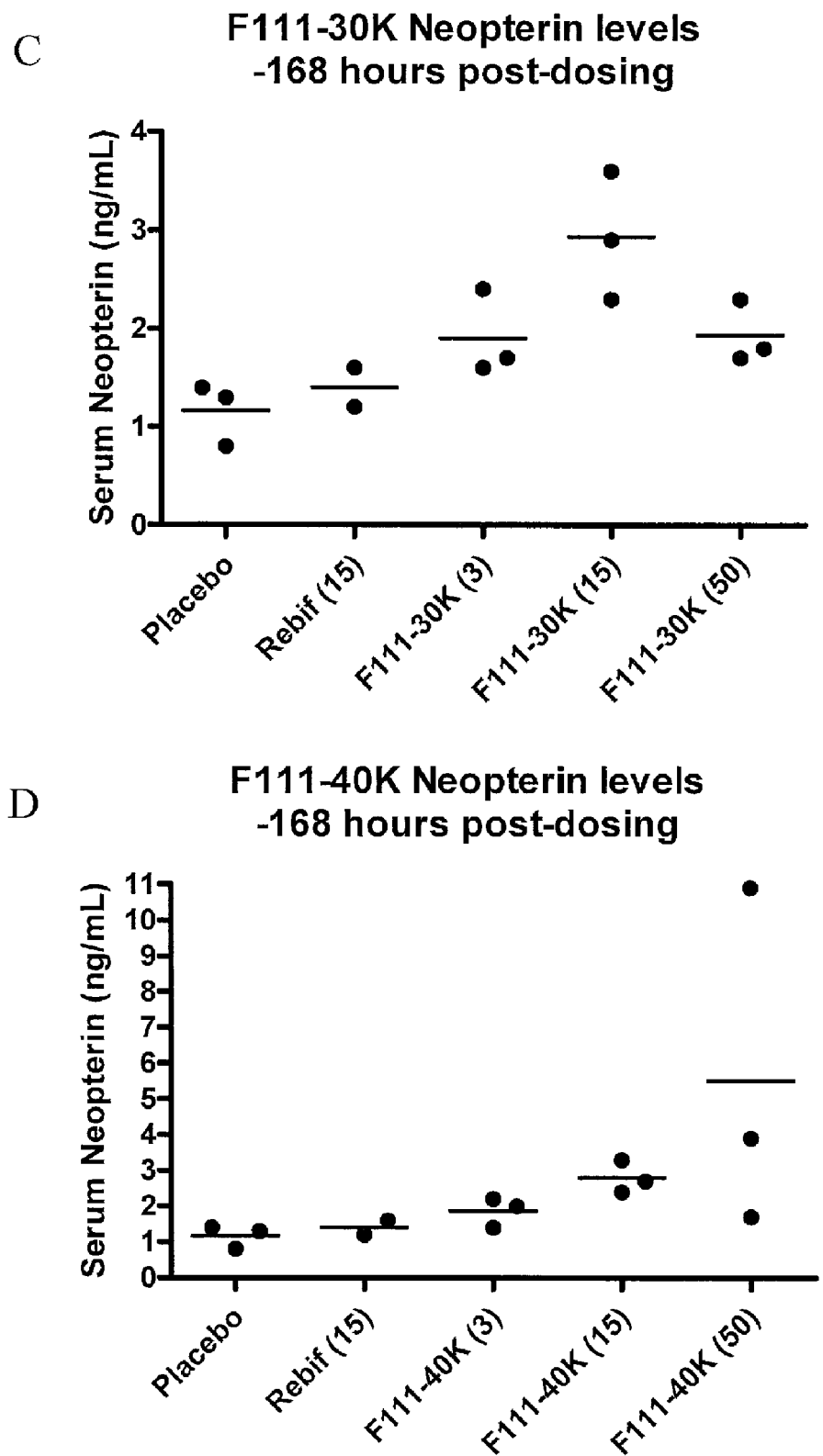
FIG. 13A—Serum neopterin level data from Example 27 is shown at 168 hours post-dosing with placebo, control, and three different dosage levels of M36-30K.
FIG. 13B—Serum neopterin level data from Example 27 is shown at 168 hours post-dosing with placebo, control, and three different dosage levels of M36-40K.
FIG. 13C—Serum neopterin level data from Example 27 is shown at 168 hours post-dosing with placebo, control, and three different dosage levels of F111-30K.
FIG. 13D—Serum neopterin level data from Example 27 is shown at 168 hours post-dosing with placebo, control, and three different dosage levels of F111-40K.
Figure 14:
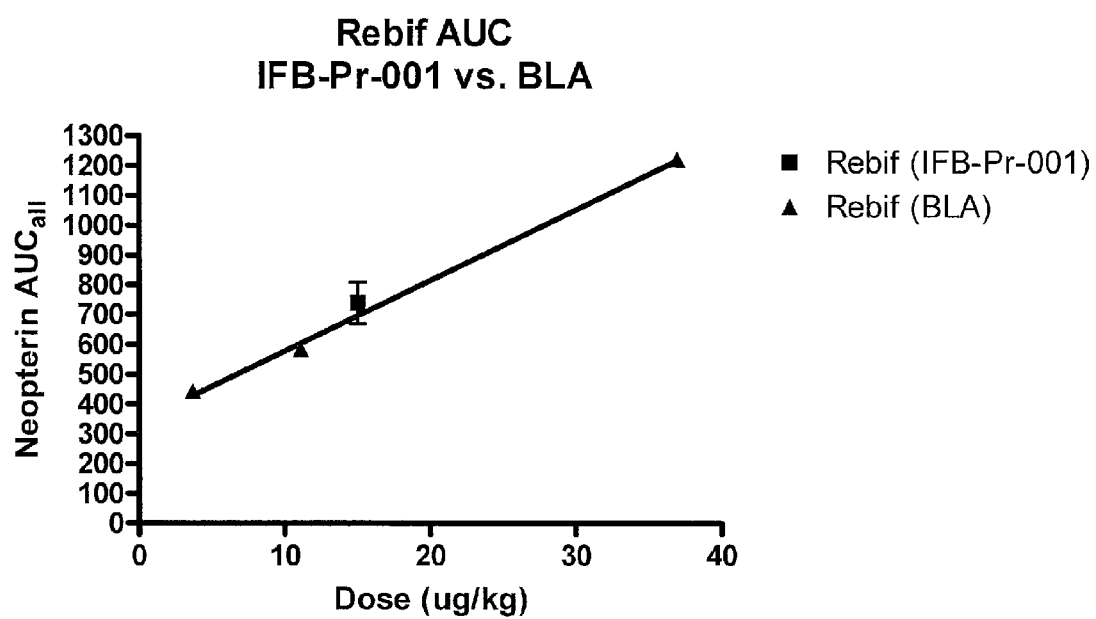
FIG. 14—A graph showing the Neopterin AUC/dose of REBe from the protocol disclosed in Example 27 and the BLA.
Figure 15:
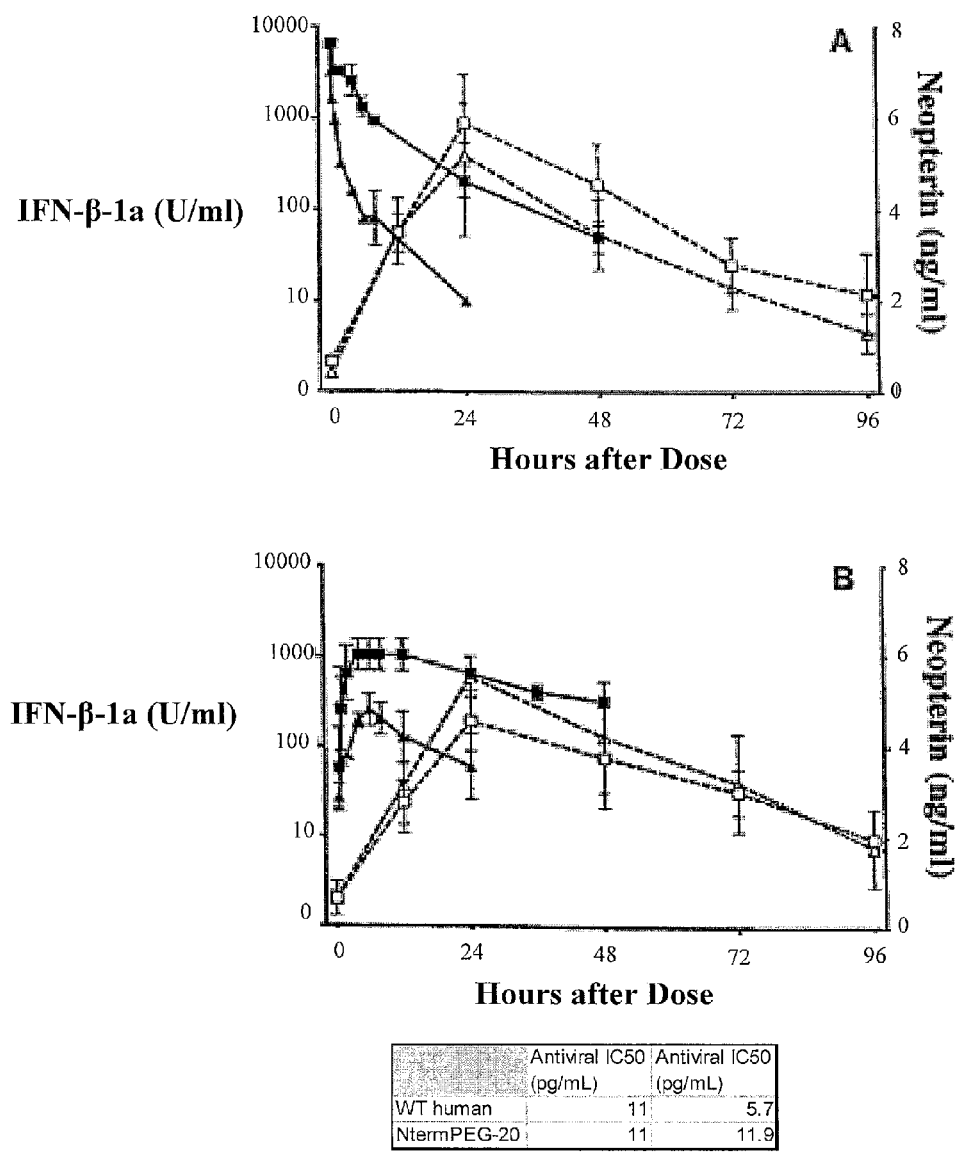
Figure 15:
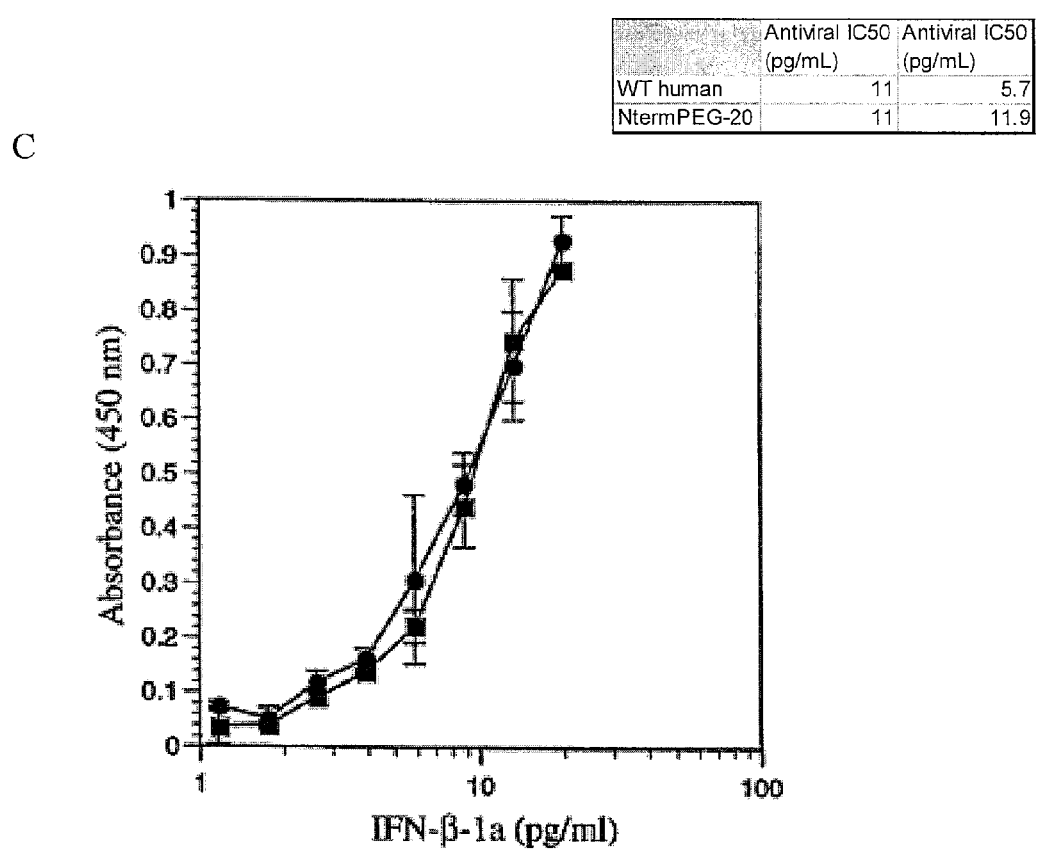
Figure 18:
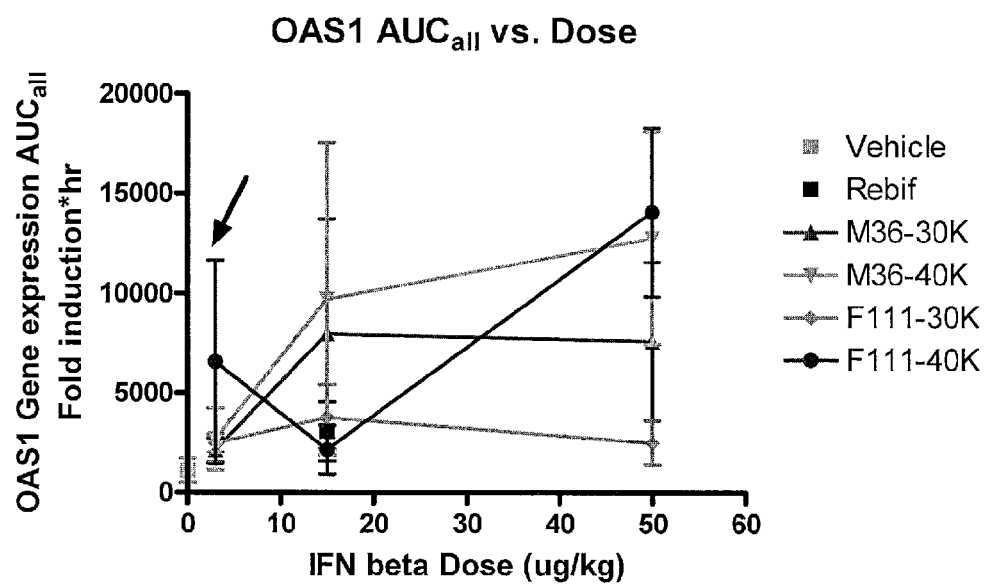
FIG. 18—A graph of data from Example 27 showing the area under the curve of the fold induction of OAS1 gene expression against dose level for a vehicle, a control, and four different IFN beta 1a variants of the present invention.
Figure 19:
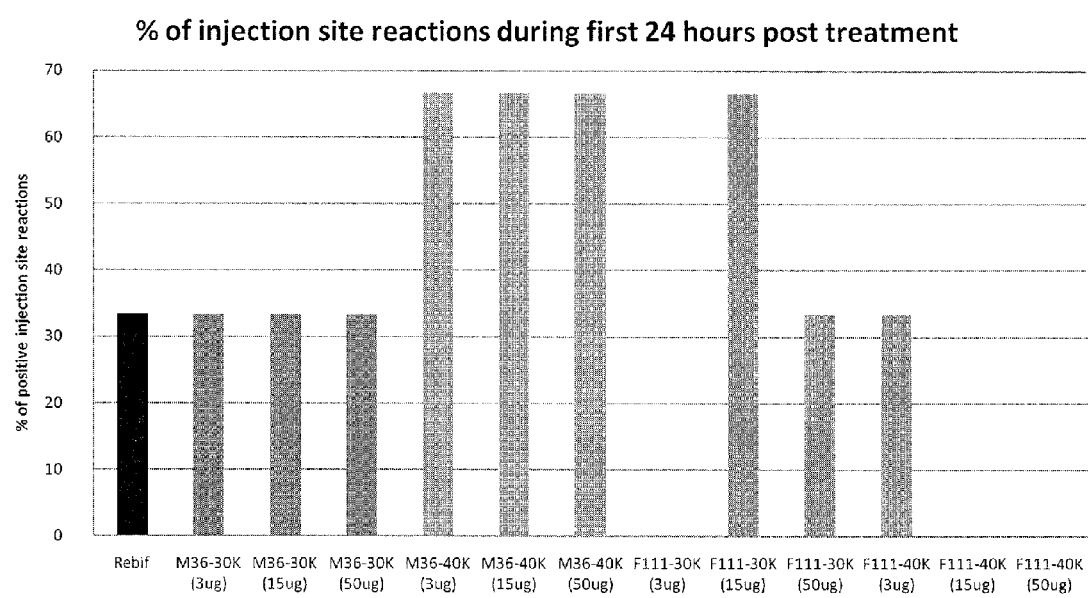
FIG. 19—A bar graph of the percentage of injection site reactions during the first twenty-four hours post dose administration.
Figure 22:
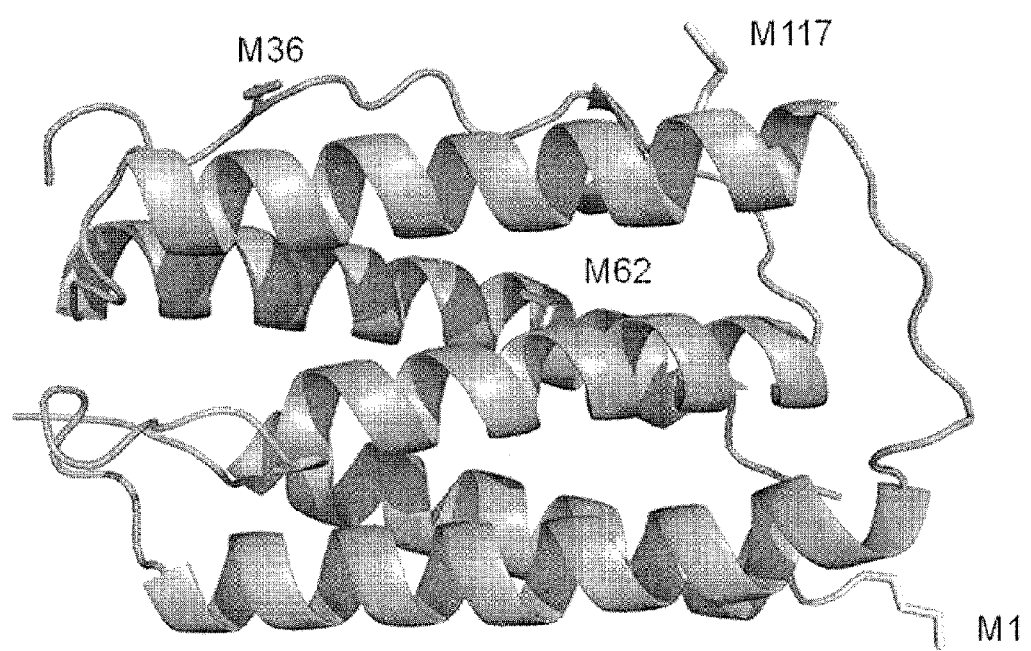
FIG. 22—A model of the crystal structure of IFN beta with potential sites for methionine oxidation is shown. M36 and 117 are susceptible for oxidation, M1 is a bit susceptible however when produced in *E. Coli*, the M1 should be cleaved (however may not be fully processed), and M62 is a site that is not susceptible for oxidation.
Figure 23:
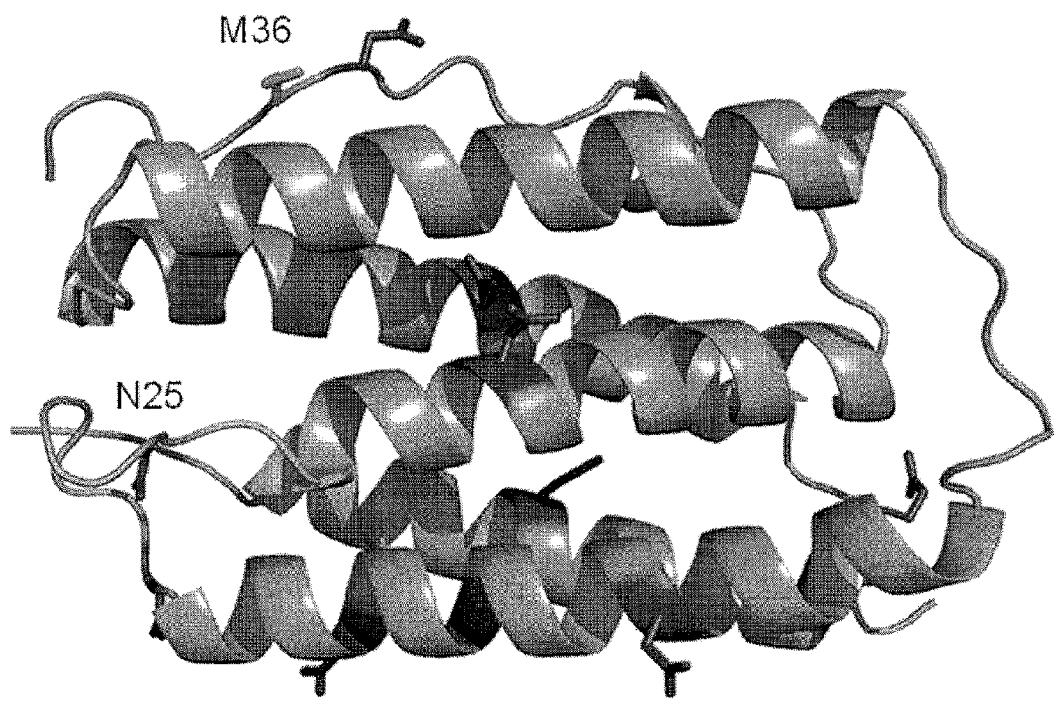
FIG. 23—A model of the crystal structure of IFN beta with potential sites for deamidation is shown. M36 and N25 are both potential sites—N25 is a known site for deamidation.
Figure 24:
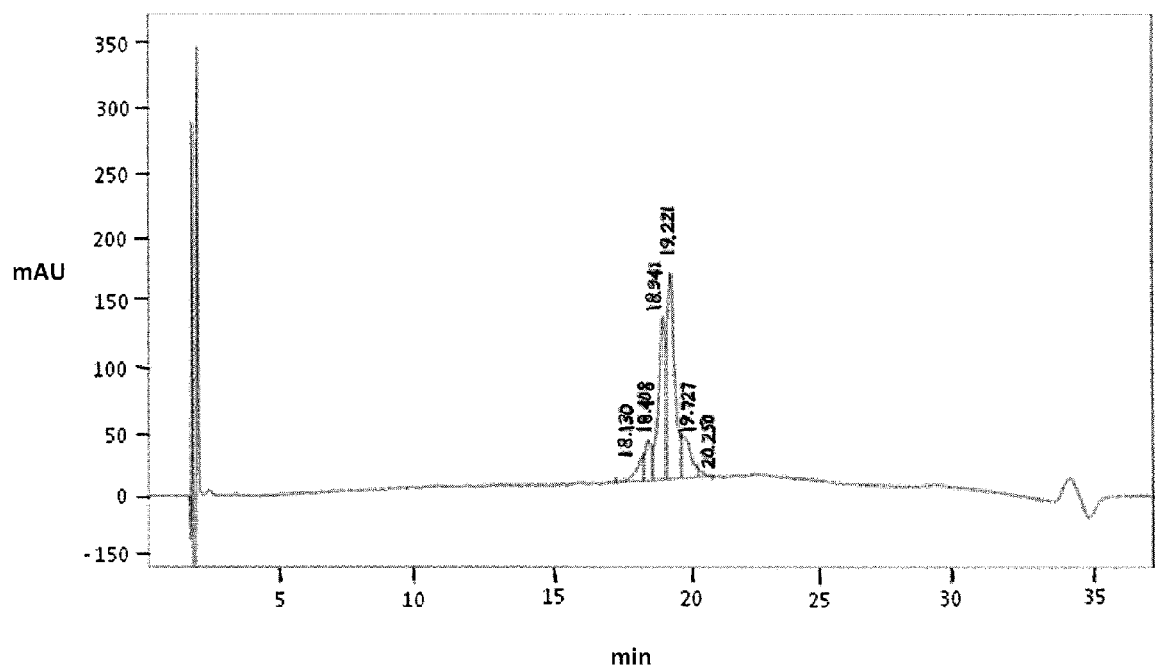
FIG. 24—Panel A, IFN M36pAF chromatogram analyzed using methods described in Example 28 and Panel B, close-up view of IFN M36pAF chromatogram analyzed using methods described in Example 28.
Figure 24:
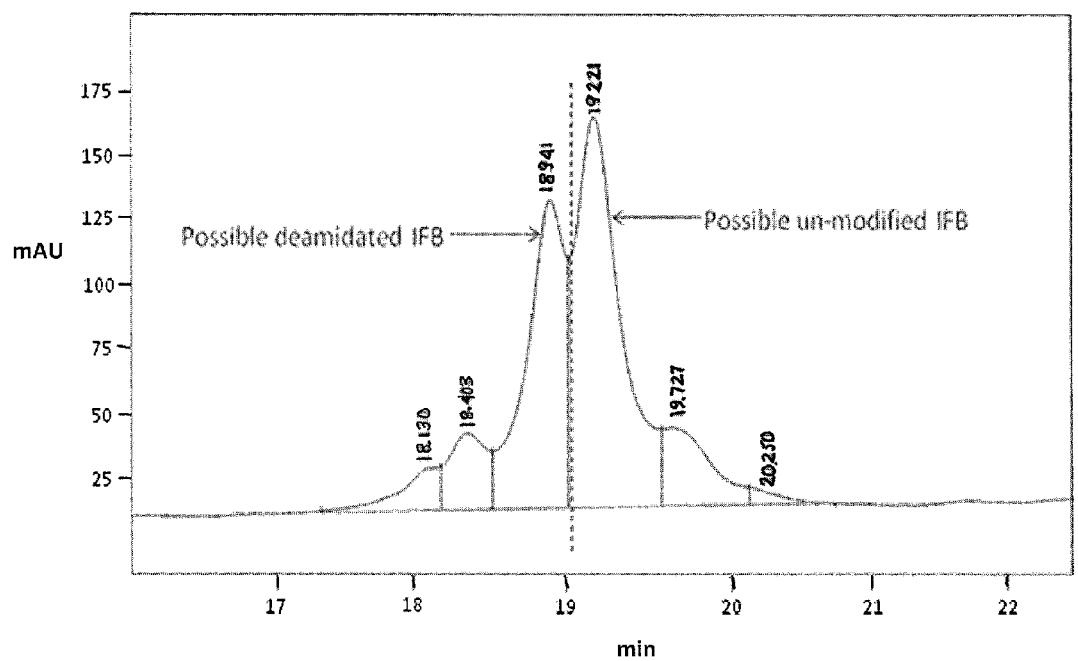
Figure 25:
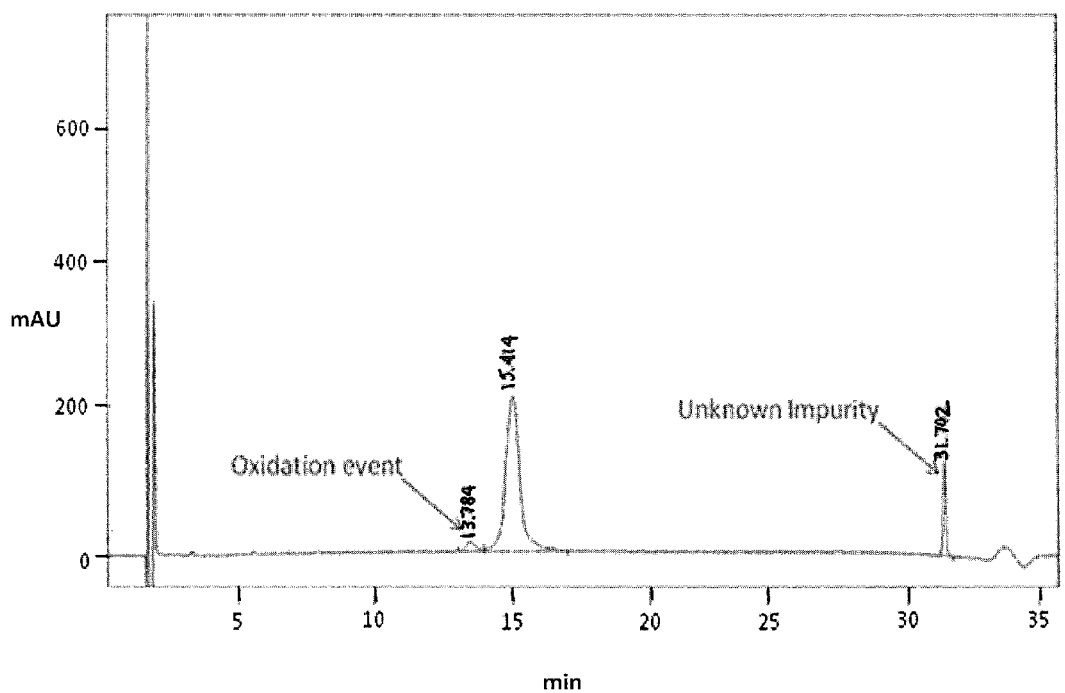
FIG. 25—Panel A, PEG40-M36pAF chromatogram analyzed using methods described in Example 28 Panel B PEG40-M36pAF chromatogram analyzed using methods described in Example 28.
Figure 25:
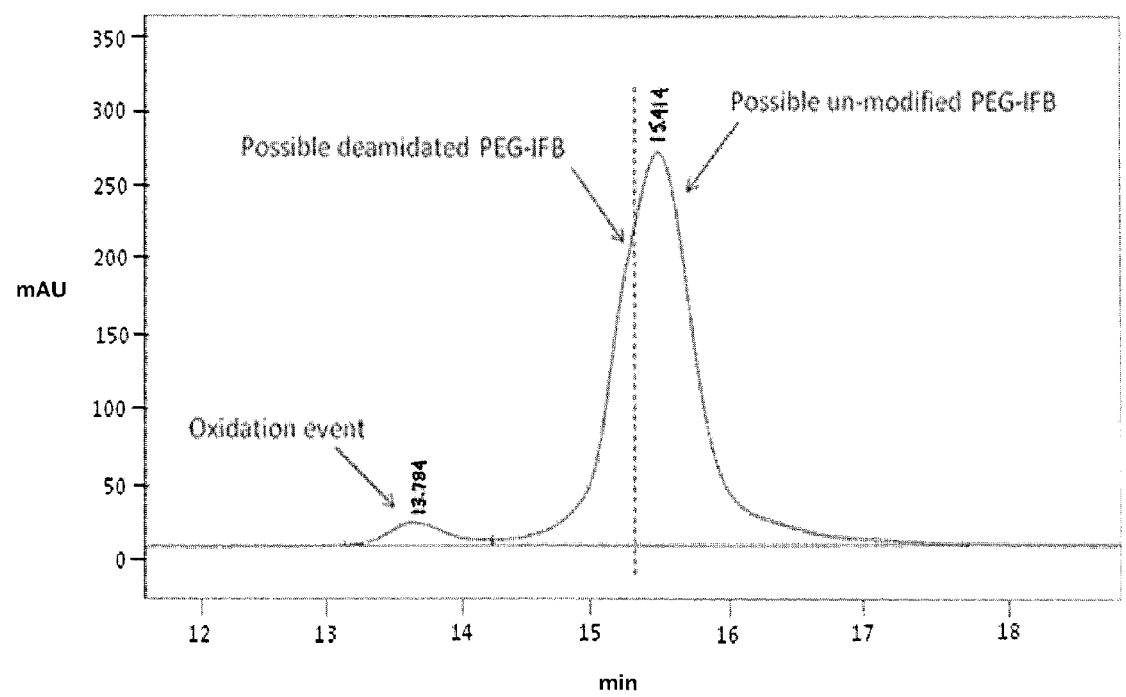
Figure 26:
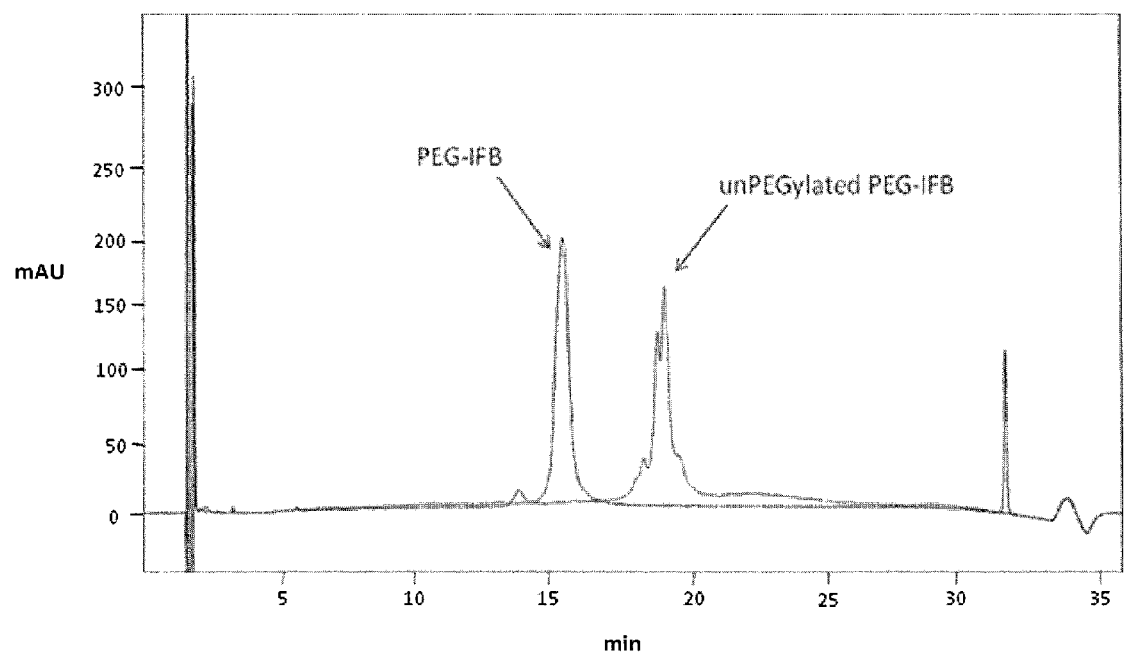
FIG. 26—Overlay chromatogram of IFN M36pAF and PEG40-M36pAF using methods described in Example 28.
Figure 27:
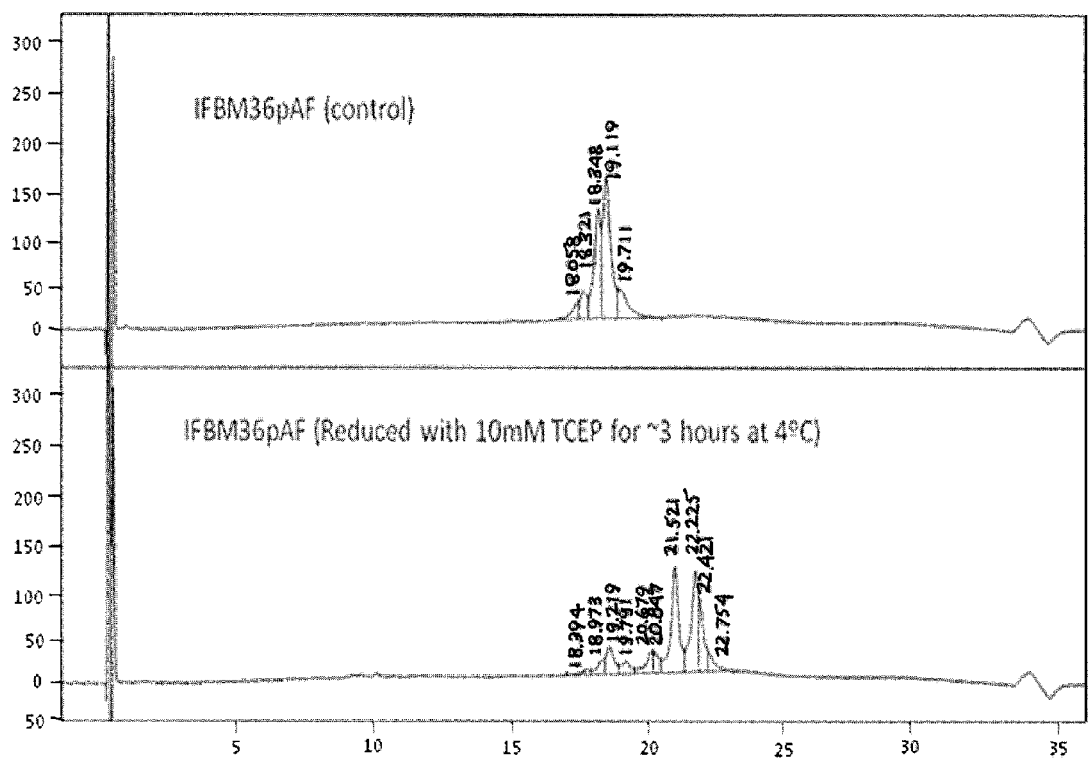
FIG. 27—Disulfide bond reduced IFN-M36pAF and analyzed using method described in Example 28.
Figure 28:
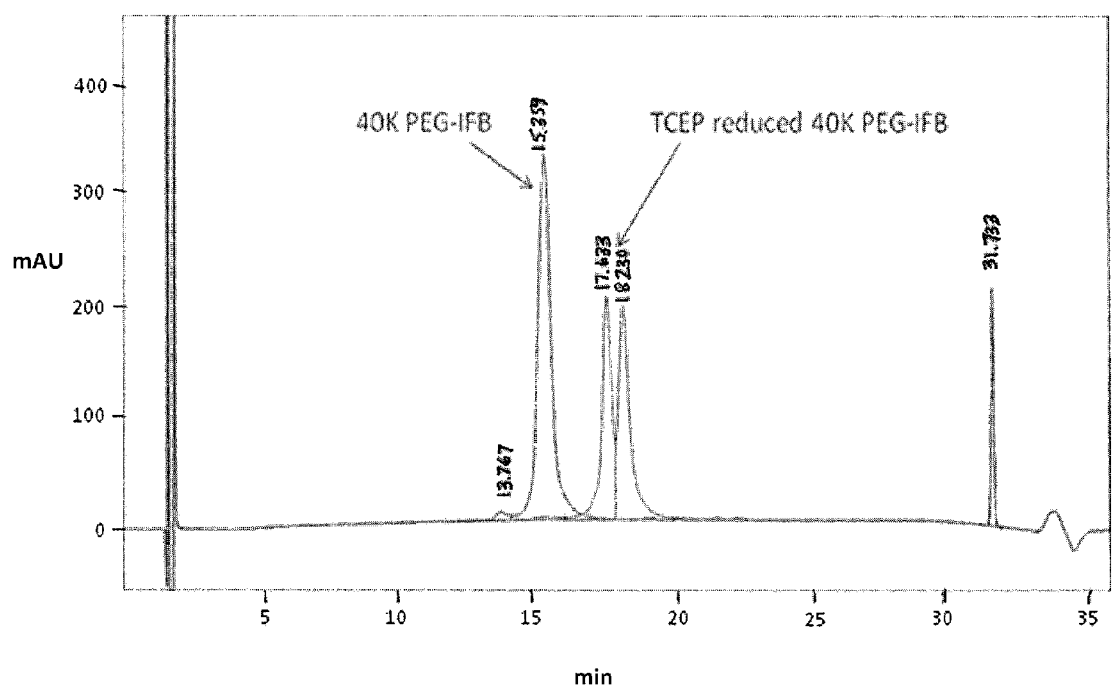
FIG. 28—Disulfide bond reduced PEG40-IFN36pAF and analyzed using method described in Example 28.

Plasmids for the expression IFN beta polypeptides were transformed into BL21DE3 *E. coli* cells. Para-acetyl-phenylalanine (pAF) was added to the cells, and protein expression was induced. SDS PAGE analysis of the expression of IFN beta polypeptides is shown on FIG. 3, and the IFN beta polypeptides are marked with an arrow. Lane 1—Original wild type IFN beta polypeptide (polynucleotide sequence obtained from CODA, Laguna Hills, Calif.); lane 2—L28pAF; lane 3—M36pAF; lane 4—S76pAF; lane 5—N80pAF; lane 6—E107pAF; lane 7—K108pAF; lane 8—F111pAP; lane 9—wild type IFN beta with optimized 5' end. For the pAF substituted IFN beta polypeptides, L28pAF, Plasmids for the expression IFN beta polypeptides were also transformed into W3110-B2 *E. coli* cells. Expression of the T7 polymerase was under control of an arabinose-inducible promoter. Para-acetyl-phenylalanine (pAF) was added to the cells, and protein expression was induced by the addition of arabinose (0.2% final). Cultures were incubated for 5 hours at 37° C. From a 1 liter flask culture, 100-200 mg of inclusion bodies was isolated. FIG. 4 shows SDS PAGE analysis of the total lysate (TL), supernatant (S), and pellet (P) from suppression in W3110-B2 *E. coli* cells; an arrow indicates the IFN beta polypeptides produced. Lanes 1 & 8—Markers; Lane 2—TL of wild-type IFN beta with the A-T rich 5' end modifications in the polynucleotide sequence; lane 3—S of wild-type IFN beta with the A-T rich 5' end modifications in the polynucleotide sequence; lane 4—P of wild-type IFN beta with the A-T rich 5' end modifications in the polynucleotide sequence; lane 5—TL of IFN beta with N80pAF substitution and with the A-T rich 5' end modifications in the polynucleotide sequence; lane 6—S of IFN beta with N80pAF substitution and with the A-T rich 5' end modifications in the polynucleotide sequence; lane 7—P of IFN beta with N80pAF substitution and with the A-T rich 5' end modifications in the polynucleotide sequence. None of the constructs encoded for the C17S substitution.

Additional Constructs

Expression constructs were generated with IFN beta polynucleotide sequence with an A-T rich 5' end, encoding the C17S mutation, and selector codons for a non-natural amino acid substitution. IFN beta polypeptides generated with these constructs were isolated and PEGylated.

Inclusion Body Prep Solubilization

The cell pastes were resuspended by mixing to a final 10% solid in 4° C. inclusion body (IB) Buffer I (50 mM Tris pH 8.0; 100 mM NaCl; 1 mM EDTA; 1% Triton X-100; 4° C.). The cells were lysed by passing resuspended material through a microfluidizer a total of two times. The samples were centrifuged (14,000 g; 15 minutes; 4° C.), and the supernatants were decanted. The inclusion body pellets were washed by resuspending in an additional volume of IB buffer I (50 mM Tris pH 8.0; 100 mM NaCl; 1 mM EDTA; 1% Triton X-100; 4° C.), and the resuspended materials were passed through the microfluidizer a total of two times. The samples were then centrifuged (14,000 g; 15 minutes; 4° C.), and the supernatants were decanted. The inclusion body pellets were each resuspended in one volume of buffer II (50 mM Tris pH 8.0; 100 mM NaCl; 1 mM EDTA; 4° C.). The samples were centrifuged (14,000 g; 15 minutes; 4° C.), and the supernatants were decanted. The inclusion body pellets were resuspended in ½ volume of buffer II (50 mM Tris pH 8.0; 100 in M NaCl; 1 in M EDTA; 4° C.). The inclusion bodies were then aliquoted into appropriate containers. The samples were centrifuged (14,000 g; 15 minutes; 4° C.), and the supernatants were decanted. The inclusion bodies were solubilized or stored at −80° C. until further use.

Inclusion Body Solubilization

Inclusion bodies were solubilized to a final concentration between 10-15 mg/mL in solubilization buffer (20 mM Tris, pH 8.0; 8M Guanidine; 10 mM 13-ME). The solubilized inclusion bodies were then incubated at room temperature under constant mixing for 1 hour or until fully solubilized. The samples were then centrifuged (10,000 g; 20 minutes; 4° C.) to remove any unsolubilized material. The protein concentration of each sample was then adjusted by dilution with additional solubilization buffer if the protein concentration was high.

Refolding

Refolding was performed by diluting the samples to a final protein concentration of 0.5 mg/mL in 20 mM Tris, pH 8.0; 60% Sucrose; 4° C. Refolding was allowed for 5 days at 4° C.

Purification

Refolded material was diluted 1:1 with Milli-Q $H_2O$. Material was filtered through a 0.22 mm PES filter and loaded over a Blue Sepharose FF column (GE Healthcare) equilibrated in 20 mM Tris, pH 8.0; 0.15M NaCl (buffer A). In up flow, the column was washed with 5 column volumes 30% buffer B (20 mM Tris, pH 8.0; 2M NaCl; 50% Ethylene Glycol). IFNβ polypeptides were eluted by washing the column with 10 column volumes of 100% buffer B.

PEGylation and Purification

The IFNβ pool was taken and diluted 10× with Milli-Q water. The pH of each sample was adjusted to 4.0 with 50% glacial acetic acid. The samples were concentrated down to ~1.0 mg/mL. 1:12 molar excess activated PEG (hydroxylamine PEG) was added to each sample. The samples were then incubated at 27° C. for 48-72 hours. Samples were taken and diluted 8-10 fold with water (<8 m/S) and loaded over a SP HP column (GE Healthcare) equilibrated in Buffer A (50 mM NaAc, pH 6.0; 50 mM NaCl; 0.05% Zwittergent 3-14). The IFNβ polypeptides were eluted with 5 column volumes of buffer B (50 mM NaAc, pH 6.0; 500 mM NaCl; 0.05% Zwittergent 3-14). Fractions of IFNβ were pooled and run over a Superdex 200 sizing column equilibrated in IFNβ storage buffer (20 mM NaAc, pH 5.0; 150 mM NaCl; 0.05% Zwittergent 3-14). The PEGylated material was collected and stored at 4° C.

FIG. 5 shows IFN beta polypeptides before and after PEGylation: lane 1: IFN beta with C17S substitution; lane 2: IFN beta with C17S and L28pAF substitutions; lane 3: IFN beta with C17S and M36pAF substitutions; lane 4: IFN beta with C17S and S76pAF substitutions; lane 5: IFN beta with C17S and F111pAF substitutions; lane 6: IFN beta with C17S and L28pAF-30K PEG; lane 7: IFN beta with C17S and M36pAF-30K PEG; lane 8: IFN beta with C17S and S76pAF-30K PEG; lane 9: IFN beta with C17S and F111pAF-30K PEG. The PEGylated molecules were conjugated at the position shown for pAF. The polynucleotide sequence for all of these IFN beta polypeptides had the A-T rich 5' end modifications mentioned previously.

Biacore Studies (Receptor Binding Affinity)

The sequence for the IFNAR2 extracellular domain (consisting of 206 amino acids ending with sequence LLPPGQ) was amplified from clone MHS1011-61064 (OpenBiosystems, Huntsville, Ala.). This insert was cloned into the pET20 expression vector (Novagen) downstream of the T7 promoter. Protein expression was induced with 0.4 mM IPTG in BL21 (DE3) cells (Novagen).

Since the expressed protein was insoluble, the inclusion bodies were purified from lysed cells and solubilized in 6M GndCl. A 5 ml aliquot (50 mg amount) was reduced with 10 mM DTT for 45 minutes at 37° C. Then the mixture was injected into 200 ml of refolding buffer which consisted of 50 mM Tris pH 8, 20 mM NaCl, 0.5 M Arginine, 10% glycerol at 4° C. and incubated overnight with gentle stirring.

The refolding reaction was then concentrated to 25 ml using an Amicon stirring cell, and dialyzed overnight against 20 mM Tris, pH 8, 20 mM NaCl, 10% glycerol. Monomeric refolded IFNAR ECD was purified on HP Q Sepharose using the AKTA FPLC system (Amersham). Purified IFNAR2ECD was immobilized on CM5 Biacore chip using a lysine-specific coupling procedure recommended by the manufacturer. About 200 RUs of functional protein were immobilized. Various concentrations of IFN beta variants in HBS-EP buffer (Biacore) were injected at a flow rate of 50 mel/minute over the flowcell containing immobilized IFNAR2, and a control flowcell containing immobilized bovine serum albumin. Sensograms generated were fit to the 1:1 interaction model to calculate $k_{on}$, $k_{off}$ and $k_d$ values using BiaEvaluation software (BIACORE®). Interferon alpha products, PEGASYS® and ROFERON®, were included as control samples. Table 4 shows the average $K_d$ obtained with the IFN beta polypeptides.

TABLE 4

| IFNβ molecule | Kd |
|---|---|
| (C17S)-IFNβ | 0.8 nM |
| (C17S) L28pAF-30K PEG | >30 nM |
| (C17S) M36pAF-30K PEG | 5.0 nM |
| (C17S) S76pAF-30K PEG | 11 nM |
| (C17S) F111pAF-30K PEG | 5.8 nM |
| Roferon ® | 5 nM |
| Pegasys ® | 240 nM |

VSV Anti-Viral Assay

Antiviral activity of IFN beta polypeptides may be measured by a variety of assays. The antiviral activity of IFN beta polypeptides was determined using the Vesicular Stomatitis Virus (VSV). The culture media for this assay was DMEM, 10% FBS, 1% Penicillin/Streptomycin, 5 ml HEPES. Additional reagents included RPMI without FBS and Phenol Red. The concentration of MTT stock used was 5 mg/mL in PBS. This stock solution was stored for only two weeks at 4° C.

Human WISH cells were seeded at 30,000 cells/well in 50 µL of culture media. The following day, 2× serial dilutions were performed of the IFN beta polypeptides in culture media. IFN beta with a C17S natural amino acid substitution was used as a control in these experiments. In triplicate, 100 µL of the diluted IFN beta polypeptides was added to the WISH cells for a final well volume of 150 µL. The cells and IFN beta polypeptides were incubated for 6 hours at 37° C. in a $CO_2$ incubator. After this six hour incubation, 10,000 PFU of VSV was added per well, in a volume of 50 µL of media; 20 µL of VSV was diluted in 5 ml of media per 96 well/plate. The media was removed by aspiration forty-five hours post-infection. The plates were gently tapped on paper towels to remove residual media.

50 µL of 1 mg/mL MTT (3-(4,5-dimethylthiazol-2-yl) 2,5-dipbenzyltetrazolium bromide) prepared in RPMI without Phenol Red and FBS was added from a 5 mg/mL MTT stock solution. 1 mg/mL MTT was usually prepared fresh for every assay. Next, the plates were incubated for three hours at 37° C. in the $CO_2$ incubator. The MTT was carefully removed by aspiration. 50 µL of isopropanol was added per well. The plates were placed on a plate-shaker for 30 to 40 seconds to complete the formation of MTT. The plates were read at 560 nm with 690 nm as a reference wavelength. The data was plotted and the $IC_{50}$ calculated using the Sigma-Plot program.

Table 5 summarizes the anti-viral activity of IFN beta polypeptides. The second column lists the averaged $IC_{50}$ values for each compound. Two molecules, (C17S) M36pAF-30K PEG and (C17S) F111pAF-30K PEG, had enhanced anti-viral activity over the wild type molecule (C17S)—IFN beta.

TABLE 5

| IFNβ molecule | $IC_{50}$ (ng/ml) |
|---|---|
| (C17S) M36pAF-30K PEG | 0.028 |
| (C17S) F111pAF-30K PEG | 0.055 |
| (C17S)-IFNβ | 0.19 |
| (C17S) S76pAF-30K PEG | 0.26 |
| (C17S) M36pAF | 0.27 |
| (C17S) F111pAF | 0.23 |
| (C17S) S76pAF | 0.50 |
| (C17S) L28pAF-30K PEG | 0.74 |
| (C17S) L28pAF | 0.88 |

Example 3

This example details introduction of a carbonyl-containing amino acid and subsequent reaction with an aminooxy-containing PEG.

This Example demonstrates a method for the generation of a IFN beta polypeptide that incorporates a ketone-containing non-naturally encoded amino acid that is subsequently reacted with an aminooxy-containing PEG of approximately 5,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4) is separately substituted with a non-naturally encoded amino acid having the following structure:

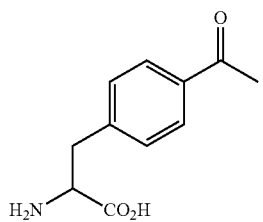

The sequences utilized for site-specific incorporation of p-acetyl-phenylalanine into IFN beta are SEQ ID NO: 1 (IFN beta), and SEQ ID NO: 6 or 7 (muttRNA, *M. jannaschii* $mtRNA_{CUA}^{Tyr}$), and SEQ ID NOs: 24, 5, 19, 20, 21 (TyrRS LW1, 5, or 6) described in Example 2 above.

Once modified, the IFN beta polypeptide variant comprising the carbonyl-containing amino acid is reacted with an aminooxy-containing PEG derivative of the form:

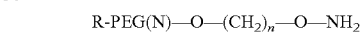

where R is methyl, n is 3 and N is approximately 5,000 MW. The purified IFN beta containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. *J. Am. Chem. Soc.* 1959, 81, pp 475). The PEG-IFN beta is then diluted into appropriate buffer for immediate purification and analysis.

Example 4

Conjugation with a PEG consisting of a hydroxylamine group linked to the PEG via an amide linkage.

A PEG reagent having the following structure is coupled to a ketone-containing non-naturally encoded amino acid using the procedure described in Example 3:

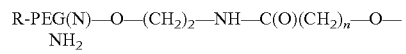

where R=methyl, n=4 and N is approximately 20,000 MW. The reaction, purification, and analysis conditions are as described in Example 3.

Example 5

This example details the introduction of two distinct non-naturally encoded amino acids into IFN beta polypeptides.

This example demonstrates a method for the generation of a IFN beta polypeptide that incorporates non-naturally encoded amino acid comprising a ketone functionality at two positions among the following residues: before position I (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4). The IFN beta polypeptide is prepared as described in Examples 1 and 2, except that the selector codon is introduced at two distinct sites within the nucleic acid.

Example 6

This example details conjugation of IFN beta polypeptide to a hydrazide-containing PEG and subsequent in situ reduction.

A IFN beta polypeptide incorporating a carbonyl-containing amino acid is prepared according to the procedure described in Examples 2 and 3. Once modified, a hydrazide-containing PEG having the following structure is conjugated to the IFN beta polypeptide:

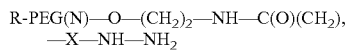

where R=methyl, n=2 and N=10,000 MW and X is a carbonyl (C=O) group. The purified IFN beta containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1M NaCNBH$_3$ (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 7

This example details introduction of an alkyne-containing amino acid into a IFN beta polypeptide and derivatization with mPEG-azide.

The following residues, before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4), are each substituted with the following non-naturally encoded amino acid:

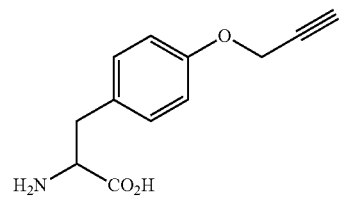

The sequences utilized for site-specific incorporation of p-propargyl-tyrosine into IFN beta are SEQ ID NO: 1 (IFN beta), SEQ ID NO: 7 (muttRNA, *M. jannaschii* mtRNA$_{CUA}^{Tyr}$), and 12, 13 or 14 described in Example 2 above. The IFN beta polypeptide containing the propargyl tyrosine is expressed in *E. coli* and purified using the conditions described in Example 3.

The purified IFN beta containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of CuSO$_4$ and Cu wire are then added to the reaction mixture. After the mixture is incubated (including but not limited to, about 4 hours at room temperature or 37° C., or overnight at 4° C.), H$_2$O is added and the mixture is filtered through a dialysis membrane. The sample can be analyzed for the addition, including but not limited to, by similar procedures described in Example 3.

In this Example, the PEG will have the following structure:

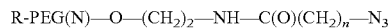

where R is methyl, n is 4 and N is 10,000 MW.

Example 8

This example details substitution of a large, hydrophobic amino acid in a IFN beta polypeptide with propargyl tyrosine.

A Phe, Trp or Tyr residue present within one the following regions of IFN beta: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4) is substituted with the following non-naturally encoded amino acid as described in Example 7:

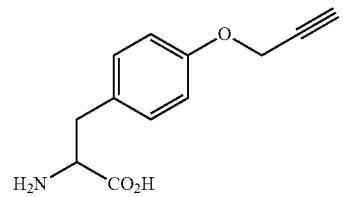

Once modified, a PEG is attached to the IFN beta polypeptide variant comprising the alkyne-containing amino acid. The PEG will have the following structure:
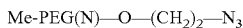

$$Me\text{-}PEG(N)—O—(CH_2)_2—N_3$$

and coupling procedures would follow those in Example 7. This will generate a IFN beta polypeptide variant comprising a non-naturally encoded amino acid that is approximately isosteric with one of the naturally-occurring, large hydrophobic amino acids and which is modified with a PEG derivative at a distinct site within the polypeptide.

Example 9

This example details generation of a IFN beta polypeptide homodimer, heterodimer, homomultimer, or heteromultimer separated by one or more PEG linkers.

The alkyne-containing IFN beta polypeptide variant produced in Example 7 is reacted with a bifunctional PEG derivative of the form:

$$N_3—(CH_2)_n—C(O)—NH—(CH_2)_2—O\text{-}PEG(N)—O—(CH_2)_2—NH—C(O)—(CH_2)_n—N_3$$

where n is 4 and the PEG has an average MW of approximately 5,000, to generate the corresponding IFN beta polypeptide homodimer where the two IFN beta molecules are physically separated by PEG. In an analogous manner a IFN beta polypeptide may be coupled to one or more other polypeptides to form heterodimers, homomultimers, or heteromultimers. Coupling, purification, and analyses will be performed as in Examples 7 and 3.

Example 10

This example details coupling of a saccharide moiety to a IFN beta polypeptide.

One residue of the following is substituted with the non-naturally encoded amino acid below: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167 (i.e., at the carboxyl terminus of the protein), and any combination thereof (SEQ ID NO: 1 or the corresponding amino acids in SEQ ID NOs: 3, 4) as described in Example 3.

Once modified, the IFN beta polypeptide variant comprising the carbonyl-containing amino acid is reacted with a β-linked aminooxy analogue of N-acetylglucosamine (GlcNAc). The IFN beta polypeptide variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated IFN beta polypeptide (5 mg/mL) with UDP-galactose (16 mM) and β-1,4-galacytosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 11

This example details generation of a PEGylated IFN beta polypeptide antagonist.

A residue, including but not limited to, those involved in IFN receptor binding is substituted with the following non-naturally encoded amino acid as described in Example 3.

Once modified, the IFN beta polypeptide variant comprising the carbonyl-containing amino acid will be reacted with an aminooxy-containing PEG derivative of the form:

$$R\text{-}PEG(N)—O—(CH_2)_n—O—NH_2$$

where R is methyl, n is 4 and N is 20,000 MW to generate a IFN beta polypeptide antagonist comprising a non-naturally encoded amino acid that is modified with a PEG derivative at a single site within the polypeptide. Coupling, purification, and analyses are performed as in Example 3.

Example 12

Generation of a IFN beta polypeptide homodimer, heterodimer, homomultimer, or heteromultimer in which the IFN beta Molecules are Linked Directly A IFN beta polypeptide variant comprising the alkyne-containing amino acid can be directly coupled to another IFN beta polypeptide variant comprising the azido-containing amino acid. In an analogous manner a IFN beta polypeptide may be coupled to one or more other polypeptides to form heterodimers, homomultimers, or heteromultimers. Coupling, purification, and analyses are performed as in Examples 3, 6, and 7.

Example 13

A

B

The polyalkylene glycol (P—OH) is reacted with the alkyl halide (A) to form the ether (B). In these compounds, n is an integer from one to nine and R' can be a straight- or branched-chain, saturated or unsaturated Cl, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 14

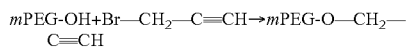

mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford propargyl-O-PEG.

Example 15

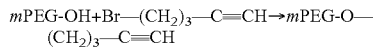

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 16

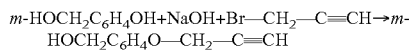 (1)

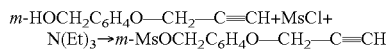 (2)

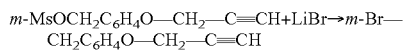 (3)

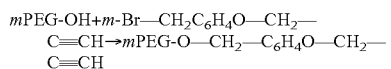 (4)

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over $MgSO_4$ and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in $CH_2Cl_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a white precipitate, which was collected to yield the PEG derivative.

Example 17

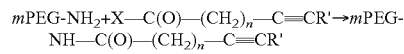

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 18

 (1)

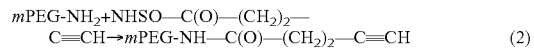 (2)

4-pentynoic acid (2.943 g, 3.0 mmol) was dissolved in $CH_2Cl_2$ (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-$NH_2$ with a molecular weight of 5,000 Da (mPEG-$NH_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added CH$_2$Cl$_2$ (50 mL) and the organic layer was separated, dried over anhydrous Na$_2$SO$_4$, and the volume was reduced to approximately 2 mL. This CH$_2$Cl$_2$ solution was added to ether (150 mL) drop-wise. The resulting precipitate was collected and dried in vacuo.

Example 19

This Example represents the preparation of the methane sulfonyl ester of poly(ethylene glycol), which can also be referred to as the methanesulfonate or mesylate of poly(ethylene glycol). The corresponding tosylate and the halides can be prepared by similar procedures.

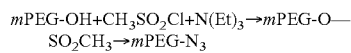

The mPEG-OH (MW=3,400, 25 g, 10 mmol) in 150 mL of toluene was azeotropically distilled for 2 hours under nitrogen and the solution was cooled to room temperature. 40 mL of dry CH$_2$Cl$_2$ and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with CH$_2$Cl$_2$ (50 mL). The organic fraction was washed with NaCl solution and dried over anhydrous MgSO$_4$. The volume was reduced to 20 ml and the product was precipitated by addition to 150 ml of cold dry ether.

Example 20

 (1)

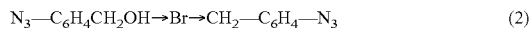 (2)

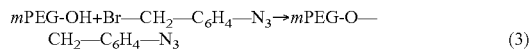 (3)

4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in CH$_2$Cl$_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na$_2$SO$_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of KI. The resulting mixture was heated to reflux for 12 hours. Water (1.0 mL) was added to the mixture and the solvent was removed under vacuum. To the residue was added CH$_2$Cl$_2$ (25 mL) and the organic layer was separated, dried over anhydrous Na$_2$SO$_4$, and the volume was reduced to approximately 2 mL. Dropwise addition to an ether solution (150 mL) resulted in a precipitate, which was collected to yield mPEG-O—CH$_2$—C$_6$H$_4$—N$_3$.

Example 21

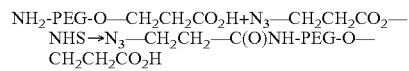

NH$_2$—PEG-O—CH$_2$CH$_2$CO$_2$H (MW 3,400 Da, 2.0 g) was dissolved in a saturated aqueous solution of NaHCO$_3$ (10 mL) and the solution was cooled to 0° C. 3-azido-1-N-hydroxysuccinimido propionate (5 equiv.) was added with vigorous stirring. After 3 hours, 20 mL of H$_2$O was added and the mixture was stirred for an additional 45 minutes at room temperature. The pH was adjusted to 3 with 0.5 NH$_2$SO$_4$ and NaCl was added to a concentration of approximately 15 wt %. The reaction mixture was extracted with CH$_2$Cl$_2$ (100 mL×3), dried over Na$_2$SO$_4$ and concentrated. After precipitation with cold diethyl ether, the product was collected by filtration and dried under vacuum to yield the omega-carboxy-azide PEG derivative.

Example 22

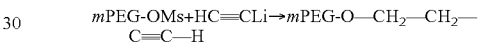

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of H$_2$O is then added and the mixture was stirred for an additional 45 minutes at room temperature. The pH was adjusted to 3 with 0.5 NH$_2$SO$_4$ and NaCl was added to a concentration of approximately 15 wt %. The reaction mixture was extracted with CH$_2$Cl$_2$ (100 mL×3), dried over Na$_2$SO$_4$ and concentrated. After precipitation with cold diethyl ether, the product was collected by filtration and dried under vacuum to yield the 1-(but-3-ynyloxy)-methoxypolyethylene glycol (mPEG).

Example 23

Azide- and acetylene-containing amino acids can be incorporated site-selectively into proteins using the methods described in L. Wang, et al., (2001), *Science* 292:498-500, J. W. Chin et al., *Science* 301:964-7 (2003)), J. W. Chin et al., (2002), *Journal of the American Chemical Society* 124:9026-9027; J. W. Chin, & P. G. Schultz, (2002), *Chem Bio Chem* 3(11):1135-1137; J. W. Chin, et al., (2002), *PNAS United States of America* 99:11020-11024: and, L. Wang, & P. G. Schultz, (2002), *Chem. Comm.,* 1:1-11. Once the amino acids were incorporated, the cycloaddition reaction is carried out with 0.01 mM protein in phosphate buffer (PB), pH 8, in the presence of 2 mM PEG derivative, 1 mM CuSO$_4$, and ~1 mg Cu-wire for 4 hours at 37° C.

Example 24

This example describes the synthesis of p-Acetyl-D,L-phenylalanine (pAF) and m-PEG-hydroxylamine derivatives.

The racemic pAF is synthesized using the previously described procedure in Zhang, Z., Smith, B. A. C., Wang, L., Brock, A., Cho, C. & Schultz, P. G., Biochemistry, (2003) 42, 6735-6746.

To synthesize the m-PEG-hydroxylamine derivative, the following procedures are completed. To a solution of (N-t-Boc-aminooxy)acetic acid (0.382 g, 2.0 mmol) and 1,3-Diisopropylcarbodiimide (0.16 mL, 1.0 mmol) in dichloromethane (DCM, 70 mL), which is stifled at room temperature (RT) for 1 hour, methoxy-polyethylene glycol amine (m-PEG-NH$_2$, 7.5 g, 0.25 mmol, Mt. 30 K, from Bio-Vectra) and Diisopropylethylamine (0.1 mL, 0.5 mmol) is added. The reaction is stirred at RT for 48 hours, and then is concentrated to about 100 mL. The mixture is added dropwise to cold ether (800 mL). The t-Boc-protected product precipitated out and is collected by filtering, washed by ether 3×100 mL. It is further purified by re-dissolving in DCM (100 mL) and precipitating in ether (800 mL) twice. The product is dried in vacuum yielding 7.2 g (96%), confirmed by NMR and Nihydrin test.

The deBoc of the protected product (7.0 g) obtained above is carried out in 50% TFA/DCM (40 mL) at 0° C. for 1 hour and then at RT for 1.5 hour. After removing most of TFA in vacuum, the TFA salt of the hydroxylamine derivative is converted to the HCl salt by adding 4N HCl in dioxane (1 mL) to the residue. The precipitate is dissolved in DCM (50 mL) and re-precipitated in ether (800 mL). The final product (6.8 g, 97%) is collected by filtering, washed with ether 3×100 mL, dried in vacuum, stored under nitrogen. Other PEG (5K, 20K) hydroxylamine derivatives are synthesized using the same procedure.

Example 25

In Vivo Studies of PEGylated IFN Beta

PEG-IFN beta, unmodified IFN beta and buffer solution are administered to mice or rats. The results will show superior activity and prolonged half life of the PEGylated IFN beta of the present invention compared to unmodified IFN beta. Similarly, modified IFN beta, unmodified IFN beta, and buffer solution are administered to mice or rats.
Pharmacokinetic Analysis WO 2005/091944 describes pharmacokinetic studies that can be performed with the IFN beta compounds of the present invention. A IFN beta polypeptide of the invention is administered by intravenous or subcutaneous routes to mice. The animals are bled prior to and at time points after dosing. Plasma is collected from each sample and analyzed by radioimmunoassay. Elimination half-life can be calculated and compared between IFN beta polypeptides comprising a non-naturally encoded amino acid and wild-type IFN beta or various forms of IFN beta polypeptides of the invention. Similarly, IFN beta polypeptides of the invention may be administered to cynomolgus monkeys. The animals are bled prior to and at time points after dosing. Plasma is collected from each sample and analyzed by radioimmunoassay. U.S. Pat. No. 6,962,978, which is incorporated by reference herein, describes pharmacodynamics and pharmacokinetics studies of IFN beta in primates.

Polypeptides of the invention may be administered to an animal model of disease, such as the mouse or rat EAE model for multiple sclerosis. An animal model such as the commonly used experimental autoimmune encephalomyelitis (EAE) model can be used to establish efficacy of a polypeptide of the invention. In the EAE model, immunization with myelin or myelin derived proteins elicits a disease mimicking the majority of the inflammatory and neurologic features of multiple sclerosis in humans. EAE has been used in mice, rats, rabbits, and marmosets (Cannella et al. PNAS, 95, 10100 5, 1998, Zaprianova et al. Morfologiia, 112, 25 8, 1997, Hassouna et al. J. Urology, 130, 806 10, 1983, Genain & Hauser J. Mal. Med. 75, 187 97, 1997). Other models include Theiler's murine encephalomyelitis virus (TMEV) model (Murray et al. J. Neurosci. 18, 7306 14, 1998), may be used to establish efficacy of the IFN beta polypeptide.

Example 26

Human Clinical Trial of the Safety and/or Efficacy of PEGylated IFN Beta Comprising a Non-Naturally Encoded Amino Acid Objective To observe the safety and pharmacokinetics of subcutaneously administered PEGylated recombinant human IFN beta comprising a non-naturally encoded amino acid.

Patients Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to IFN beta within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design This will be a Phase I, single-center, open-label, randomized, two-period crossover study in healthy male volunteers. Eighteen subjects are randomly assigned to one of two treatment sequence groups (nine subjects/group). IFN beta is administered over two separate dosing periods as a bolus s.c. injection in the upper thigh using equivalent doses of the PEGylated IFN beta comprising a non-naturally encoded amino acid and a commercially available product such as BETASERON®, REBIF®, or AVONEX®. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated IFN beta as well. The experimental formulation of IFN beta is the PEGylated IFN beta comprising a non-naturally encoded amino acid.

Blood Sampling Serial blood is drawn by direct vein puncture before and after administration of IFN beta. Venous blood samples (5 mL) for determination of serum IFN beta concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods An ELISA kit is used for the determination of serum IFN beta concentrations.

Safety Determinations Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline IFN beta concentrations by subtracting from each of the post-dose values the mean baseline IFN beta concentration determined from averaging the IFN beta levels from the three samples collected at 30, 20, and 10 minutes before dosing. Pre-dose serum IFN beta concentrations are not included in the calculation of the mean value if they are below the quantification level of the assay. Pharmacokinetic parameters are determined from serum concentration data corrected for baseline IFN beta concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results Mean serum IFN beta concentration-time profiles (uncorrected for baseline IFN beta levels) in all 18 subjects after receiving PEGylated IFN beta comprising a non-naturally encoded amino acid at each time point measured. All subjects should have pre-dose baseline IFN beta concentrations within the normal physiologic range. Pharmacokinetic parameters are determined from serum data corrected for pre-dose mean baseline IFN beta concentrations and the $C_{max}$ and $t_{max}$ are determined. The mean $t_{max}$ for the any clinical comparator(s) chosen is significantly shorter than the $t_{max}$ for the PEGylated IFN beta comprising the non-naturally encoded amino acid. Terminal half-life values are significantly shorter for the preclinical comparator(s) tested compared with the terminal half-life for the PEGylated IFN beta comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated IFN beta comprising non-naturally encoded amino acid will be safe and well tolerated by healthy male subjects. Based on a comparative incidence of adverse events, clinical laboratory values, vital signs, and physical examination results, the safety profiles of the commercially available forms of IFN beta and PEGylated IFN beta comprising non-naturally encoded amino acid will be equivalent. The PEGylated IFN beta comprising non-naturally encoded amino acid potentially provides large clinical utility to patients and health care providers.

Example 27

Primate Trial

Definitive Interferon Beta PK/PD

A 14-Day PK/PD Study of Four Interferon-β-1b Analogues Following a Single Subcutaneous Administration in Cynomolgus Monkeys Objective: To evaluate the pharmacokinetics and hematological responses in cynomolgus monkeys to four interferon-β analogues following a single subcutaneous administration compared to vehicle and REBIF® controls.

Acclimation began on study day A1, with subsequent days numbered consecutively. The day of dosing will be designated D1 with subsequent days numbered consecutively. The test articles used were REBIF® (15 μg/kg), M36-30K (3, 15, and 50 μg/kg), M36-40K (3, 15, and 50 μg/kg), F111-30K (3, 15, and 50 μg/kg), and F111-40K (3, 15, and 50 μg/kg). The vehicle used, IFB formulation 2007, is 10 mM Aspartic Acid, 9% Trehalose, pH 4.0

The storage conditions used were at −60° C. or below and the handling instructions used were standard laboratory precautions as defined in SNBL USA SOPs.

Test or Control Article/Vehicle Preparation:

Test Article Thaw the test articles overnight at 2-8° C. Carefully mix the test article by gently inverting the vial 5-6 times. Do not shake or agitate the solution. Perform dilution procedures immediately after mixing.

Test article dosing solutions will be prepared from stock test articles which have been formulated by the Sponsor at concentrations of 0.20 mg/mL. Test article dosing solutions will be prepared by serial dilution. Sterile containers will be labeled with the final concentration and total volume and placed on ice during the preparations. The appropriate volume of vehicle will be added first and then, using an appropriate size pipette, the appropriate volume of test article solution will be added slowly to the labeled vial containing the previously added vehicle. Do not introduce air bubbles and avoid foaming. Mix well by pipetting up and down 5 to 10 times, Mix the final solution well by inverting the container 7-10 times Positive Control Article: Carefully mix the positive control article by gently inverting the vial 5-6 times prior to use.

Vehicle: Thaw the vehicle solution overnight at 2-8° C. Carefully mix the vehicle by gently inverting the vial 5-6 times.

Test System:

Species: *Macaca fascicularis* (Purpose-bred cynomolgus monkey) is a closely-related species to humans facilitating analysis of both phylogenetically and physiologically, and is a species commonly used for nonclinical toxicity evaluations. Additionally, this species has shown pharmacologic responses to the test article.

| History of Dosing | Naïve animals |
|---|---|
| Body Weight Range | 4.0-6.5 kg |
| Age | 3-6 years |
| Sex | Males |
| Source of Supply | SNBL USA stock |
| Origin | Chinese |
| Method of Identification | Unique skin tattoos and study specific animal number |
| Number of Animals for Acclimation | 49 males |
| Number of Animals for Dosing | 42 males |

Environmental Conditions:

Animals are housed in a temperature- and humidity-monitored environment. The targeted range of temperature and relative humidity is between 18 and 29° C. and 30 and 70%, respectively. Excursions outside of the targeted humidity range for less than 60 minutes are considered incidental and will not be reported. An automatic lighting system will provide a 12-hour diurnal cycle. The dark cycle may be interrupted for study- or facility-related activities.

Also, the animals are individually housed in cages that comply with the Animal Welfare Act and recommendations set forth in "The Guide for the Care and Use of Laboratory Animals" (National Research Council 1996).

Diet and Feeding:

Animals are fed twice per day according to SNBL USA SOPs. Animals may be fasted as required by specific procedures (e.g., prior to blood draws for serum chemistry, urine collection, or when procedures involving anesthesia are performed). The diet is routinely analyzed for contaminants and found to be within manufacturer's specifications. No contaminants are expected to be present at levels that would interfere with the outcome of the study. Food analysis records will be maintained in the testing facility records.

Fresh drinking water is provided ad libitum to all animals. The water is routinely analyzed for contaminants and enrichment toys and produce treats will be routinely supplied according to SNBL USA SOPS.

Experimental Design

Selection of Animals:

An appropriate number of animals was selected from SNBL USA stock. Animals were examined for health by veterinary staff, and underwent serum chemistry, hematology, and coagulation screening. Forty-nine males, confirmed healthy, were assigned to the study. During PE, an additional 1 mL of blood will be collected, processed for serum and shipped to the Sponsor for viral screening.

Forty-two males were assigned to specific study groups at the Sponsor's discretion and the remaining animals were available as spares.

Randomization:

A stratified randomization scheme based on body weights was used to assign animals to study groups.

Acclimation Period:

Previously quarantined animals were acclimated to the study room for a minimum of 14 days prior to initiation of dosing. Acclimation data was collected from all animals, including spares. All animals were assessed for behavioral abnormalities that could affect performance on study. Assigned animals may be replaced with spare animals as needed based on results generated during the acclimation phase. Spare animals will be removed from the study after D1.

Animals were assigned to groups and treated as indicated in the following table:

TABLE 6

GROUP ASSIGNMENTS

| Treatment Group | Test Article | Dose Route | Dose Level (µg/kg) | Dose Concentration (mg/mL) | Dose Volume (mL/kg) | Number of Animals |
|---|---|---|---|---|---|---|
| 1 | Vehicle Control | SC | 0 | N/A | 0.25 | 3 |
| 2 | Rebif® | SC | 15 | 0.06 | 0.25 | 3 |
| 3 | PEG-IFB-1 | SC | 3 | 0.012 | 0.25 | 3 |
| 4 | PEG-IFB-1 | SC | 15 | 0.06 | 0.25 | 3 |
| 5 | PEG-IFB-1 | SC | 50 | 0.2 | 0.25 | 3 |
| 6 | PEG-IFB-2 | SC | 3 | 0.012 | 0.25 | 3 |
| 7 | PEG-IFB-2 | SC | 15 | 0.06 | 0.25 | 3 |
| 8 | PEG-IFB-2 | SC | 50 | 0.2 | 0.25 | 3 |
| 9 | PEG-IFB-3 | SC | 3 | 0.012 | 0.25 | 3 |
| 10 | PEG-IFB-3 | SC | 15 | 0.06 | 0.25 | 3 |
| 11 | PEG-IFB-3 | SC | 50 | 0.2 | 0.25 | 3 |
| 12 | PEG-IFB-4 | SC | 3 | 0.012 | 0.25 | 3 |
| 13 | PEG-IFB-4 | SC | 15 | 0.06 | 0.25 | 3 |
| 14 | PEG-IFB-4 | SC | 50 | 0.2 | 0.25 | 3 |

Note:
Total dose volume (mL) was calculated based on the most recent body weight.

Administration of Test and Control Articles:

Dose levels studied, noted in the Group Assignments Table 6, were selected based on previous studies with cynomolgus monkeys to be in a range from near anticipated human dosages to high multiples of the anticipated human dosage.

Administration Route and Frequency: All groups were dosed subcutaneously in clipped interscapular area of the back and this administration route is consistent with the proposed route of administration in humans and is expected to provide appropriate serum levels for investigation and associated pharmacological activity and pharmacokinetics. Frequency is once.

Observations and Examinations: Data shown throughout FIGS. 6-21, and throughout tables included within this Example provide observations and examinations performed with this protocol. Clinical observations were performed twice daily for each animal beginning on A2. The first observation occurred in the morning, prior to room cleaning. The second observation was no sooner than 4 hours after the morning observation. If clinical observations for an animal demonstrate declining animal condition, a veterinary evaluation is be performed and the Study Director notified. The injection site was evaluated once daily for each animal beginning on Dl. The PK and neopterin time points were 3, 6, 12, 24, 48, 72, 96, 120, 144, 168, 216, 264, and 336 hours following administration. The PD time points were −1, 2, 3, 5, 9, 11, and 15 days post (and −1 being pre) administration. Hematology time points were days −1, 2, 5, 8, 11, 15; and immunogenicity and clinical chemistry time points were −1 and 15 days. Cageside observation: check daily and ISR check twice daily.

Body Weight:

Each animal was weighed during the first week of acclimation, on the day before dosing and at the end of the in-life portion of the study.

4.7. Laboratory Procedures
Frequency Table
Study Day Heme
EDTA (1.3 mL) Chem
SST (1.0 mL) PK
SST (1.0 mL) PD/qPCR

TABLE 7

STUDY DATES OF DATA COLLECTION AND ANALYSES PERFORMED

| Study Day | Heme EDTA (1.3 mL) | Chem SST (1.0 mL) | PK SST (1.0 mL) | PD/qPCR PAXgene (2.5 mL) |
|---|---|---|---|---|
| A1 | | | | |
| A2 | | | | |
| A3 | | | | |
| A4 | | | | |
| A5 | | | | |
| A6 | | | | |
| A7 | | | | |
| A8 | | | | |
| A9 | | | | |
| A10 | | | | |
| A11 | | | | |
| A12 | | | | |
| A13 | | | | |
| A14 | X | X | | |
| D1 | | | pre, 3, 6, 12 hr | pre |
| D2 | X | | 24 hr | X |
| D3 | | | 48 hr | X |
| D4 | | | 72 hr | |
| D5 | X | | 96 hr | X |
| D6 | | | 120 hr | |
| D7 | | | 144 hr | |
| D8 | X | | 168 hr | X |
| D9 | | | | |
| D10 | | | 216 hr | |
| D11 | X | | | X |
| D12 | | | 264 hr | |
| D13 | | | | |
| D14 | | | | |
| D15 | X | X | 336 hr | X |

X: procedure performed

Blood Collection:

General Blood Collection/Sampling Method and Specimen Processing:

Blood was collected by venipuncture from a peripheral vein from restrained, conscious animals. Whenever possible, blood was collected via a single draw and then divided appropriately. Specimens (with the exception of Paxgene) were processed to serum or plasma according to SNBL USA SOPs.

Hematology:

Sample volume of 1.3 mL of blood was collected from all Animals/Groups, anticoagulant EDTA was added, and then the samples were analyzed and hematology parameters were determined using an Advia automated analyzer.

Hematology Parameters: The following parameters were measured and compared to normal ranges:

(Xybion code) White Blood Cells (WBC), Red Blood Cells (RBC), Hemoglobin (HGB), Hematocrit (HCT), Mean Corpuscular Volume (MCV), Mean Corpuscular Hemoglobin (MCH), Mean Corpuscular Hemoglobin Concentration (MCHC), Red Cell Distribution Width (RDW), Platelets (PLT), Mean Platelet Volume (MPV), Reticulocyte Percent (RET %), Reticulocyte Absolute (RETA), and differential leukocyte count (absolute) including; Neutrophils Absolute (NEUA), Lymphocytes Absolute (LYMA), Monocytes Absolute (MONA), Eosinophils Absolute (EOSA), and Basophils Absolute (BASA).

Serum Chemistry Measurements:

For serum chemistry measurements, these were done on all animals/groups and required overnight fasting and a sample volume of 1 mL of blood. No anticoagulant was used, but serum separator tubes were used and chemistry parameters were determined using an Olympus automated analyzer. Parameters included: (Xybion code) Albumin (ALB), Alkaline Phosphatase (ALP), Alanine Aminotransferase (ALT), Aspartate Transaminase (AST), Total Bilirubin (TBIL), Calcium (Ca), Total Cholesterol (TCho), Creatine Kinase (CK), Creatinine (CRN), Gamma Glutamyltransaminase (GGT), Glucose (GLU), Inorganic Phosphorus (IP), Total Protein (TP), Triglyceride (TRIG), Blood Urea Nitrogen (BUN), Globulin (GLOB), Albumin/Globulin Ratio (AIG), Chloride (Cl), Potassium (K), and Sodium (Na).

Specimen Processing and Storage: Serum was divided into two approximately equal volumes and each transferred to a Matrix brand vial and stored at −20° C. or below.

Pharmacodynamic and Quantitative Polymerase Chain Reactions were run on all animals/groups at the frequency given in Table 7 and collection was done using SNBL USA standard operating procedures. Sample volume was approximately 2.5 mL of blood in anticoagulant PAXgene tubes processed and stored at −15° C. to −25° C.

Data From Primate Trial:

TABLE 8

DOSE ALLOMETRIC SCALING - REBIF
Dose allometric scaling Rebif-0.044 mg/injection = ~0.003 mg/kg

| Species | Weight, kg | Est. Total Dost, mg | Dose in mg/kg | Dose in mg/m2 | Est. BSA, m2 |
|---|---|---|---|---|---|
| Human | 65.00 | 0.07 | 0.00 | 0.04 | 1.710 |
| Mouse | 0.02 | 0.00 | 0.00 | 0.00 | 0.007 |
| Hamster | 0.03 | 0.00 | 0.00 | 0.00 | 0.009 |
| Rat | 0.15 | 0.00 | 0.00 | 0.01 | 0.025 |
| Guinea Pig | 1.00 | 0.00 | 0.00 | 0.01 | 0.089 |
| Rabbit | 2.00 | 0.00 | 0.00 | 0.01 | 0.159 |
| Cat | 2.50 | 0.00 | 0.00 | 0.01 | 0.197 |
| Monkey | 4.00 | 0.00 | 0.00 | 0.01 | 0.297 |
| Dog | 8.00 | 0.01 | 0.00 | 0.02 | 0.448 |
| Human | 65.00 | 0.07 | 0.00 | 0.04 | 1.710 |
| Mouse | 0.02 | 0.00 | 0.01 | 0.04 | 0.007 |
| Hamster | 0.03 | 0.00 | 0.01 | 0.04 | 0.009 |
| Rat | 0.15 | 0.00 | 0.01 | 0.04 | 0.025 |
| Guinea Pig | 1.00 | 0.00 | 0.00 | 0.04 | 0.089 |
| Rabbit | 2.00 | 0.01 | 0.00 | 0.04 | 0.159 |
| Cat | 2.50 | 0.01 | 0.00 | 0.04 | 0.197 |
| Monkey | 4.00 | 0.01 | 0.00 | 0.04 | 0.297 |
| Dog | 8.00 | 0.02 | 0.00 | 0.04 | 0.448 |

TABLE 9

DOSE ALLOMETRIC SCALING - BETASERON
Dose allometric scaling - Betaseron 0.25 mg/injection = ~0.013 mg/kg

| Species | Weight, kg | Est. Total Dost, mg | Dose in mg/kg | Dose in mg/m2 | Est. BSA, m2 |
|---|---|---|---|---|---|
| Human | 60.00 | 0.24 | 0.00 | 0.15 | 1.622 |
| Mouse | 0.02 | 0.00 | 0.00 | 0.01 | 0.007 |
| Hamster | 0.03 | 0.00 | 0.00 | 0.01 | 0.009 |
| Rat | 0.15 | 0.00 | 0.00 | 0.02 | 0.025 |
| Guinea Pig | 1.00 | 0.00 | 0.00 | 0.04 | 0.089 |
| Rabbit | 2.00 | 0.01 | 0.00 | 0.05 | 0.159 |
| Cat | 2.50 | 0.01 | 0.00 | 0.05 | 0.197 |
| Monkey | 3.00 | 0.01 | 0.00 | 0.05 | 0.245 |
| Dog | 8.00 | 0.03 | 0.00 | 0.07 | 0.448 |

TABLE 9-continued

DOSE ALLOMETRIC SCALING - BETASERON
Dose allometric scaling - Betaseron 0.25 mg/injection = ~0.013 mg/kg

| Species | Weight, kg | Est. Total Dost, mg | Dose in mg/kg | Dose in mg/m2 | Est. BSA, m2 |
|---|---|---|---|---|---|
| Human | 60.00 | 0.24 | 0.00 | 0.15 | 1.622 |
| Mouse | 0.02 | 0.00 | 0.05 | 0.15 | 0.007 |
| Hamster | 0.03 | 0.00 | 0.04 | 0.15 | 0.009 |
| Rat | 0.15 | 0.00 | 0.03 | 0.15 | 0.025 |
| Guinea Pig | 1.00 | 0.01 | 0.01 | 0.15 | 0.089 |
| Rabbit | 2.00 | 0.02 | 0.01 | 0.15 | 0.159 |
| Cat | 2.50 | 0.03 | 0.01 | 0.15 | 0.197 |
| Monkey | 3.00 | 0.04 | 0.01 | 0.15 | 0.245 |
| Dog | 8.00 | 0.07 | 0.01 | 0.15 | 0.448 |

Based on current therapeutic doses of marketed products and adjusted for body surface area, BETASERON®=32 MIU/mg; REBIF®=270 MIU/mg, and AVONEX®=200 MIU/mg.

TABLE 10

INTERFERON BETA VARIANT DATA

| Test article | Dose (ug/kg) | Cmax (ng/mL) | Tmax (hr) | Terminal HL (hr) | AUC (ng*hr/mL) | Vd/F (mL/kg) | Cl/F (mL/hr/kg) | Lagtime (hr) |
|---|---|---|---|---|---|---|---|---|
| Rebif# | 15 | 10.96 | 9.8 | 6.8 | 284 | 595.8 | 59.96 | n.d. |
| M36-30K* | 3 | n.d. | n.d. | n.d. | n.d. | n.d. | n.d. | n.d. |
| | 15 | 18.4 | 8.1 | 29.2 | 874.5 | 852.5 | 18.8 | n.d. |
| | 50 | 52.7 | 14.8 | 29.7 | 3037.4 | 743.5 | 17.1 | n.d. |
| M36-40K* | 3 | 9.8 | 23.5 | 36.1 | 772.7 | 208.6 | 3.9 | 2.4 |
| | 15 | 81.3 | 14.8 | 32.1 | 4615.9 | 162.3 | 3.5 | 1.7 |
| | 50 | 152.2 | 24.3 | 36.6 | 12932.6 | 204.1 | 3.9 | 0.5 |
| F111-30K* | 3 | n.d. | n.d. | n.d. | n.d. | n.d. | n.d. | n.d. |
| | 15 | 7.1 | 15.8 | 22.3 | 344.9 | 1562.5 | 48.5 | n.d. |
| | 50 | 37 | 11.9 | 24.3 | 1778.9 | 1046.4 | 29.7 | n.d. |
| F111-40K** | 3 | 10.1 | 15.8 | 36.1 | 666.3 | 247.8 | 4.7 | 0.6 |
| | 15 | 39.5 | 22.3 | 47.54 | 3396.9 | 358.8 | 4.9 | 0.3 |
| | 50 | 141.9 | 19.4 | 42.1 | 11201 | 279.6 | 4.6 | 0.6 |

TABLE 11

INTERFERON BETA VARIANT HEMATOLOGICAL DATA

| Treatment Group | PMNs | Platelets | WBCs | RBCS | Lymphocytes Absolute | Monocytes Absolute | Eosinophils Absolute | Basophils Absolute |
|---|---|---|---|---|---|---|---|---|
| Rebif | N.S. | N.S. | N.S. | N.S. | N.S. | N.S. | N.S. | N.S. |
| M36-30K (3 ug) | N.S. | N.S. | N.S. | N.S. | N.S. | N.S. | N.S. | N.S. |
| M36-30K (15 ug) | N.S. | N.S. | N.S. | N.S. | N.S. | N.S. | N.S. | N.S. |
| M36-30K (50 ug) | N.S. | N.S. | N.S. | N.S. | N.S. | N.S. | N.S. | N.S. |
| M36-40K (3 ug) | N.S. | N.S. | N.S. | N.S. | N.S. | N.S. | N.S. | N.S. |
| M36-40K (15 ug) | N.S. | N.S. | N.S. | N.S. | N.S. | N.S. | N.S. | N.S. |
| M36-40K (50 ug) | N.S. | N.S. | N.S. | N.S. | N.S. | N.S. | N.S. | N.S. |
| F111-30K (3 ug) | N.S. | N.S. | N.S. | N.S. | N.S. | N.S. | N.S. | N.S. |
| F111-30K (15 ug) | N.S. | N.S. | N.S. | N.S. | N.S. | N.S. | N.S. | N.S. |
| F111-30K (50 ug) | N.S. | N.S. | N.S. | N.S. | N.S. | N.S. | N.S. | N.S. |
| F111-40K (3 ug) | N.S. | N.S. | N.S. | N.S. | N.S. | N.S. | N.S. | N.S. |
| F111-40K (15 ug) | N.S. | N.S. | N.S. | N.S. | N.S. | N.S. | N.S. | N.S. |
| F111-40K (50 ug) | N.S. | N.S. | N.S. | N.S. | N.S. | N.S. | N.S. | N.S. |

TABLE 12

INTERFERON BETA HEMATOCRIT DATA

| Treatment Group | Hemoglobin | Hematocrit | Mean Corpuscular Volume (MCV) | Mean Corpuscular Hemoglobin (MCH) | Mean Corpuscular Hemoglobin Cone (MCHC) | Red Cell Dist Width (RDW) | Mean Platelet Volume (MPV) |
|---|---|---|---|---|---|---|---|
| Rebif | N.S. | N.S. | N.S. | N.S. | Day 8 | N.S. | N.S. |
| M36-30K (3 ug) | N.S. | N.S. | N.S. | N.S. | N.S. | N.S. | N.S. |
| M36-30K (15 ug) | N.S. | N.S. | N.S. | N.S. | N.S. | N.S. | N.S. |
| M36-30K (50 ug) | N.S. | N.S. | N.S. | N.S. | N.S. | N.S. | N.S. |
| M36-40K (3 ug) | N.S. | N.S. | N.S. | N.S. | N.S. | N.S. | N.S. |
| M36-40K (15 ug) | N.S. | N.S. | N.S. | N.S. | N.S. | NS. | N.S. |
| M36-40K (50 ug) | N.S. | N.S. | N.S. | N.S. | N.S. | N.S. | N.S. |
| F111-30K (3 ug) | N.S. | N.S. | N.S. | N.S. | N.S. | N.S. | N.S. |
| F111-30K (15 ug) | N.S. | N.S. | N.S. | N.S. | N.S. | N.S. | N.S. |
| F111-30K (50 ug) | N.S. | N.S. | N.S. | N.S. | N.S. | N.S. | N.S. |
| F111-40K (3 ug) | N.S. | N.S. | N.S. | N.S. | N.S. | N.S. | N.S. |
| F111-40K (15 ug) | N.S. | N.S. | N.S. | N.S. | N.S. | N.S. | N.S. |
| F111-40K (50 ug) | N.S. | N.S. | N.S. | N.S. | N.S. | N.S. | N.S. |

*Significant different using one-way ANOVA with Bonferonni post hoc ($p > 0.05$)

MCHC difference at Day 8 post treatment is $31.5 \pm 0.8$ g/dL (Vehicle control) vs $33.9 \pm 0.9$ g/dL (REBIF®)
Average of all groups at Day 8 is $32.6 \pm 0.6$ g/dL. Historical reference range is $30.3 \pm 1.11$ g/dL AUC of 3 µg/kg REBIF® (equivalent human dose)=13.6 ng*hr/mL, administered three times per week=40.8 ng*hr/mL, and AUC of a single dose of M36-40K at 3 µg/kg equaled 19× the AUC of weekly administration of REBIF®.

In terms of white blood cells, there were some significant neutrophil decreases in the REBIF®, M36-30K (15 and 50 µg/kg doses), M36-40K (15 and 50 µg/kg doses), F111-30K (50 µg/kg dose), and F111-40K (3 and 50 µg/kg doses), however the range at Day −1 was from 1.92 to 5.66 ($10^3$/µL), the historical range from SNBL was $5.37 \pm 2.75$ ($10^3$/µL), and all groups had returned to pre-dose levels by Day 15 post treatment (and most had returned by Day 5 post treatment).

In terms of clinical chemistry, there were no significant differences from control values and there was a trend of increased serum ALT levels in one group. F111-30K had increases in all groups from Day −1 to Day 15 post treatment, however there was a very large standard deviation in all groups and the historical range from SNBL was $36 \pm 12$ U/L [F111-30K (3 µg/kg dose): 36 to 49 U/L; F111-30K (15 µg/kg dose): 34 to 60 U/L; F111-30K (50 µg/kg dose): 32 to 57 U/L] and there were no other related changes in measures of liver function.

Example 28

Purpose

The following method is to be used to assess relative purity and potential chemical degradation (i.e. oxidation), and process related impurities, of un-PEGylated, and 40K PEGylated Interferon-β (PEG-IFB) by reverse phase high performance liquid chromatography (RP-HPLC).

Principle

RP-HPLC is a technique that separates molecules on the basis of relative hydrophobicities. Samples are passed over a stationary phase of silica covalently bonded to hydrocarbon chains. The molecules of interest are retarded by the stationary phase and eluted with a gradient mobile phase. The chromatographic elution time is characteristic for a particular molecule. This method separates IFB and PEG-IFB from isoforms based on subtle differences in hydrophobicity and retention behavior associated with structural modifications such as oxidation.

Scope

This method is to support identification and purity assessment of IFB and PEG-IFB. Some partial degradation products, and process related impurities are observable using this technique. Only partial resolution of certain methionine oxidation sites and potential deamidation can be observed using this method.

Limits

Nominal injection=10 µg
Linearity achieved with injection amounts of 50-150% of nominal 1. Materials and Equipment
   Adjustable P20, P200, P1000 Pipetman, or equivalent.
   Disposable P20, P200, and P1000 pipet tips.
   HPLC vials and caps (Alltech 100 µl screw cap polypropylene vials #12962, TFE liner caps #73048, open hole screw caps #73044, or equivalent)
   Clean 1 and 2 L glass bottles
   Column—Agilent Zorbax 300SB-C3, 4.6×150 mm, 3.5-micron, 300 Å (P.N. 863973-909)
   High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), and Chemstation chromatography software)
2. Reagents
   a. Water, Milli-Q quality or equivalent
   b. Solid chemicals are analytical grade or better and solvents are HPLC grade or better, unless otherwise noted. Storage of reagents and procedural steps occur at room temperature, unless otherwise indicated.
   c. Example of Ambrx Chemicals:
      i. Acetonitrile, Fisher A998, HPLC grade, or equivalent
      ii. Trifluoroacetic Acid, Halocarbon UN2699, Biograde, or equivalent
   d. Mobile Phase A: 0.1% (v/v) TFA in $H_2O$
   e. Mobile phase B: 0.1% (v/v) TFA in Acetonitrile Samples
   a. Inject enough volume of sample solution to load 10 µg of protein.

Procedure
a. Instruments may be set to the following conditions
  i. Column: Agilent Zorbax 300SB-C3, 4.6×150 mm, 3.5-micron, 300 Å
  ii. Auto sampler Temperature: 4° C.
  iii. Flow rate: 1.0 mL/min
  iv. Pump Setup:

| Time (min) | % A | % B |
|---|---|---|
| 0 | 65 | 35 |
| 2 | 65 | 35 |
| 10.5 | 54 | 46 |
| 17 | 51.4 | 48.6 |
| 26 | 45 | 55 |
| 31 | 30 | 70 |
| 32 | 65 | 35 |
| 37 | 65 | 35 |

Injector Setup: Injection:
Standard Injection
  Injection Volume: Varies
  Draw Speed: 100 μl/min
  Injection Speed: 100 μl/min
  Needle wash: 20 μl $H_2O$
  Stop Time As pump
  DAD Signals: Sample
Bw Reference Bw Units

| Monitoring Wavelength | | | |
|---|---|---|---|
| 214 | 4 | 600 | 100 nm |
| 276 | 4 | 600 | 100 nm |
| 280 | 16 | 600 | 100 nm |
| 220 | 4 | 600 | 100 nm |
| 250 | 8 | 600 | 100 nm |

Peak Width: >0.1 min
Slit: 4 mm
Stop Time: as pump
Column Thermostat Temperature: 25° C.
Integration Events Dependent upon analysis software b. New columns should be flushed with at least 10CV of distilled HPLC-grade water to remove the shipping solvent.
c. Cleaning procedure: Flush column with greater than 10CV of HPLC-grade water followed by 10-15 CV of 100% methanol.
d. Storage procedure: Store column in 100% methanol.
e. Running procedure: Equilibrate column with 10-15 column volumes of 100% mobile phase A.
f. Inject the test article and run the HPLC program.

Data Analysis
  a. Retention Time (using $A_{214}$)
    Report the retention time of the test article:
  b. Purity
    Calculate the purity of the test article:
    (Integration area of the main peak/integration areas of all peaks)×100%

Examples of chromatograms produced and purifies from this procedure are provided in FIGS. 24-28.

It is understood that the examples and embodiments described herein are for illustrative purposes only and that various modifications or changes in light thereof will be suggested to those of ordinary skill in the art and are to be included within the spirit and purview of this application and scope of the appended claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 6

| Sequences Cited. | |
|---|---|
| SEQ ID # | Sequence Name |
| 1 | Amino acid sequence of IFN beta with C17S substitution |
| 2 | Nucleotide sequence of IFN beta with C17S substitution (optimized 5' end) |
| 3 | Amino acid sequence of IFN beta without C17S substitution |
| 4 | Amino acid sequence with N terminal sequence without C17S substitution |

What is claimed is:

1. An interferon (IFN) beta polypeptide comprising non-naturally encoded amino acid at a position selected from the group consisting of residues 28, 36, 76, 80, 107, 108 and 111 (SEQ ID NO: 1 or the corresponding amino acids of SEQ ID NOs: 3, 4), wherein the non-naturally encoded amino acid has the structure:

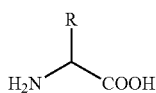

and the R group is any substituent other than one used in the twenty natural amino acids, and wherein the non-naturally encoded amino acid is conjugated to one or more lipid molecule(s).

2. The IFN beta polypeptide of claim 1, wherein the IFN beta polypeptide increases affinity of the IFN beta polypeptide for an IFN receptor.

3. The IFN beta polypeptide of claim 1, wherein the IFN beta polypeptide has increased stability or solubility compared to the native IFN beta polypeptide.

4. The IFN beta polypeptide of claim 1, wherein the IFN beta polypeptide has increased protease resistance compared to the native IFN beta polypeptide.

5. The IFN beta polypeptide of claim 1, wherein the non-naturally encoded amino acid comprises a carbonyl group, an aminooxy group, a hydrazine group, a hydrazide group, a semicarbazide group, an azide group, or an alkyne group.

6. The IFN beta polypeptide of claim 5, wherein the non-naturally encoded amino acid is a para-acetyl-phenylalanine.

* * * * *